US010421788B2

(12) United States Patent
Alter et al.

(10) Patent No.: US 10,421,788 B2
(45) Date of Patent: Sep. 24, 2019

(54) SYNTHESIZING VACCINES, IMMUNOGENS, AND ANTIBODIES

(71) Applicants: THE GENERAL HOSPITAL CORPORATION, Boston, MA (US); UNIVERSITY OF GEORGIA RESEARCH FOUNDATION, Athens, GA (US)

(72) Inventors: Galit Alter, Winchester, MA (US); Robert Lance Wells, Athens, GA (US); Wen-Han Yu, Brookline, MA (US)

(73) Assignees: THE GENERAL HOSPITAL CORPORATION, Boston, MA (US); UNIVERSITY OF GEORGIA RESEARCH FOUNDATION, Athens, GA (US)

(*) Notice: Subject to any disclaimer, the term of this patent is extended or adjusted under 35 U.S.C. 154(b) by 0 days.

(21) Appl. No.: 15/759,164

(22) PCT Filed: Sep. 9, 2016

(86) PCT No.: PCT/US2016/051108
§ 371 (c)(1),
(2) Date: Mar. 9, 2018

(87) PCT Pub. No.: WO2017/044850
PCT Pub. Date: Mar. 16, 2017

(65) Prior Publication Data
US 2018/0282376 A1 Oct. 4, 2018

Related U.S. Application Data

(60) Provisional application No. 62/216,643, filed on Sep. 10, 2015.

(51) Int. Cl.
*A61K 39/21* (2006.01)
*A61K 39/00* (2006.01)
*A61K 38/00* (2006.01)
*C07K 14/00* (2006.01)
*C07K 16/00* (2006.01)
*C07K 14/005* (2006.01)
*G16B 15/00* (2019.01)
*G16B 40/00* (2019.01)
*C12N 7/00* (2006.01)
*C07K 16/10* (2006.01)

(52) U.S. Cl.
CPC ........ *C07K 14/005* (2013.01); *C07K 16/1063* (2013.01); *C12N 7/00* (2013.01); *G16B 15/00* (2019.02); *G16B 40/00* (2019.02); *A61K 39/00* (2013.01); *C12N 2740/16222* (2013.01); *C12N 2740/16234* (2013.01)

(58) Field of Classification Search
CPC ........ C07K 14/005; C12N 2740/16122; A61K 2039/53; A61K 2039/545; A61K 39/12
See application file for complete search history.

(56) References Cited

U.S. PATENT DOCUMENTS

| 7,687,060 B2 | 3/2010 | Jolles et al. |
| 2006/0252075 A1 | 11/2006 | Zagury et al. |
| 2013/0149300 A1 | 6/2013 | Hiatt et al. |
| 2013/0280238 A1 | 10/2013 | Evans et al. |

OTHER PUBLICATIONS

Julien et al., Design and structure of two HIV-1 clade C SOSIP.664 trimers that increase the arsenal of native-like Env immunogens, Proceedings of the National Academy of Sciences, 2015, 112: 38, p. 11947-11952.*
Go et al., Glycosylation Site-Specific Analysis of Clade C HIV-1 Envelope Proteins, Journal of Proteome Research, 2009, 8: 9, p. 4231-4242.*
Julien et al., "Design and structure of two HIV-1 clade C SOSIP.664 trimers that increase the arsenal of native-like Env immunogens", PNAS, 2015 112(38):11947-11952.*
Go et al., "Glycosylation site-specific analysis of clade C HIV-1 envelope proteins", J Proteome Res., 2009, 8(9):4231-4242.*
Ackerman et al., "Natural variation in Fc glycosylation of HIV-specific antibodies impacts antiviral activity", J Clin Invest. 123(5):2183-2192 (2013).
Caragea et al., "Glycosylation site prediction using ensembles of Support Vector Machine classifiers", BMC Bioinformatics 8:438 (2007).
Go et al., "Glycosylation site-specific analysis of clade C HIV-1 envelope proteins", J Proteome Res 8(9):4231-4242 (2009).
Julien et al., "Design and structure of two HIV-1 clade C SOSIP.664 trimers that increase the arsenal of native-like Env immunogens" PNAS 112(38) 11947-11952 (2015).
Mahan et al. "Antigen-specific antibody glycosylation is regulated via vaccination." PLoS pathogens 12(3) e1005456:1-18 (2016).
Poon et al., "Evolutionary interactions between N-linked glycosylation sites in the HIV-1 envelope", PLoS Comput Biol 3(1) e11 (2007).
SPARTAC Trial Investigators. "Short-course antiretroviral therapy in primary HIV infection." N Engl J Med 2013 (368):207-217 (2013).
Spivak et al., "HIV-1 eradication: early trials (and tribulations)." Trends in molecular medicine 22(1):10-27 (2016).
Williams et al., "HIV-1 DNA predicts disease progression and post-treatment virological control." Elife 3 e03821:1-16 (2014).
Calarese et al., "Antibody domain exchange is an immunological solution to carbohydrate cluster recognition." Science 300(5628):2065-2071 (2003).

(Continued)

*Primary Examiner* — Barry A Chestnut
(74) *Attorney, Agent, or Firm* — Nixon Peabody, LLP

(57) ABSTRACT

Systems and methods have been developed to design and engineer glycan dynamics to improve immunogen antigenicity. These include systems for identify glycosylation sites that that impact binding of antibodies to the immunogen, and modifying the glycan profiles on these glycosylation sites to synthesize novel immunogens, antibodies and vaccines. Then, the machine learning algorithm may output data relating to the glycosylation sites that are determinant or likely impact the binding affinity of the variants to the one or more antibodies.

18 Claims, 49 Drawing Sheets

(56) References Cited

OTHER PUBLICATIONS

Julien et al., "Crystal structure of a soluble cleaved HIV-1 envelope trimer." Science 342:1477-1783 (2013).
Kolchinsky et al., "Increased neutralization sensitivity of CD4-independent human immunodeficiency virus variants." Journal of Virology 75(5):2041-2050 (2001).
Kong et al., "Supersite of immune vulnerability on the glycosylated face of HIV-1 envelope glycoprotein gp120." Nature Structural and Molecular Biology 20(7):796-803 (2013).
Kwong et al., "Structure of an HIV gp120 envelope glycoprotein in complex with the CD4 receptor and a neutralizing human antibody." Nature 393(6686):648-659 (1998).
Lyumkis et al., "Cryo-EM structure of a fully glycosylated soluble cleaved HIV-1 envelope trimer." Science 342 (6165):1484-1490 (2013).
McGuire et al., "Engineering HIV envelope protein to activate germline B cell receptors of broadly neutralizing anti-CD4 binding site antibodies." Journal of Experimental Medicine 210:655-663 (2013).
McLellan et al., "Structure of HIV-1 gp120 V1/V2 domain with broadly neutralizing antibody PG9." Nature 480 (7377):336-343 (2011).
Pancera et al., "Structural basis for diverse N-glycan recognition by HIV-1-neutralizing V1-V2-directed antibody PG16." Nature Structural and Molecular Biology 20(7):804-813 (2013).
Pejchal et al., "A potent and broad neutralizing antibody recognizes and penetrates the HIV glycan shield." Science 334(6059):1097-1103 (2011).
Wyatt et al., "Functional and immunologic characterization of human immunodeficiency virus type 1 envelope glycoproteins containing deletions of the major variable regions." Journal of Virology 67(8):4557-4565 (1993).
Anthony et al., "Intravenous gammaglobulin suppresses inflammation through a novel T H 2 pathway." Nature 475 (7354):110-113 (2011).
Jefferis et al., "Glycosylation of antibody molecules: structural and functional significance." Antibody Engineering 65:111-128 (1997).
Rademacher et al., "The role of IgG glycoforms in the pathogenesis of rheumatoid arthritis." Springer Seminars in Immunopathology 10(2-3):231-249 (1988).

* cited by examiner

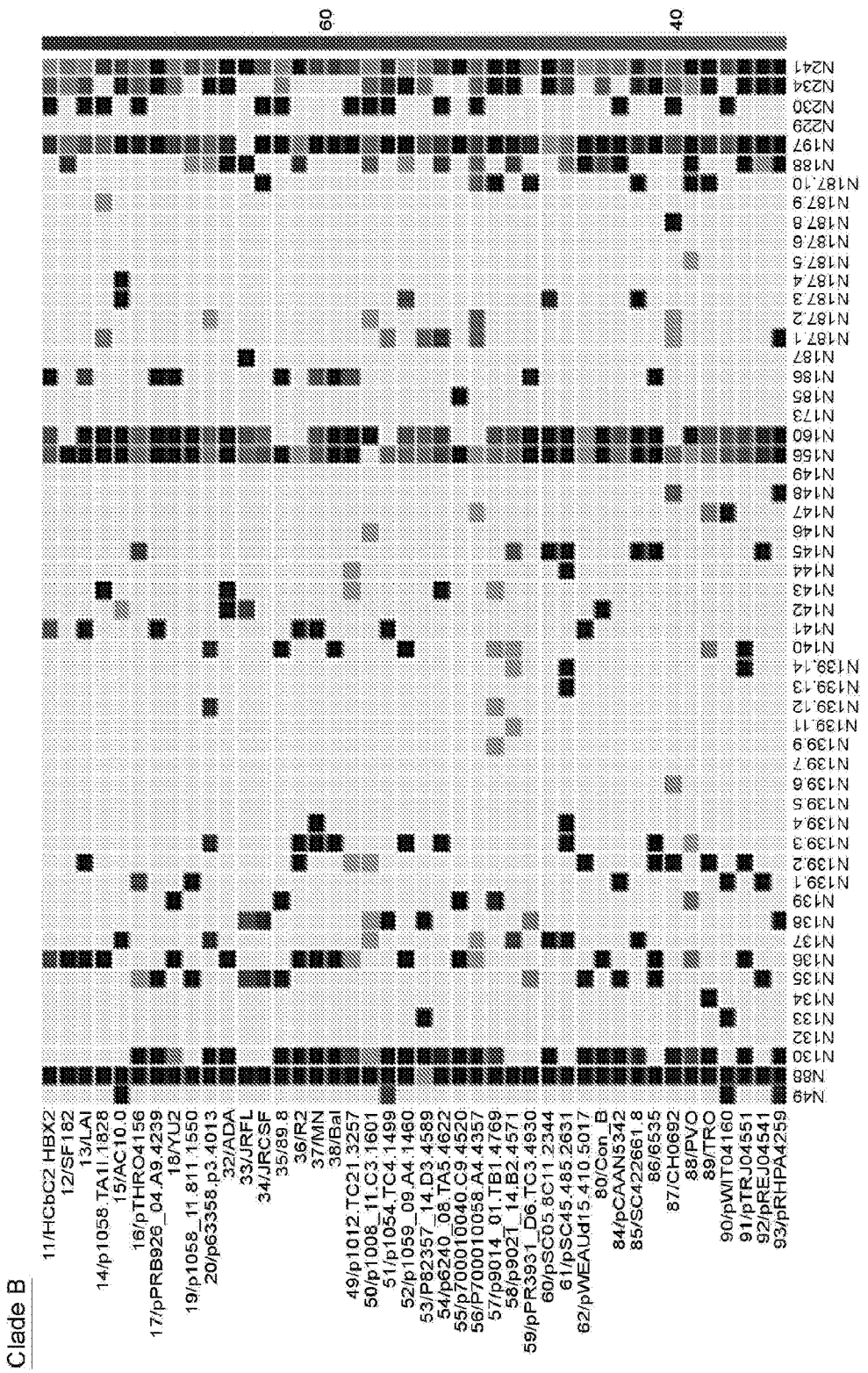
FIG. 1Aii

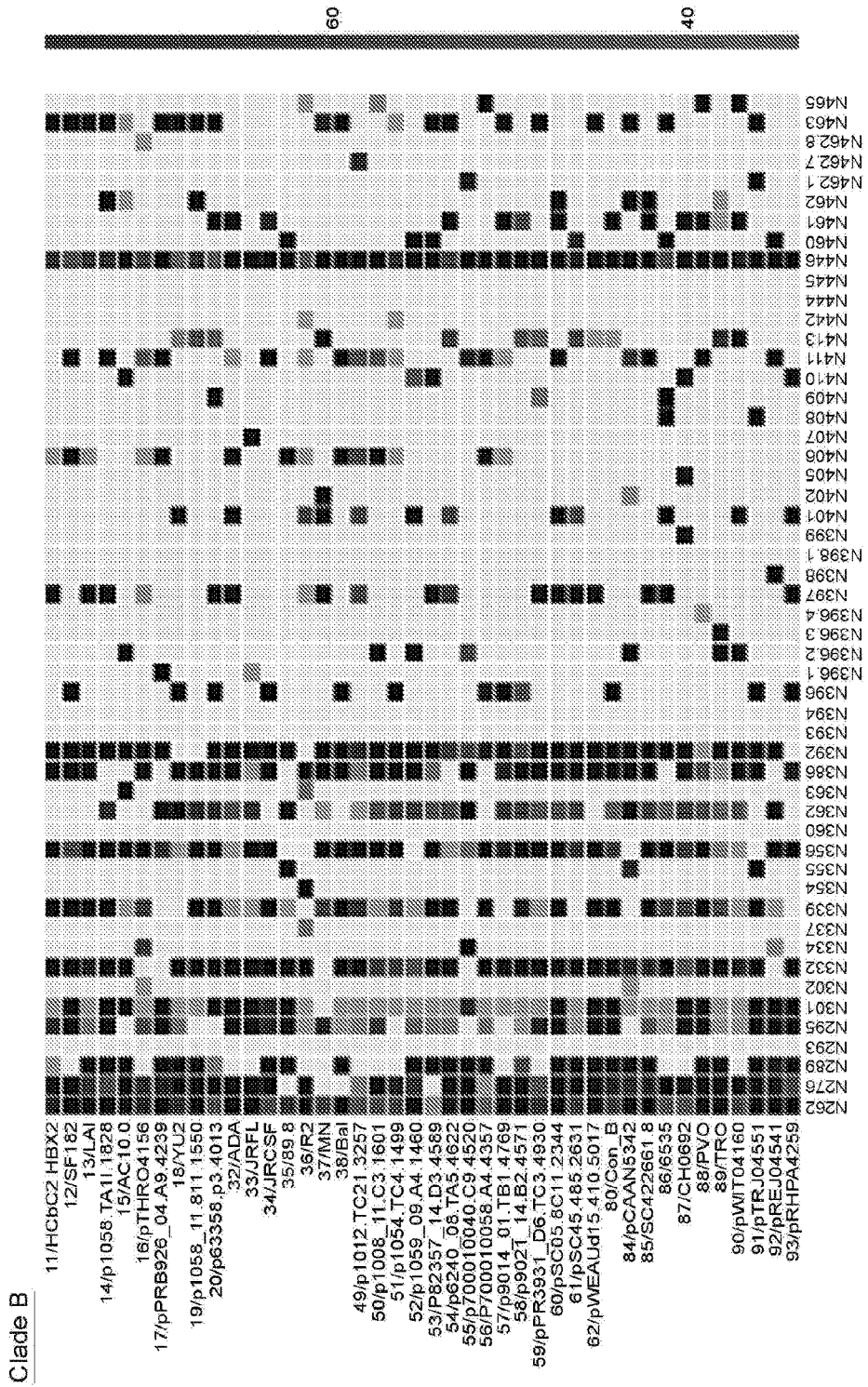
FIG. 1Aii (continued)

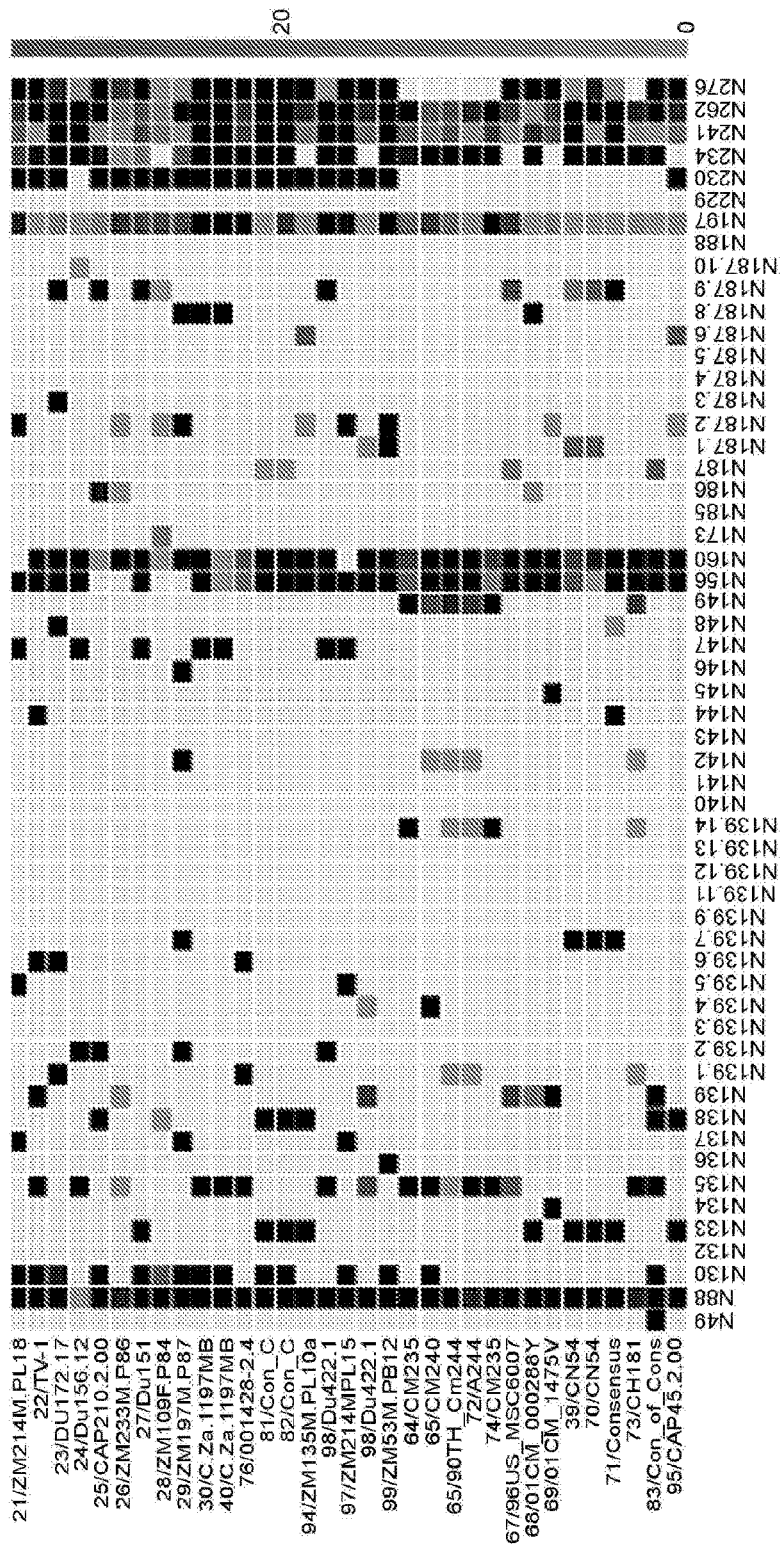
FIG. 1Aiii

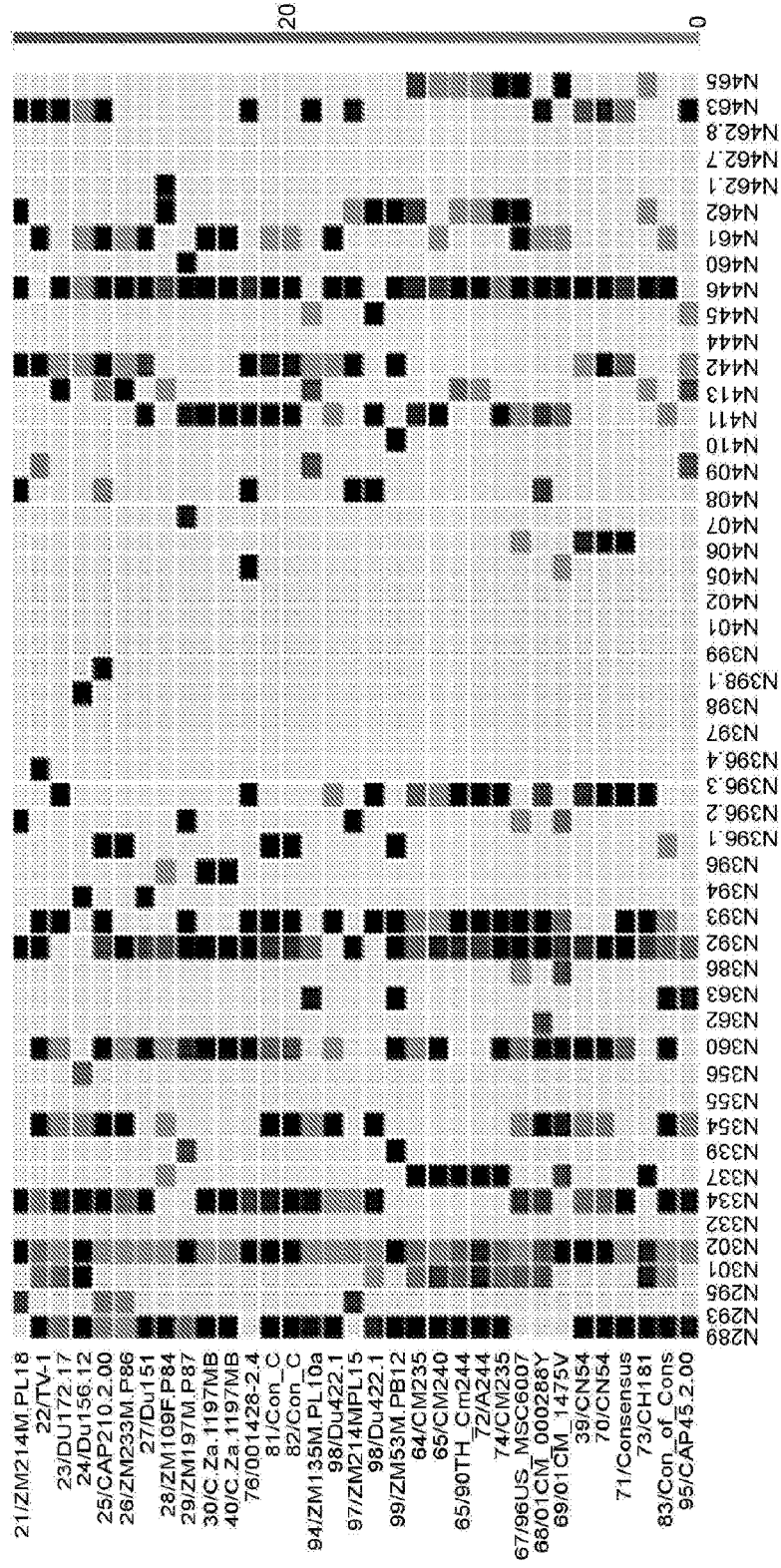
FIG. 1Aiii (continued)

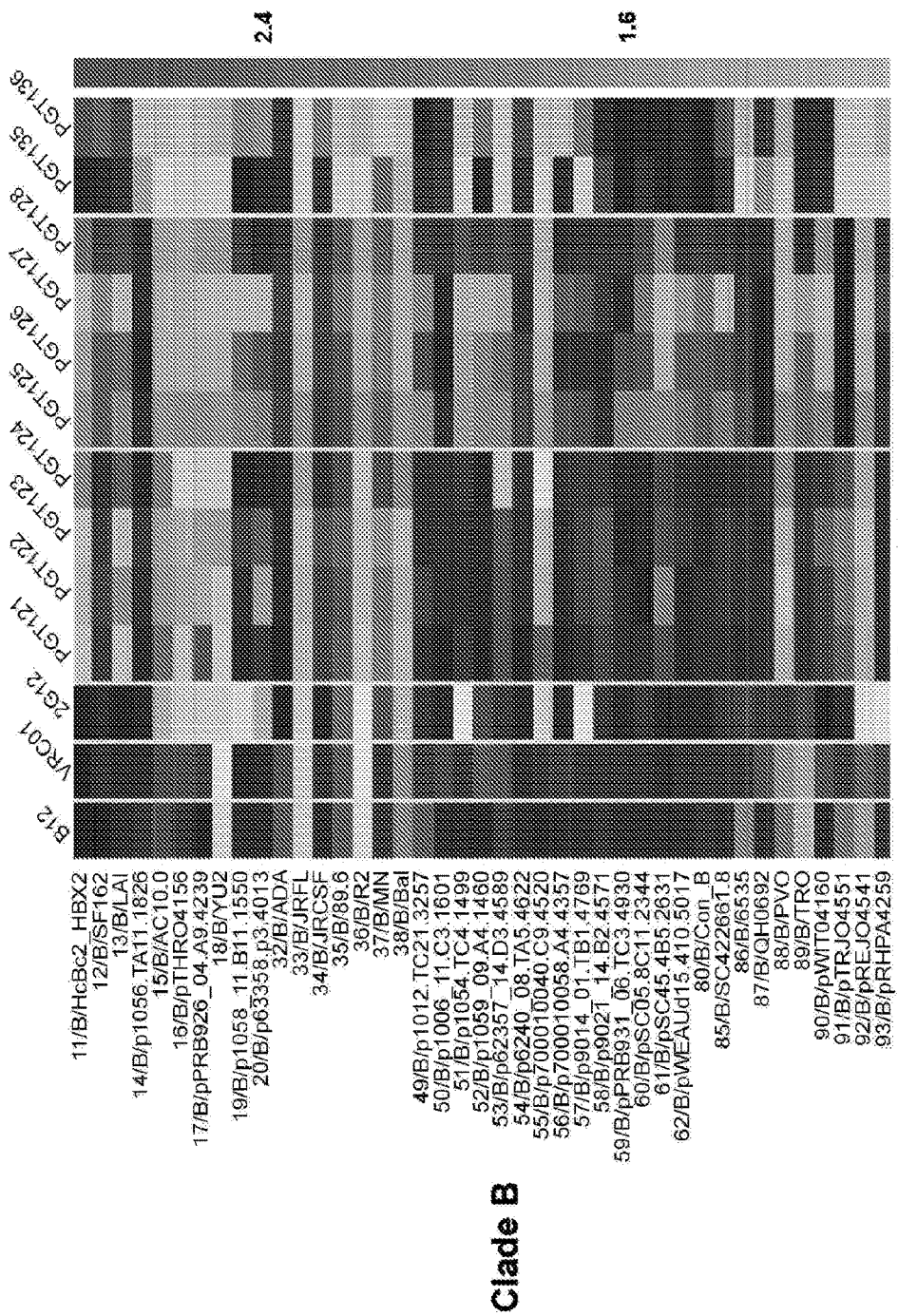
FIG. 2Aii

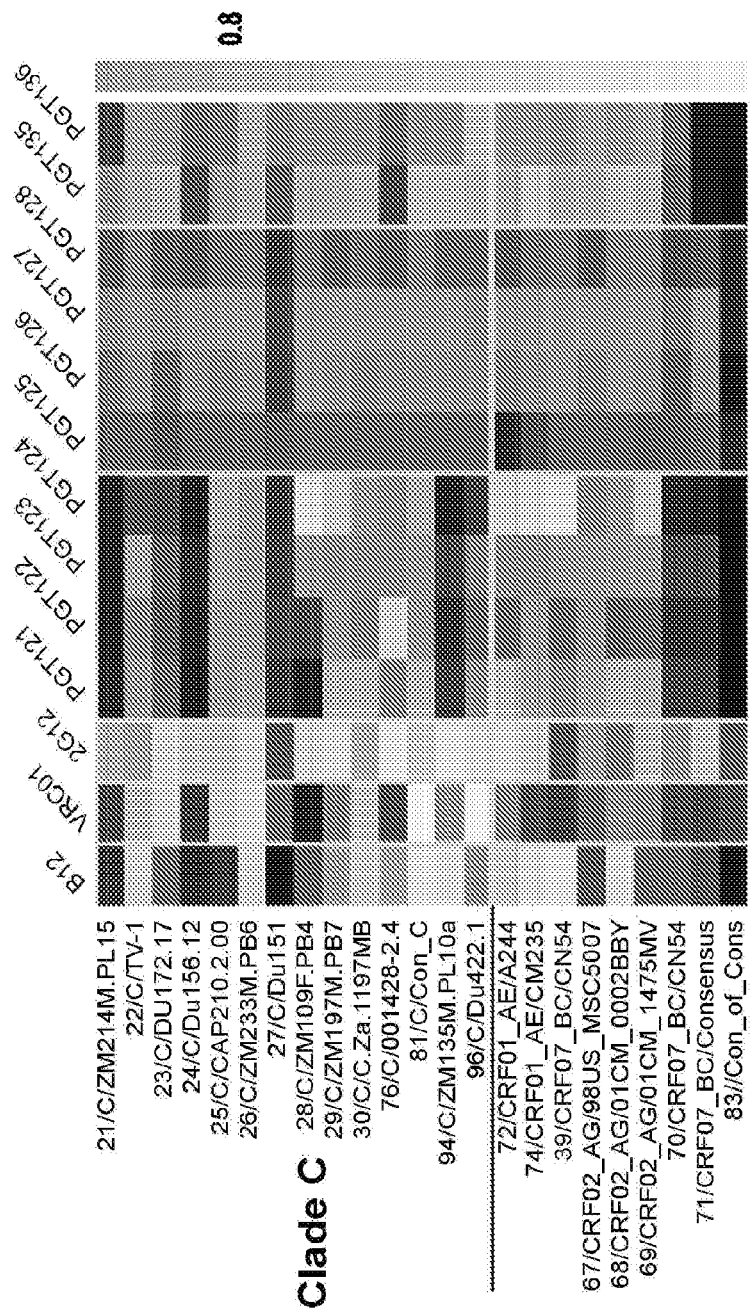
FIG. 2Aiii

C)

$r = 0.81$
$p = 0.0041$

Breadth (%) from neutralization vs Breadth (%) from antigenicity

D)

B12
VRC01
2G12
PGT135
PGT136
PGT124
PGT121
PGT122
PGT123
PGT125
PGT127
PGT126
PGT128

FIG. 2C-2D

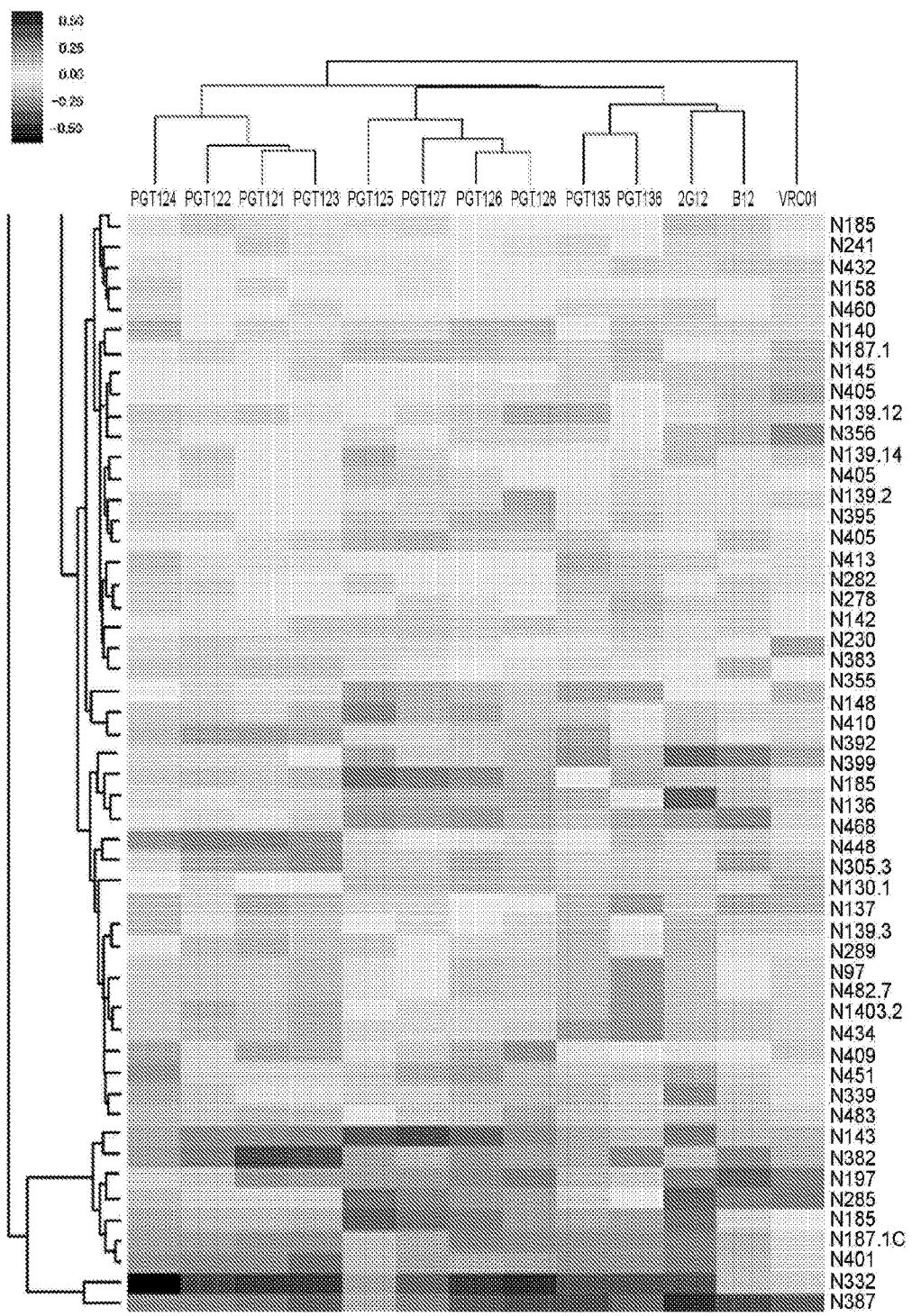
FIG. 3Cii

```
┌─────────────────────────┐
│ Provide mutants of antigen │
│          1500           │
└─────────────┬───────────┘
              ▼
┌─────────────────────────┐
│  Provide antibody known to │
│      bind to antigen    │
│          1510           │
└─────────────┬───────────┘
              ▼
┌─────────────────────────┐
│ Determine binding affinity │
│  of mutants for antibody │
│          1520           │
└─────────────┬───────────┘
              ▼
┌─────────────────────────┐
│  Identify glycosylation │
│    sites for antigen    │
│          1530           │
└─────────────┬───────────┘
              ▼
┌─────────────────────────┐
│ Determine glycan occupancy│
│ rates for glycosylation sites│
│          1540           │
└─────────────┬───────────┘
              ▼
┌─────────────────────────┐
│ Identify glycosylation sites│
│   that are determinants │
│          1550           │
└─────────────┬───────────┘
              ▼
┌─────────────────────────────────────┐
│ Synthesize immunogen with altered affinity for│
│ antibody by modifying determinant glycosylation sites│
│               1560                  │
└─────────────────────────────────────┘
```

FIG. 15

SYNTHESIZING VACCINES, IMMUNOGENS, AND ANTIBODIES

CROSS-REFERENCE TO RELATED APPLICATIONS

This application is a 35 U.S.C. § 371 National Phase Entry Application of International Application No. PCT/US2016/051108 filed Sep. 9, 2016, which designates the U.S. and claims benefit under 35 U.S.C. § 119(e) of U.S. Provisional Application No. 62/216,643, filed Sep. 10, 2015, the contents of which are incorporated herein by reference in their entireties.

FIELD

The present invention is directed to engineering and synthesis of immunogens, antibodies, and vaccines.

BACKGROUND

The following description includes information that may be useful in understanding the present invention. It is not an admission that any of the information provided herein is prior art or relevant to the presently claimed invention, or that any publication specifically or implicitly referenced is prior art.

Broadly neutralizing antibodies (bNAbs) develop in 10-30% of HIV-1 positive individuals (Doria-Rose et al., 2009; Sather et al., 2009). However these responses only develop after several years of infection (Stamatatos et al., 2009), requiring extensive selection to effectively recognize a limited set of epitopes on the viral envelope that are able to interfere with viral infectivity. However, despite our rapidly expanding portfolio of highly potent bNAbs, and our growing appreciation for how these antibodies (Abs) bind and neutralize the virus, to date immunogens continue to fail to induce appreciable neutralizing breadth. Thus efforts aimed at improving the antigenic profiles of gp120 immunogens, in a manner that can selectively drive antibodies against sites of neutralizing vulnerability are needed.

Due to remarkable technological advances in antibody sequencing and cloning, dozens of novel HIV-specific bNAbs have been identified (Scheid et al., 2009). Interestingly, the majority of these novel antibodies show varying degrees of interactions with carbohydrates on the envelop (Falkowska et al., 2014; Walker et al., 2011), and co-crystal structures of gp120 in complex with the bNAb demonstrate the direct interactions of some of these bNAbs with specific glycans on gp120 (Calarese et al., 2003; Julien et al., 2013a; Kong et al., 2013; Lyumkis et al., 2013; McLellan et al., 2011; Pancera et al., 2013; Pejchal et al., 2011), highlighting the antigenic nature of the HIV envelope glycan shields. Moreover, mutagenesis studies have shown that the acquisition (or loss) of single specific N-linked glycosylation sites abrogate viral neutralization (Falkowska et al., 2014; Walker et al., 2011).

Glycans may play three distinct roles in modulating bNAb binding: (i) glycans can agonize or participate in bNAb binding within the epitope, such as the glycan at N332 critical for 2G12 (Calarese et al., 2003) and PGT family binding (Julien et al., 2013a; Kong et al., 2013; Pejchal et al., 2011), or the glycan at N160 which plays a critical role in PG9 and PG16 binding (McLellan et al., 2011; Pancera et al., 2013); (ii) glycans can directly antagonize bNAb binding, such as is observed with improved PGV04 binding to deglycosylated trimers (Lyumkis et al., 2013) due V1V2 loop glycan antagonism that interfere with the CD4 binding (Kwong et al., 1998; Wyatt et al., 1993) or improved binding of VRCO1 and NH45-46 binding in N276-deleted monomers (McGuire et al., 2013); and finally (iii) distal glycans can indirectly impact bNAb recognition via conformational changes in Env, such as V3 loop N197 induced shielding of the V1V2 loop at the apex of the virus (Julien et al., 2013a) or improved Env stability via the removal of the N197 glycan (Kolchinsky et al., 2001). Yet, how these three types of glycan modulators may be collectively harnessed and actively utilized to improve the antigenic profiles of Env in vaccine design strategies has yet to be defined.

SUMMARY

Glycan engineering strategies, to date, have only focused on modifying individual or clusters of proximal glycans around bNAb epitopes (Ingale et al., 2014; Morales et al., 2014; Pantophlet et al., 2003, 2004) rather than for example the overall glycan shield to improve antigenicity. However, given the mass and density of glycans (Leonard et al., 1990), and their impact on protein structure (Wood et al., 2013), it is likely that multiple glycans collaborate to both agonize and antagonize antibody binding in a cooperative manner. For example, N332-dependent mannose patch-targeting antibodies retain neutralizing potency through the use of alternate neighboring glycans when the N332 glycan is lost (Sok et al., 2014), clearly illustrating the complex dynamics of multiple glycans in shaping antibody binding profiles.

Accordingly systems and methods have been developed to design and engineer glycan dynamics to improve immunogen antigenicity. These include systems for identify glycosylation sites that impact binding of antibodies to the immunogen, and modifying the glycan profiles on these glycosylation sites to synthesize novel immunogens.

It has been discovered that glycosylation sites that impact the binding of antibodies may be identified by determining and processing the occupancy rates or the rates of glycosylation at each glycosylation site across variants of antigen protein or immunogen. For instance, the occupancy rates and affinities to one or more antibodies may be utilized to determine once glycosylation sites are most responsible for binding affinity. This may include sites that increase or decrease binding affinity.

In some examples, various statistical or machine learning algorithms may determine or identify glycosylation sites responsible for binding affinity with one or more antibodies. For instance, a machine learning algorithm running on a control system with one or more processors may process data related to the occupancy rates of a given set of glycosylation sites across a multitude of variants, and corresponding binding affinity for each of the variants with one or more antibodies. Then, the machine learning algorithm may output data relating to the glycosylation sites that are determinant or likely impact the binding affinity of the variants to the one or more antibodies.

In some examples, other information or data may be processed by the machine learning algorithm including the conservation rate of glycosylation sites between variants. In some examples, the glycosylation occupancy data may be first processed to reduce dimensionality prior to entering into the machine learning algorithm. This may be performed by a principle component analysis or other dimensionality reduction technique.

In one example, the systems and methods herein were utilized to synthesize an immunogen mimicking the HIV envelope glycoprotein gp120. To perform this, gp120 global PNGS-specific glycan occupancy was defined in 94 recombinant gp120 proteins from a panel of global HIV isolates spanning HIV clade A, B, and C, demonstrating for the first time the remarkable heterogeneity in gp120 glycan occupancy profiles, irrespective of the presence of a sequon, across gp120s of the same clade and/or neutralization tier. Next, bNAb binding activity profiles were assessed against each of the 94 gp120 proteins. These data were integrated using a novel probabilistic machine learning regression algorithm to delineate bNAb-specific glycan determinants critical for binding.

Notably, this objective analysis identified both direct and indirect agonistic and antagonistic glycans for individual bNAbs, highlighted clusters of shared and distinct glycans involved in modulating bNAb binding. Moreover, these fingerprints offered a novel framework upon which a PGT121/PGT128 non-reactive gp120 immunogen was engineered to selectively augment PGT121 and/or PGT128 binding. Together this approach to globally identify and manipulate the functional glycan determinants and engineering of those glycans alone on immunogens offers a novel approach by which the antigenic nature of HIV envelope glycoprotein may be improved to harness B cell immunity more effectively.

This study highlighted a novel approach by which the antigenicity of the HIV glycoprotein envelope immunogen may be engineered, to enhance or block select antibody binding profiles. This approach relies on the remarkable heterogeneity in glycan occupancy at individual sequons as well as across 94 distinct HIV gp120 envelope proteins that predict bNAb binding profiles, due to their direct and indirect participation as agonists or antagonists of bNAb binding. Each bNAb exhibited a unique antibody binding antigenicity fingerprint, that although unique could be clustered as families of bNAbs with shared epitopes, highlighted the landscape of glycans that participate both proximally as well as distally to antibody binding, and linked neutralizing activity (FIG. 10).

Thus, using 13 bNAbs and linked binding profiles to the 94 proteins, with site specific glycan occupancy data, sequences, and structural data, a panel of 5 novel proteins were engineered to either improve binding to both or either PGT121 and PGT128, as well as to selectively improve binding to 1 but diminish binding to the other. Successful augmentation of binding to both or individual bNAbs was observed, with some success in selectively augmenting PGT128 in the absence of PGT121. Thus, these studies offer the proof of concept for a new rational vaccine design approach that may selectively custom design immunogens for any target to which they can bind, by simply harnessing the natural antigenicity of glycans.

While X-ray crystallography provides tremendous power to visualize the interaction between bNAbs domains and the viral envelope at single-atom resolution, only interrogates the relationship of individual Fabs, rather than full bivalent antibodies and more importantly, crystallography requires the truncation of all glycans to N-acetyl glucosamine moiety (Julien et al., 2013a) providing only limited insights into the role of whole glycans in shaping antibody binding interactions.

Moreover, to generate better crystals, envelope proteins have been synthesized in cell lines that are only able to generate homogenous glycans, where N-acetylglucosaminyltransferase I enzyme knock down leads to the generation of only high-mannose ($Man_{5-9}$) glycans (Reeves et al., 2002). However despite these efforts to minimize glycan variability, a role for glycans in bNAb binding has been observed that four glycans (N137, N156/N173, N301 and N332) directly participated in PGT122 recognition (Julien et al., 2013a). Interestingly, the disclosed analysis that probes whole glycans as well as glycan heterogeneity at different sites only identified two of the glycans (N301 and N332) as critical determinants for PGT122 binding.

However, cross gp120 analysis demonstrated that the N137 sequon was rare across gp120 isolates (FIG. 1B) and glycan occupancy at N137 correlated only weakly with PGT122 binding (FIG. 3, 13). Thus while the N137 glycan may have participated in binding in the crystal structure in the BG505 SOSIP.664 envelope utilized, with truncated sugars, the disclosed data illustrates that the presence of N137 may not play as critical of a role in binding. Interestingly, instead of N137, a close glycan was identified, N139, that appeared to antagonize PGT122 binding (FIG. 4A).

In contrast to N173, N156, that was previously identified in the crystal structure, was a highly conserved sequon (FIG. 1B), but glycan occupancy at this site was highly heterogeneous and not significantly correlated with PGT122 binding (FIG. 3, 13) although N156 was protected from EndoH deglycosylation by PGT122 (Julien et al., 2013a). Thus, two explanations may account for the discrepancy at N156: 1) either the N156 glycan may participate in PGT122 binding but the glycan fingerprinting here may suggest that the presence/absence of this glycan may not adversely affect PGT122 binding or 2) the panel of 94 proteins may not cover all "unnatural" glycan variants, particularly for highly conserved glycans such as N156, that may provide additional resolution into the overall glycan occupancy profiles required to gain super-resolution and optimally engineer envelope immunogens to enhance antigenicity. Thus while, N156 sequon/glycan lacking envelopes still appear to bind to PGT122 (FIG. 13) and be effectively neutralized, suggesting that it is not critical glycan for bNAb activity.

The highly flexible nature of the antigenicity binding array allows for the incorporation of many additional naturally occurring and synthetic mutant envelope proteins, including many proteins that are included in neutralization analyses, to comprehensively interrogate and evolve antigenically improved immunogens.

The systems and methods highlighted here critically addressed the mutual dependence between multiple glycosylation sites in an unbiased manner, providing novel insights on how bNAbs respond to highly variable gp120 proteins. Interestingly, glycan substitutions have been suggested as a mechanism by which the virus has been able to evade bNAb binding, as has been observed among PGT family members that utilize variable glycans within the dense glycans mannose patch (N295-N334) in the absence of N332 (Sok et al., 2014). However, the disclosed systems and methods, using proteins that cover variation within the mannose-patch, suggest that just three glycans participate in the PGT121-glycan fingerprints (FIG. 4A).

PGT121 was observed having the dual usage of both N332 and N334 glycans, however PGT121 clearly exhibited a preference for the N332 glycan, whereas the ideal PGT121 footprint included both N332 and N295 glycans (FIG. 14). Furthermore, the integration of the disclosed algorithms with data from the crystallographic studies, the ideal glycan fingerprint for PGT121 was defined, including N295, N332, N334, N362, N386 and N397 (FIG. 14), that likely cooperate to improve PGT121 binding. Along these lines, gp120 isolates that PGT121 bound most effectively possessed the N295, N332 N362 and N397 glycan, but lacked glycans at N334 and N386. However a few changes of these glycans did not abrogate PGT121 recognition due to the cooperative binding to other glycans within that matrix. Thus, these results highlight the use of the glycan fingerprinting technique, linked to crystal structure data, to either a) define ideal bNAb footprints, b) define minimal glycans required for bNAb binding, and c) linked to neutralization, determine the glycans required for neutralization.

Recent data indicated that several bNAbs occasionally showed a non-sigmoidal neutralization curve with <100% neutralization, suggesting a mixed populations of viruses with varying sensitivity to antibody, a percentage of which are not neutralized by a given antibody and lead to the resistance (McCoy et al., 2015). Moreover, as McCoy et al. suggested, the mechanism of incomplete neutralization may relate to glycosylation heterogeneity on the envelope. The disclosed systems and methods have shown that those identified glycan determinants indeed played critical roles to shape the landscape of the binding activity, a reasonable hypothesis that the glycans may contribute to virus's resistance to neutralization was proposed.

While the relationship of bNAb binding to 94 proteins was examined here for only a single optimized antibody concentration, future analysis and applications of the disclosed systems and methods focused on a range of antibody concentrations may provide increased insights into the mechanism by which these glycans may contribute to bNAb binding and neutralization dynamics. While this initial screen focused on a number of commercially available envelope proteins produced in 293T cells (similar to virus like particles), future analysis may include larger numbers of viral envelopes included in neutralization panels may provide greater resolution on the role of specific glycans in tuning neutralization activity.

Moreover, other embodiments using proteins produced in different cell lines may be incorporated into the disclosed systems and methods, including traditional antigen production cell lines linked to site specific glycan structure analysis may provide an additional layer of resolution of glycan dependent changes in antigenicity. Examples of suitable cell lines include, but are not limited to Chinese hamster ovary (CHO), various COS cell lines, HeLa cells, L cells, multiple myeloma cell lines, C127, 3T3 and BHK cell lines.

While one example utilized bNAb antigenicity glycan-fingerprints to improve the antigenic profiles of HIV envelope immunogens, mounting evidence points to a critical role of optimized antigen engineering to trigger the germline ancestors of these bNAbs, as well as their intermediate mutated ancestors (Dosenovic et al., 2015; Jardine et al., 2015), to accelerate the evolution of protective humoral immunity against HIV. Interestingly, efforts at protein engineering a germline-targeting gp120 outer domain immunogen have shown to activate germline and mature VRC01-calss B cells (Jardine et al., 2013). However, more importantly, deletion of conformationally restrictive glycans have been shown to permit the activation of germline-reverted B cell receptor (BCR) expressing B cells (McGuire et al., 2014; McGuire et al., 2013). Thus future studies that can adapt the antigenicity fingerprinting screen for the use of germline reverted BCR expressing cell lines may provide the first clues on antigenic improvements that may be generated to enhance germline low affinity interactions (McGuire et al., 2014).

This study integrated both probabilistics and a machine learning regression algorithm. The probabilistic model was designed to both cope with the heterogeneity in the glycosylation and ELISA-based fingerprinting data. Conversely, the regression model implemented kernels to account for mutual dependencies of multiple glycans, such as cooperatively supporting a conserved structure or the steric hindrance from spatial-localized glycans, contributing to bNAb fingerprints.

Additionally, a Bayesian MCMC with Metropolis-Hastings algorithm was also introduced to reduce computing time and mathematically to assure the identification of all objective solutions during immunogen design. While in some examples only glycan occupancy and gp120 sequences were used to train the regression model, the program's flexibility enables the rapid integration of additional experimental results, including glycan structure, neutralization profiles, affinity measurements, etc., that may aide in improving the accuracy and quality of the designed immunogens. Yet, even in the absence of crystal structure data or mutagenesis analysis profiles, the unsupervised model provided critical resolution on previously defined bNAb-glycan footprints. Thus with additional data, this approach is likely to accelerate the process of defining bNAb epitopes, vital fingerprints, as well as in developing novel classes of antigenically improved immunogens that may drive protective humeral immune responses.

Accordingly, the disclosed systems and methods are the first link the complex relationship between glycan occupancy and bNAb antigenicity. Using this unique dataset, bNAb-dependent glycan determinants were defined and used to engineer novel immunogens that could enhance, knock down, or selectively improve the antigenic profile of novel immunogens. Algorithms may be applied in germline BCR-expressing B cell screens to engineer immunogens able to recruit and/or reprogram the earliest B cell responses to skew antibody maturation in sequential immunization strategies. Additionally, knowledge of individual bNAb/glycan fingerprints may provide the blue-print for the design a "multivalent vaccine", able to elicit multiple lineages of bNAbs from a single super immunogen. Alternatively, the identification of undesirable non-neutralizing antibody binding profiles, that may mark immunodominant regions of the viral envelope that have limited impact on viral infectivity, can be selectively masked. Moreover, linked to structural analyses, optimized glycan occupancy profiles may be defined that can improve the quality and stability of the viral envelope, ultimately leading the production of HIV envelope immunogens with unique antigenic profiles. Finally, due to the inherent flexibility of glycan fingerprinting algorithm, this approach is highly tractable for the design of immunogens for other glycoprotein antigens beyond HIV, including hepatitis C, Ebola virus, influenza, and beyond.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A depicts a matrix of N-linked glycosylation site-specific glycan occupancy. The frequency of detected glycans by mass spectrometry was colored by a yellow-black gradient covering entire potential glycosylation sites as columns across 98 of gp120 variants as rows. The gray grids presented no detected consensus sequon from alignment. FIG. 1B depicts a bar graph of the frequency of identified consensus sequons from multiple alignment. FIG. 1C depicts a bar graph of the mean and its s.d. of detected glycan occupancy across all strains given the glycosylation sites. FIG. 1D depicts a scatter graph of the correlation of sequon frequency versus averaged glycan occupancy for each site. FIG. 1E depicts a scatter graph of the characterization of each glycosylation site by sequon frequency and glycan occupancy variance. Only the sites with high sequon frequency or occupancy variance were annotated;

FIGS. 2A-2D depict the association of glycan occupancy with bNAbs fingerprints. FIG. 2A depicts a graph of the antigenicity-based fingerprints of 13 bNAbs across 98 of gp120 variants. The normalized ELISA signals were colored in a gradient. FIGS. 2B and 2C depict graphs showing the comparison and correlation of bNAb breadth calculated from neutralization and antigenicity assays. FIG. 2D depicts a graph showing an antibody-antibody antigenicity-correlation matrix. The antigenicity was used to define the correlation matrix, where the paired correlation results were shown in heat map and were used to cluster 13 of bNAbs. The bars on the side indicated prior defined antibody families;

FIG. 3A depicts a graph showing the covariance profile between PGT121-family fingerprints and the critical glycan N332. The fingerprints together with the occupancy as well as absence/presence of the sequon were ranked in order of PGT121 signals. FIG. 3B depicts a graph showing the evaluation of model predictions given just, the absence/presence of the sequon (i), N332 glycan occupancy (ii), and all glycan occupancy (iii) as the predictors. FIG. 3C depicts a graph showing the paired correlations of bNAb fingerprint and individual glycan occupancy were calculated and showed in the heat map matrix. The values of correlation coefficient were colored as a red-blue gradient;

FIG. 4A depicts a graph showing the delineation of bNAb-specific glycan determinants individually contributing to bNAb interactions. The heat map with directional weight was showed, where the gradients indicated the probability of the importance of the site for antibody interactions, and the purple/green colors meant the modulation function as agonism/antagonism. Only the glycans showing significance (p>0.01) by comparing to the background distributions were colored in the heat map as the glycan determinants. FIG. 4B depicts a graph showing glycan determinants specific to PGT122, PGT128 and VRCO1 mapping on gp120 monomer structure. FIG. 4C depicts a bar graph showing the total contributions from agonistic and antagonistic glycans to different bNAb recognition. FIG. 4D depicts a graph showing the total contributions to VRCO1 and PGT122 recognitions were broken into each variable loop and constant regions. FIG. 4E depicts a graph showing a mapping of PGT122 agonistic and antagonistic glycan determinants colored as dark purple and green on a previous reported co-crystal structure of Env protein (BG505 SOSIP.664) and PGT122;

FIG. 5A depicts a graph showing the signature of agonistic and antagonistic glycan determinants specific to PGT121 and PGT128 as the upper panel, five immunogens by manipulating the sequons of those glycan determinants as the middle panel. The boxes colored as yellow and black indicated the absence and presence of the glycosylation sequons, respectively. FIGS. 5B and 5C depict graphs showing the comparison of predicted and measured binding activities from five engineered immunogens and wild-type gp120 against PGT121 and PGT128. FIGS. 5D and 5E depict the correlation of PGT121 (d) and PGT128 (e) binding activity from prediction and measurement;

DETAILED DESCRIPTION

Figure 1A:
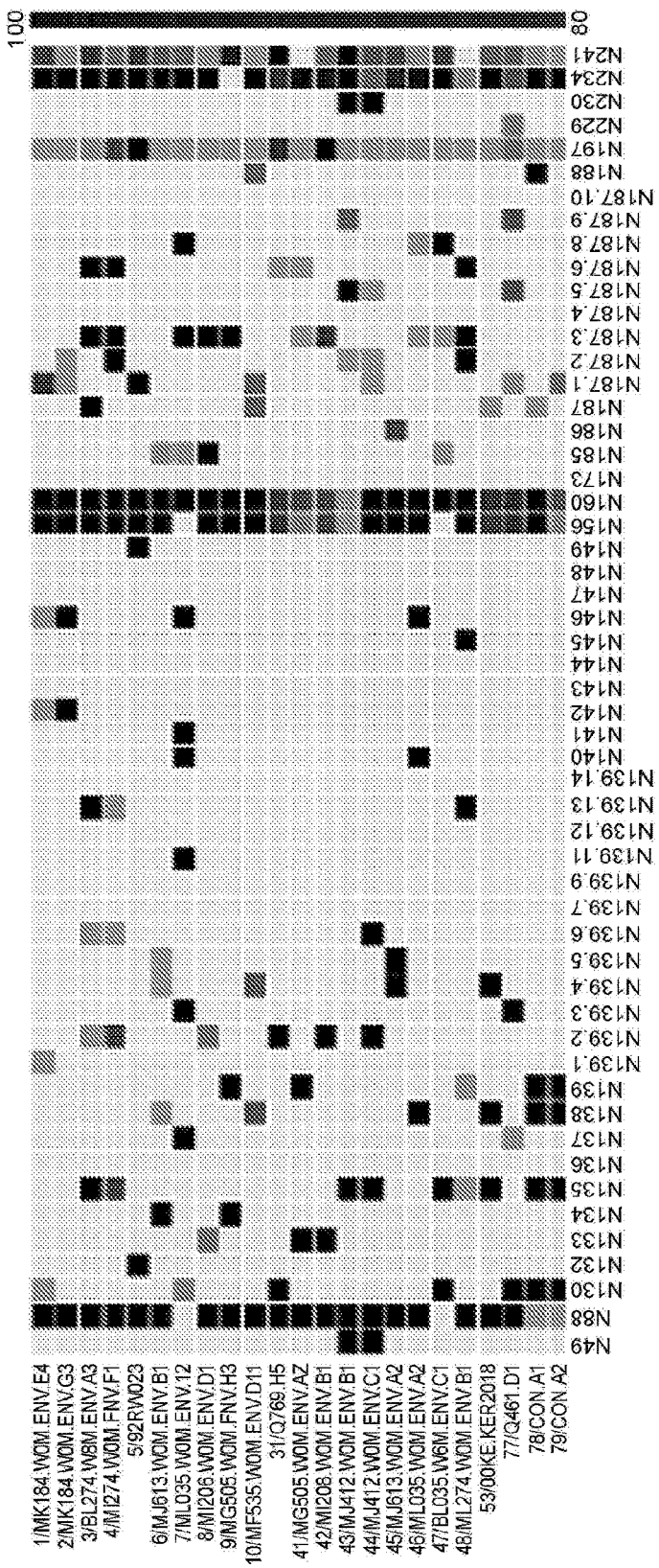
FIGS. 1A-1E depict, in accordance with various embodiments of the present invention, a comprehensive identification of global gp120 glycans across HIV strains.
Figure 1A:
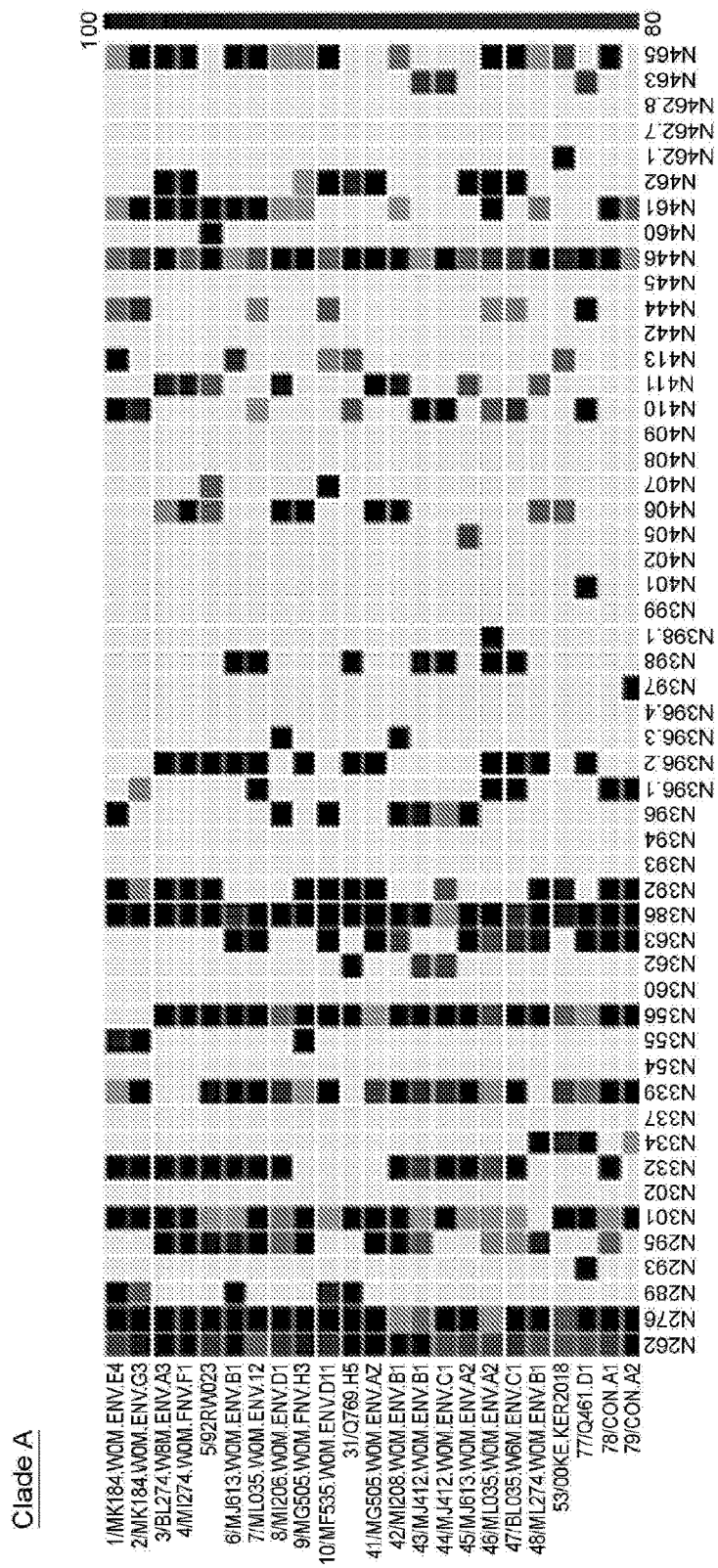

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

Some viruses have viral envelopes covering their protein capsids. The envelope is made from phospholipids and proteins (derived from portions of the host cell membranes) and some include viral glycoproteins. Glycoproteins on the surface of the envelope serve to identify and bind to receptor sites on the host's membrane that are also cell surface glycans. The viral envelope then fuses with the host's membrane, allowing the capsid and viral genome to enter and infect the host.

Antibodies that bind to viruses and neutralize them also primarily bind to the glycoproteins on the viral envelope. Additionally, the glycoproteins contain asparagine (N)-linked glycosylation sites where glycans, or complex branched-chain carbohydrate structures, are fused to the glycoprotein. For instance, HIV-1 glycoprotein 120 (gp120) contains 25 sites for N-linked glycosylation. The disappointing results of the first phase 3 trial of a candidate AIDS vaccine, AIDSVAX, based on the gp120 viral envelope glycoprotein, highlights how difficult it is to generate a protective antibody response against HIV-1.

However, a few types of antibodies can bind to most different mutants or variants of the viral envelope called broadly neutralizing antibodies (nNAbs). In some patients, these develop over long periods of time in natural selection for antibodies. However, they take too long to develop and they do not have optimal affinity for all variants of HIV-1.

An immunogen is an antigen or any substance that may be bound by components of the immune systems, for instance antibodies that elicit an immune response. Antibodies are secreted by B cells of the adaptive immune system, mostly by differentiated B cells called plasma cells. Antibodies are created when B cells ingest antigens (such as immunogens) and then create antibodies that have affinity for the immunogen. In some examples, an immunogen may include the components of the viral envelopes of viruses that contain glycans connected to glycosylation sites.

Accordingly, this process can be harnessed to synthesize antibodies or immunogens useful for treating a viral infection. For instance, if synthetic immunogens are manufactured (synthetic copies of the viral envelope) they can be harmlessly introduced to a patient, so their immune system may form antibodies and other long term immunity. In other examples, antibodies may be synthesized that can be administered to the patient.

Additionally, the removal or addition of specific glycosylation sites can dramatically increase or decrease viral affinity for neutralizing antibodies—and potentially any synthetic antibody treatment or immunogen vaccine. However, current research is limited to modifying a few localized glycosylation sites, and has not explored manipulating the entire glycan structure of a viral envelope, or co-dependency of glycosylation sites and their glycan occupancy.

The synthesized immunogen and/or antibodies of the invention are useful in a variety of applications including, but not limited to, therapeutic treatment methods, such as the treatment of viral infections, bacterial infections, parasitic infections and cancer/tumors. Examples of viral infections include, but are not limited to, Human Immunodeficiency Virus (HIV), Herpes Simplex Virus (HSV), Epstein-Barr Virus (EBV), Cytomegalovirus (CMV), Herpes Simplex, Influenza (flu), Ebola Virus Disease (EVD)/Ebola hemorrhagic fever (EHF), and Hepatitis C. Examples of bacterial infections include, but are not limited to, Tuberculosis (TB), Strep Throat, Meningitis and Pneumonia. Examples of parasitic infections include, but are not limited to, Malaria, Amoebiasis, Giardiasis, Leishmaniasis, and Toxoplasmosis.

Examples of cancer include, but are not limited to, ovarian cancer, pancreatic cancer and prostate cancer.

Terms such as "treating" or "treatment" or "to treat" or "alleviating" or "to alleviate" refer to therapeutic treatment and/or prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

The term "subject" refers to any animal (e.g., a mammal), including, but not limited to humans, non-human primates, rodents, and domestic and game animals, which is to be the recipient of a particular treatment. Primates include chimpanzees, cynomologous monkeys, spider monkeys, and macaques, e.g., Rhesus. Rodents include mice, rats, woodchucks, ferrets, rabbits and hamsters. Typically, the terms "subject" and "patient" are used interchangeably herein in reference to a human subject. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition.

The term "therapeutically effective amount" refers to an amount of an antibody, polypeptide, polynucleotide, small organic molecule, or other drug effective to "treat" a disease or disorder in a subject or mammal. The therapeutically effective amount of the drug can reduce the severity of the disease symptoms, including HIV symptoms. These include, but are not limited to, diarrhea, fever, fatigue, abdominal pain, abdominal cramping, inflammation, nausea, vomiting, reduced appetite, and weight loss.

The methods of use may be in vitro, ex vivo, or in vivo methods. In certain embodiments, the disease treated with the synthesized immunogen and/or antibodies is HIV.

In various embodiments, the synthesized immunogen and/or antibodies according to the invention may be formulated for delivery via any route of administration. "Route of administration" may refer to any administration pathway known in the art, including but not limited to, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the synthesized immunogen and/or antibodies can be in the form of tablets, gel capsules, sugar-coated tablets, syrups, suspensions, solutions, powders, granules, emulsions, microspheres or nanospheres or lipid vesicles or polymer vesicles allowing controlled release.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. In particular embodiments, compounds used herein are administered orally, intravenously or intramuscularly to a patient.

In various embodiments, the antibody is a monoclonal antibody, human antibody, humanized antibody or a neutralizing antibody. The synthesized antibodies can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides the synthesized antibodies including a pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions.

Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

In some embodiments, the present invention provides the immunogen including a protein carrier and/or an immunological adjuvant. Examples of carrier proteins include, but are not limited to, Keyhole Limpet Hemocyanin (KLH), Concholepas Concholepas Hemocyanin (CCH), Blue Carrier Immunogenic Protein, Bovine Serum Albumin (BSA) cationized BSA (cBSA), and/or Ovalbumin (OVA). Examples of immunological adjuvants include, but are not limited to, Complete Freund's adjuvant, Incomplete Freund's adjuvant and solutions of aluminum hydroxide or aluminum phosphate. In some embodiments, the immunogen and the protein carrier are administered. In other embodiments, the immunogen and the immunological adjucant is administered. In yet other embodiments, the immunogen, the protein carrier and an immunological adjuvant are administered.

The synthesized immunogen and/or antibodies according to the invention may be delivered in a therapeutically effective amount. The precise therapeutically effective amount is that amount of the synthesized immunogen and/or antibodies that will yield the most effective results in terms of efficacy of treatment in a given subject. The therapeutically effective amount of synthesized immunogen will induce an immune response in the subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

For the treatment of the disease, the appropriate effective amount of the synthesized immunogen and/or antibodies depends on the type of disease to be treated, the severity and course of the disease, the responsiveness of the disease, whether the synthesized immunogen and/or antibodies are administered for therapeutic or preventative purposes, previous therapy, and patient's clinical history. The dosage can also be adjusted by one of skill in the art in the event of any complication and at the discretion of a person skilled in the art. The person skilled in the art can determine optimum dosages, dosing methodologies and repetition rates. The synthesized immunogen and/or antibodies can be administered one time or over a series of treatments lasting from several days to several months, or until a cure is effected or a diminution of the disease state is achieved (e.g., treatment or amelioration of the disease). The duration of treatment depends upon the subject's clinical progress and responsiveness to therapy. In certain embodiments, dosage is from 0.01 µg to 100 mg per kg of body weight, and can be given once or more daily, weekly, monthly or yearly. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In various other embodiments, the synthesized immunogen and/or antibodies are administered in a series of treatments. In selected embodiments, the synthesized immunogen and/or antibodies will be administered to patients that have previously undergone a treatment. In some embodiments, the treatment is administered in any order, including prior to, concurrently with, substantially simultaneously or subsequent the administration of a second treatment.

Using the systems and methods disclosed herein, the inventors have discovered that glycan occupancy rates impact and predict the glycosylation sites and corresponding glycans that are determinant of binding affinity for certain antibodies. Accordingly, various algorithms, for example machine learning algorithms, were developed that analyze occupancy rates and various binding affinities for an antibody across variants of specific viral glycoproteins. These algorithms have identified glycosylation sites and corresponding glycans that are determinant (either agonistic or antagonistic) to binding affinity for the antibody.

In one example, systems and methods disclosed herein have analyzed the glycan heterogeneity and how this heterogeneity impacted bNAb binding in HIV-1 glycoprotein 120. Because gp120 glycosylation was remarkably variable, unique glycan-dependent bNAb glycan-binding footprints were observed, directed by both agonistic and antagonistic glycans that cooperatively facilitate antibody recognition. Moreover, these footprints offered a unique opportunity to engineer gp120 immunogens that were able to selectively improve bNAb-specific antigenicity, offering a means by which novel classes of antigenically enhanced immunogens may be engineered.

Mass spectrometry-based glycoproteomics was performed to define glycan occupancy across the gp120 proteome isolated from 94 distinct HIV viral isolates. Remarkably, highly diverse glycan occupancy profiles were observed at most potential N-linked glycosylation sites, including sites known to be targeted by bNAbs. Using an unsupervised probabilistic machine learning algorithm, bNAb-specific glycan footprints, composed of both agonistic and antagonistic N-linked glycan determinants on gp120, were identified. Moreover, these footprints were utilized to design glycan-optimized immunogens, which were able to selectively improve or alter PGT121 and PGT128 bNAb antigenicity.

This approach provides systems and methods that can be utilized to engineer and synthesizes immunogens (and/or antibodies) that have increased affinity for many different mutants of HIV and other viruses. Accordingly, these systems and methods may be utilized to produce incredibly robust treatments, such as, synthetic vaccines or antibody treatments for HIV and other viruses for instance to glycan-dependent bNAbs, via selective glycosylation profiles tailored to enhance bNAb binding. These systems and methods can also be utilized to 1) identify how and/or where antibodies bind to a target antigen/immunogen; 2) identify how glycosylation may impact antibody interactions; and/or 3) create binding antigens to select antigen-specific memory B cells to particular antigen-determinant for monoclonal library generation.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Glycosylation Heterogeneity Across HIV Gp120 Strains

Traditional approaches at assessing the degree of HIV envelope glycosylation have relied on the enumeration of putative sequons, or potential N-linked glycosylation sites (PNGs), within a protein. However, accumulating data suggests that the presence of a sequon is necessary, but not sufficient, to guarantee the presence of a glycan (Go et al., 2011). Thus the inventors conducted a large-scale mass-spectrometry-based glycoproteomic analysis of glycan-occupancy profiles across 94-gp120 recombinant envelope proteins spanning Clades A, B, C, and a few AE, AG and BC variants. Specifically, carbohydrate occupancy was defined following enzymatic digestion, deglycosylation, occupied-site labeling, and MS/MS fragment quantification and site-mapping. Strikingly, glycan occupancy showed unexpected high degrees of discrepancies at most of PNGSs (FIG. 1A) with ~75% of detected sequons occupied only by partial or no glycans (Table 1). These data highlight for the first time the dynamic nature of sequon glycosylation that is not solely dictated by the presence of a sequon in the protein sequence.

TABLE 1

The Fisher's exact test of two modeling predictions

| | Identified | Not yet Identified | Total | p-value |
|---|---|---|---|---|
| Occupancy Model | | | | |
| Model prediction | 27 | 266 | 293 | |
| References | 41 | 1324 | 1365 | |
| | | | | 9.97e−06 |
| Consensus sequon Model | | | | |
| Model prediction | 18 | 313 | 331 | |
| References | 41 | 1324 | 1365 | |
| | | | | 0.03 |

Figure 1B:
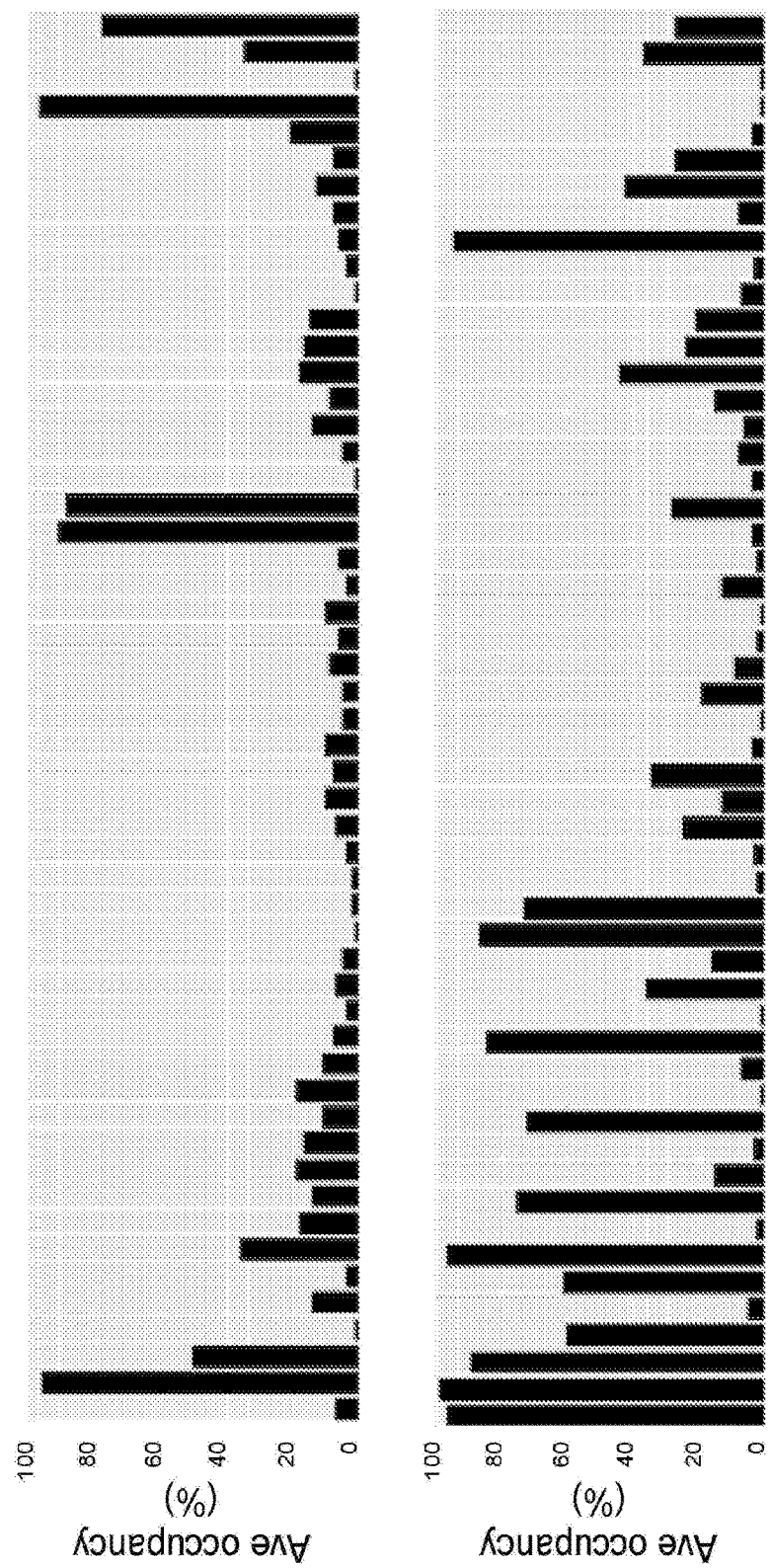
Figure 1C:
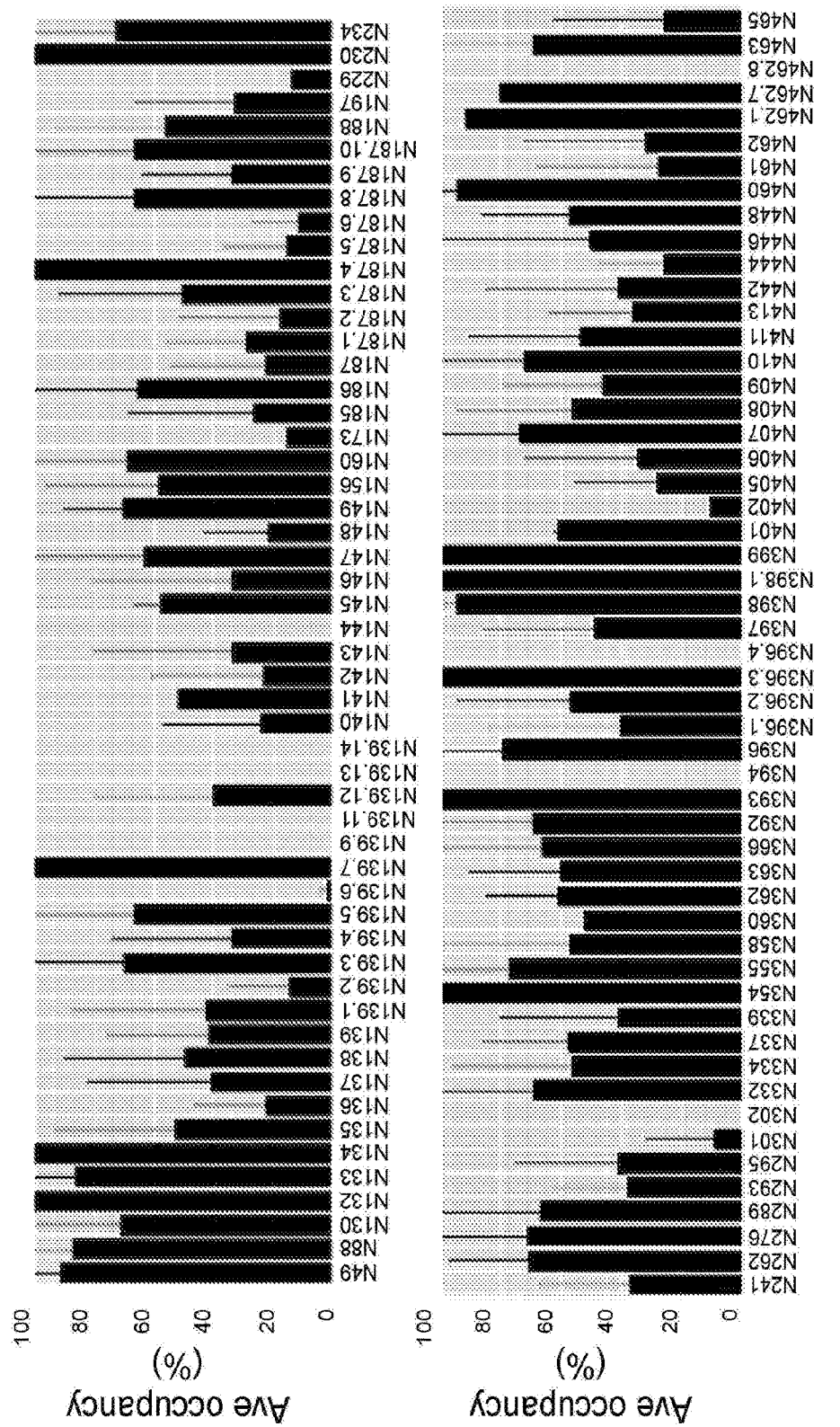
Figures 1D, 1E:
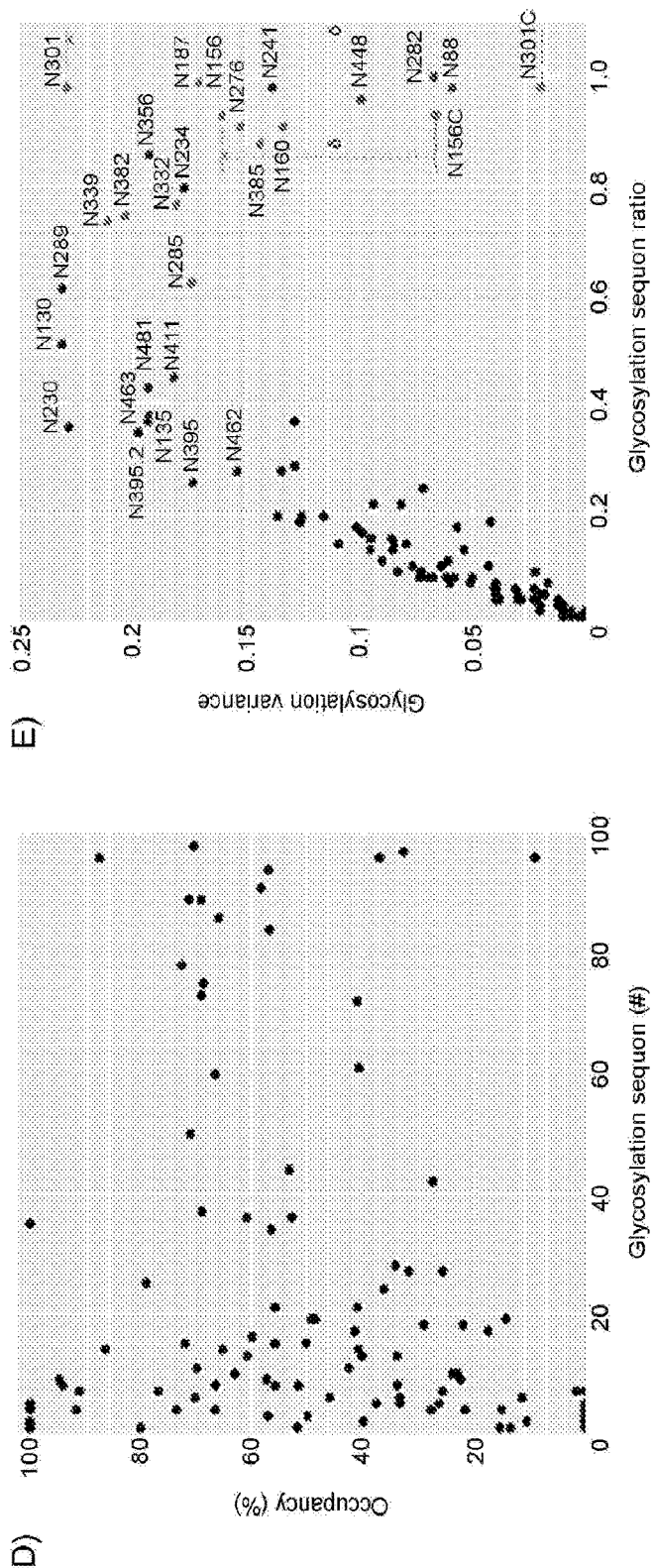

Next, to investigate the nature of glycosylation variability, the inventors examined the relationship between the frequency of a given sequon in all gp120 sequences and its likelihood of being occupied (FIGS. 1B and C). Unexpectedly, no correlation was observed between sequon conservation (sequon frequency) and glycan occupancy (FIG. 1D). Thus, highly conserved PNGSs were not the most likely to be glycosylated, such as N197 and N30. Instead, less conserved PNGSs, that appeared only infrequently across gp120 isolates, were nearly always glycosylated, such as N49. Thus, these data suggest that the consensus sequon (N-X-S/T) cannot solely predict gp120 glycosylation, which may be impacted by spatial occlusion by highly compacted glycans as well as stochastic glycosylation processes (Lau et al., 2007).

To further scrutinize whether the degree of heterogeneity in glycan occupancy was related to evolutionary or immune pressure, the inventors compared sequon conservation (sequon frequency) for each PNGS and its glycan occupancy variance (FIG. 1E). While no overall correlation was observed, a subset of highly conserved PNGSs, such as N88, N262 and N448, (FIG. 1E, green spots) showed relatively low variance in glycan occupancy, suggesting that these glycans are indispensable to HIV potentially for folding/functions, consistent with the reports showing that deletions of N262 or N448 resulted in significantly decreased viral infectiousness (Francois and Balzarini, 2011).

Interestingly, most reported PNGSs that participate in bNAb binding fell among the sequons that were highly conserved, but exhibited less conserved in glycan occupancy (FIG. 1E, spots), such as N332 and N301, suggesting that the glycan heterogeneity on these critical PNGSs did not influence bNAb recognition in which bNAb specifically utilize those glycans as the sites of vulnerability. This flexibility in single site evolution and/or lack of glycosylation at N332 may be linked to the capacity of PGT antibodies to utilize other proximal glycans including N295 and N334 (Sok et al., 2014). This cooperativity between multiple glycans highlights the necessary to define the overall landscape of PNGs cooperative binding to provide a more accurate appreciation of the specific glycans involved in bNAb binding.

Figure 2A:
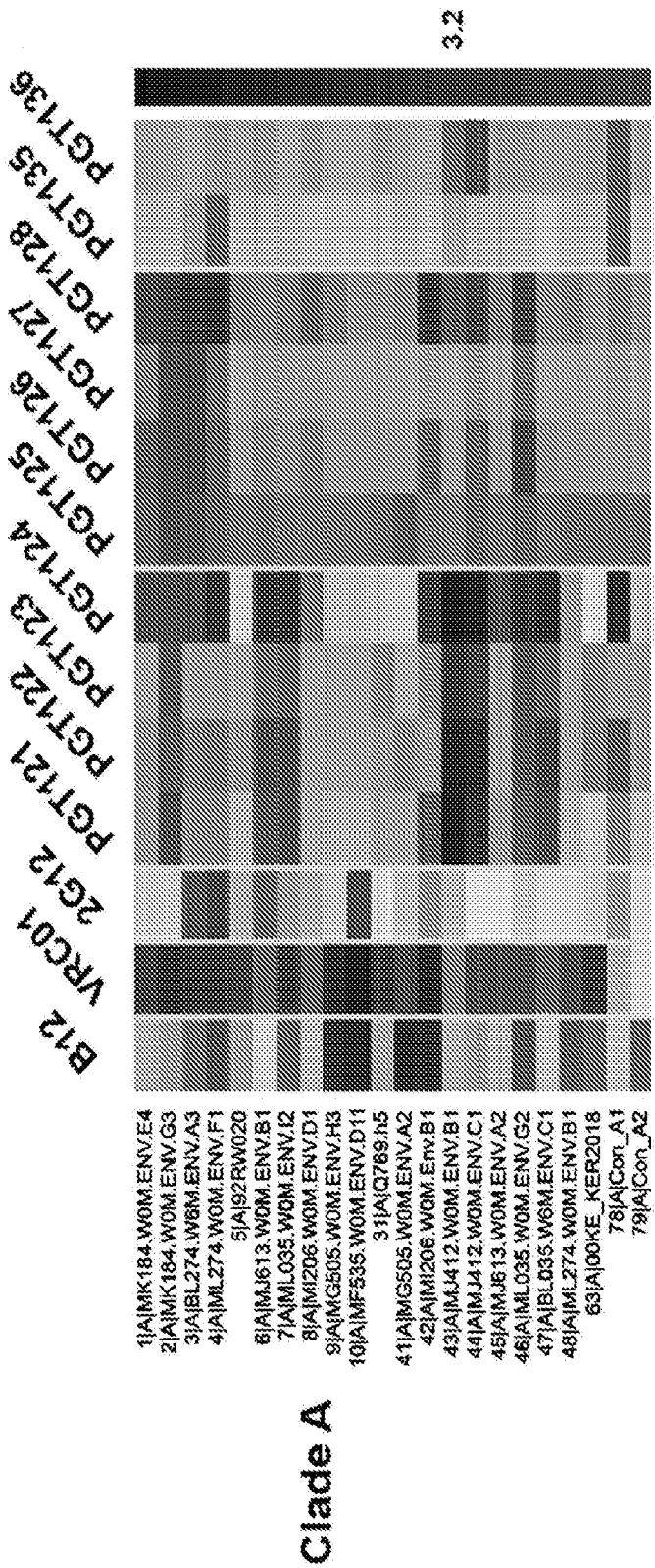
Figure 6:
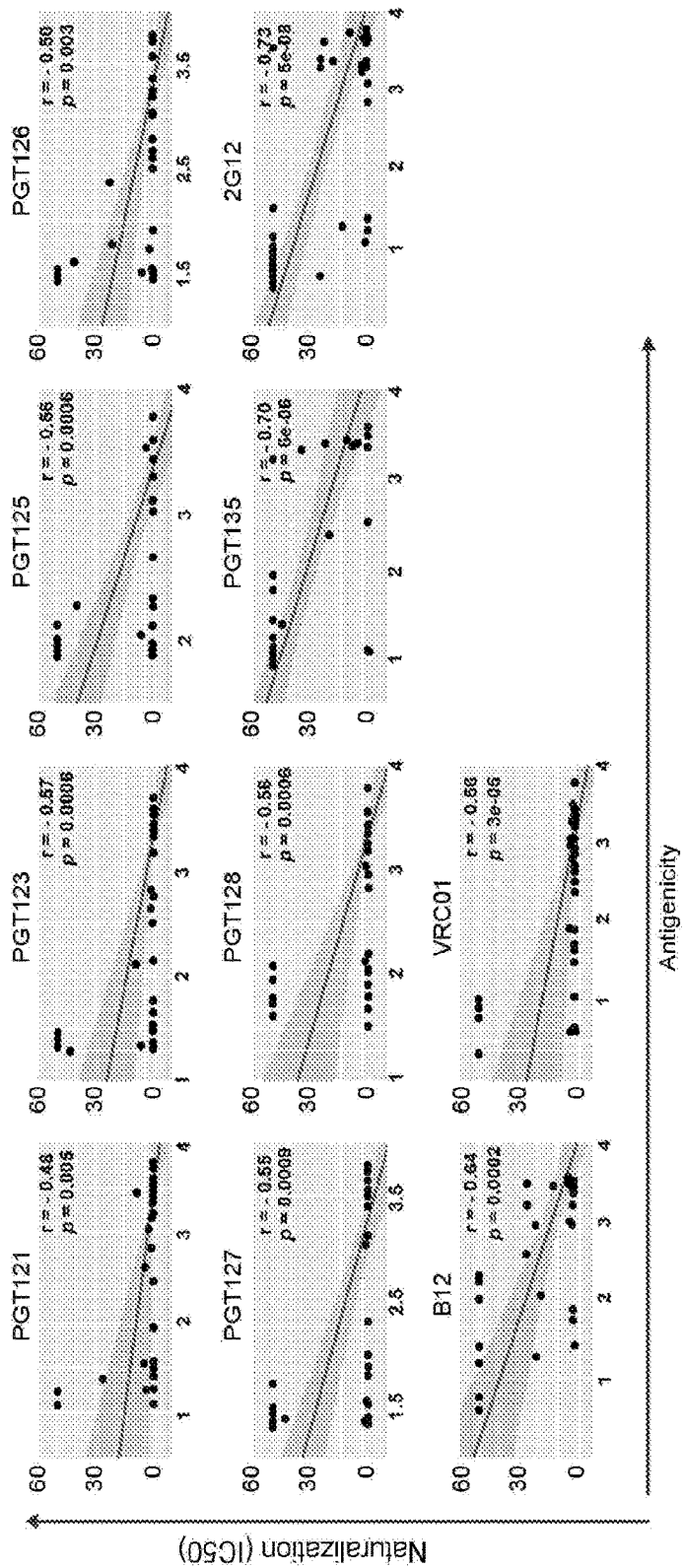
FIG. 6

Example 2: Shared bNAb Family Binding Fingerprints can be Defined and Relate to Neutralizing Activity To next define the landscape of glycans that modulated individual bNAb binding profiles, the profiles of a panel of 13 bNAbs, that globally fell into 1 of 4 families: PGT121- (PGT121-124), PGT128- (PGT125-128), PGT135- (PGT135-136) or CD4 binding site-like (B12 and VRC01) antibodies (FIG. 2A) was assessed. Interestingly, each of the 13 antibodies exhibited a unique binding profile to the 94-protein panel (FIG. 2A). To first assess whether ELISA binding profiles relate to neutralizing activity of individual antibodies, neutralization profiles for each antibody was compared to ELISA binding signatures. First, neutralization potency was significantly negatively correlated to ELISA binding data for each bNAb (FIG. 6).

Figure 2B:
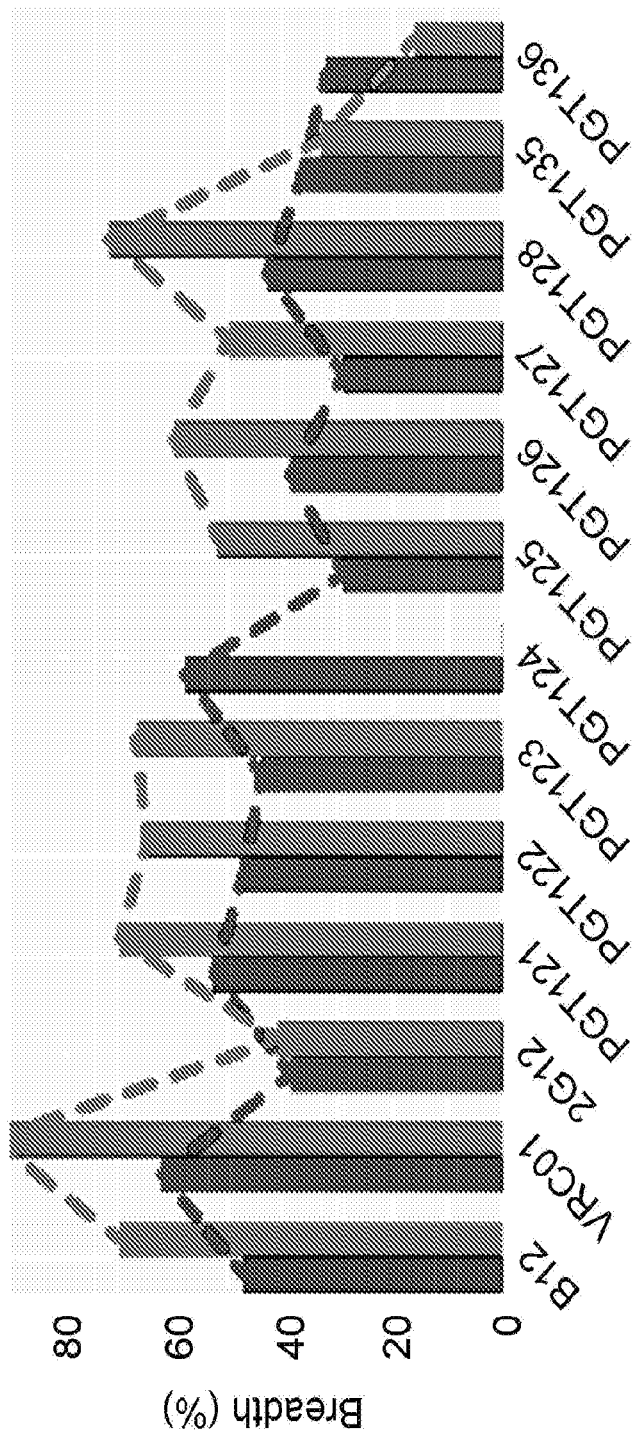

Second, bNAb breadth (Walker et al., 2011; Wu et al., 2010) and binding breadth (number of gp120 isolates bound above the average across all gp120 proteins for each antibody) exhibited similar dynamics (FIG. 2B) and were significantly positively correlated (FIG. 2C). Thus, while binding alone is not sufficient to explain neutralization, binding is required for neutralization, highlighting the critical information that may be garnered from these unique bNAb binding signatures, that relate to their neutralization activity. Moreover, because glycans are truncated during crystallography, the involvement of complete glycans in binding to bNAbs is never fully elucidated. Thus the binding fingerprints here may provide critical insights into the specific involvement of fully extended glycans and their location on bNAb interactions and activity.

To next determine whether the antigenicity-profiles could identify related bNAbs that share similar epitopes, a correlation matrix was used to cluster bNAb binding profiles, interrogating all pairwise correlations between bNAb binding fingerprints (FIG. 2D). Clearly B12 and VRC01, both of which recognize the CD4 binding site, clustered and separated from the other tested antibodies. As expected, clonally related antibodies such as PGT121-124, PGT125-128 and PGT135-136 clustered more closely within a family than between families, strongly, arguing that family members or antibodies with similar specificities exhibit more similar antigenicity fingerprints.

Example 3: Glycan Agonists/Antagonists Contribute to bNAb Recognitions

Figure 3A:
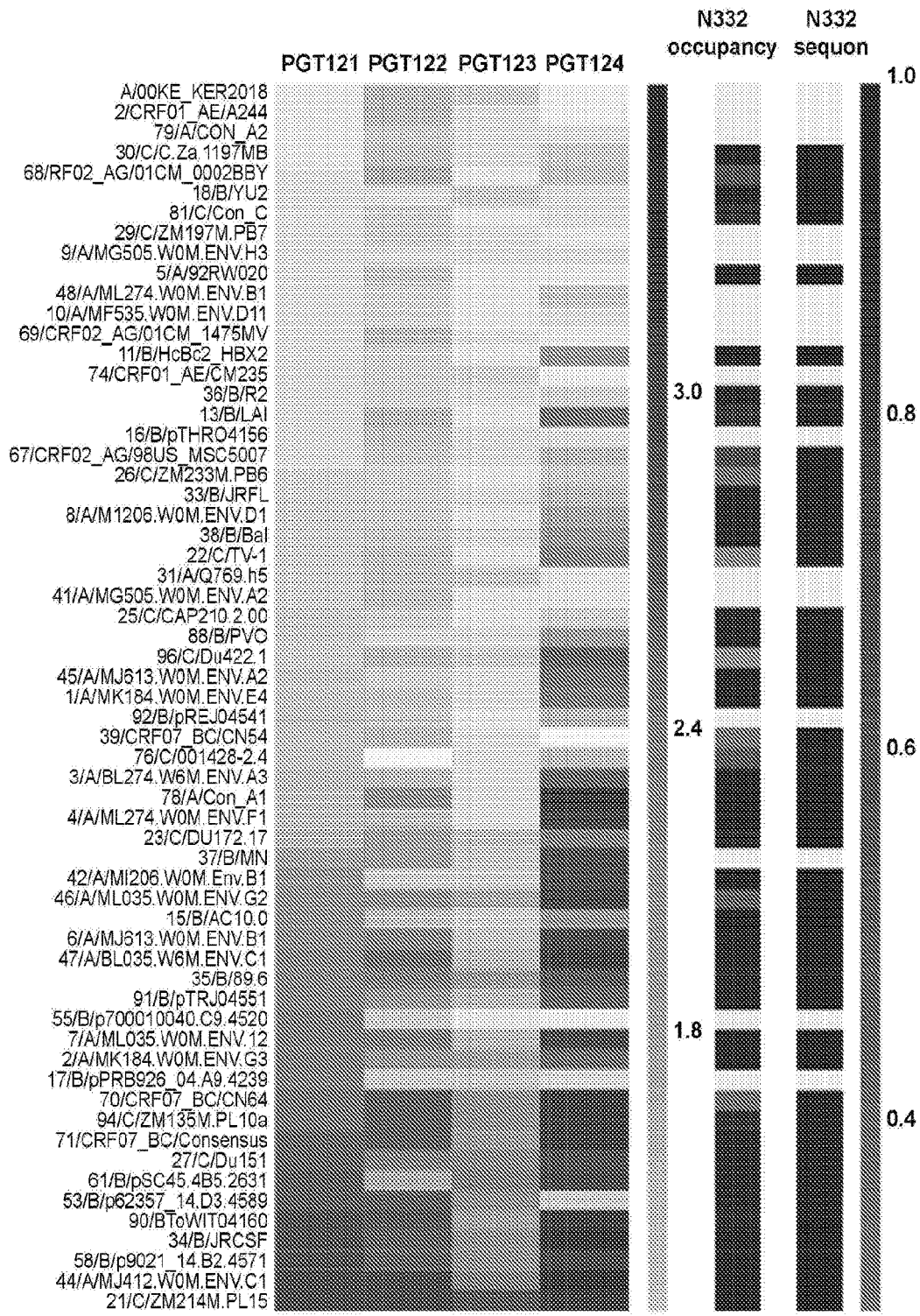
FIGS. 3A-3C depict the discovery of agonism and antagonism as the function of a single glycan modulating bNAb recognitions.
Figure 3A:
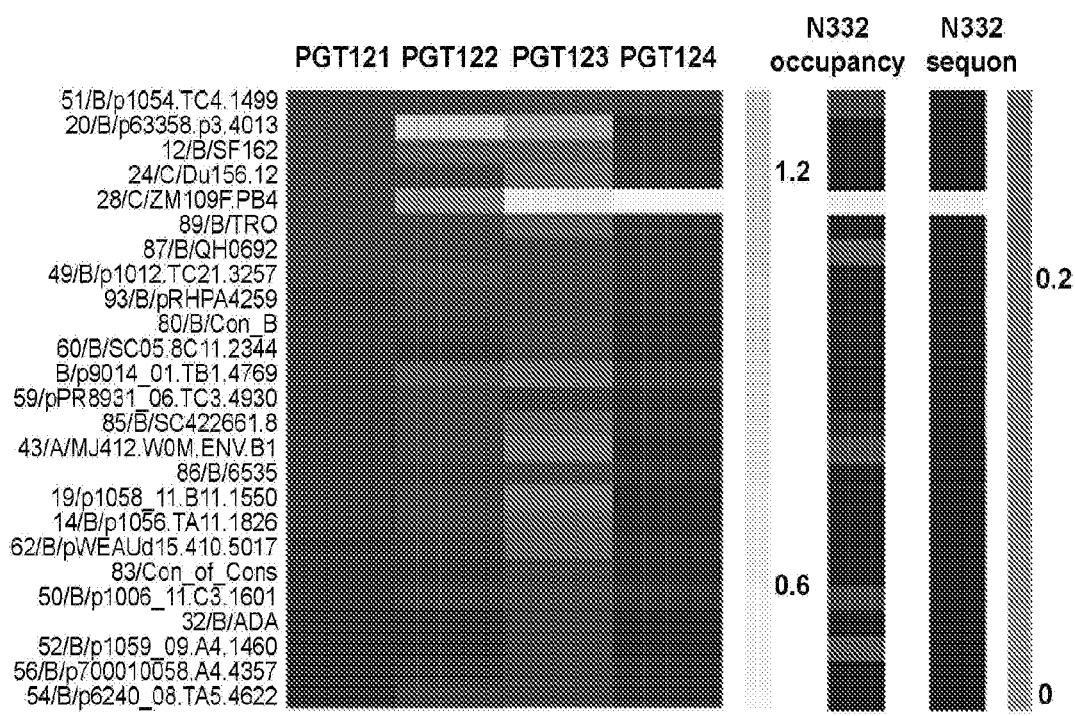

To further dissect the role of glycans in determining antigenicity-fingerprints, the inventors focused on the PGT121 profile due to its well characterized N332-dependent neutralization footprint. As expected, PGT121 shared similar binding profile characteristics with other family members (FIG. 3Ai). Interestingly, both the presence of the sequon alone (FIG. 3Aii) and the presence of the glycan (FIG. 3Aiii) scattered in the similar manner as the binding profile. However, only weak correlations were observed between the PGT121 binding profile and the predicted binding profiles utilizing either the presence of the N332 sequon (FIG. 3Bi, r=0.16) or an occupied N332 glycan (FIG. 3Bii, r=0.19) as a predictor in a regression model.

Figure 3B:
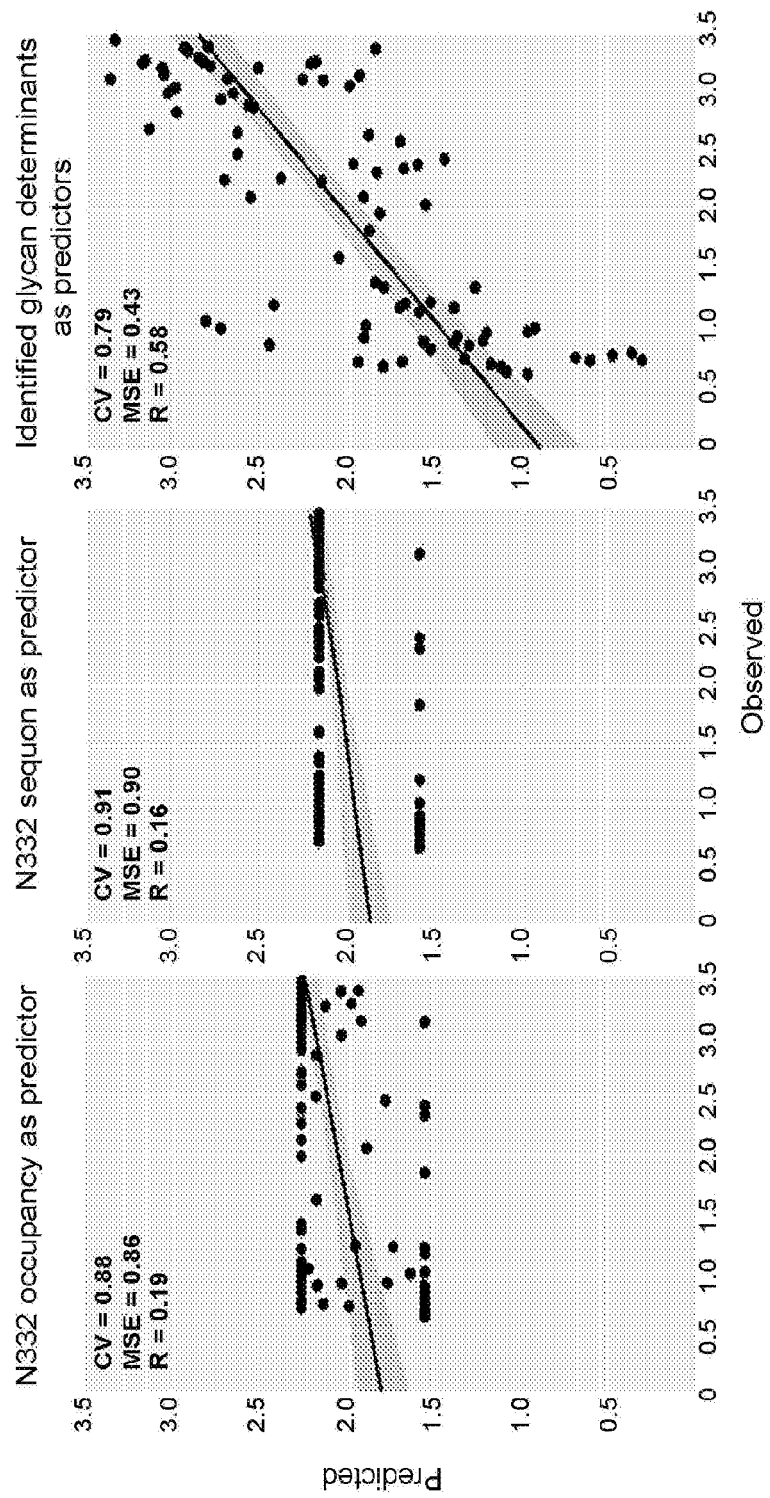
Figure 3C:
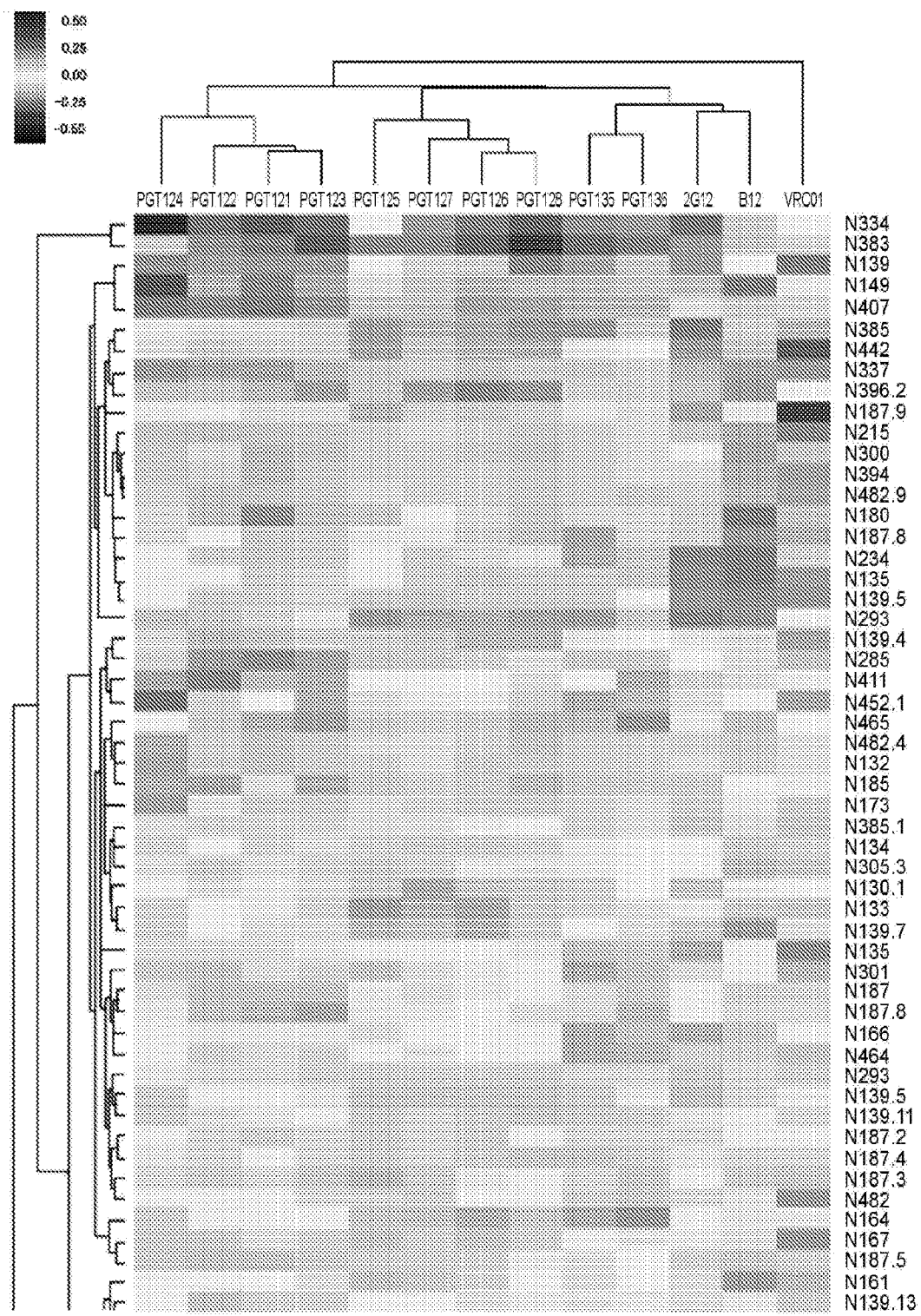

Given that PGT121 can utilize other proximal glycans for bNAb binding, it was speculated that clusters, rather than single, glycans may contribute to bNAb binding profiles. Thus a glycan-antibody covariance matrix, which characterized all pairwise glycan occupancy at individual sequons and bNAb interactions was considered (FIG. 3C, PGT121 panel). Interestingly, the covariance analysis pointed to a bimodal pattern of interactions between PGT121 and individual N-glycan sites, where glycans either agonized or antagonized antibody binding. By considering overall glycan landscape the regression model strongly predicted PGT121 binding profiles (FIG. 3Biii, r=0.91). When the same analysis was applied to all bNAb binding profiles, similar agonist/antagonist profiles were observed for each tested bNAbs (FIG. 3C). Moreover, some interesting patterns emerged in this data including, shared antagonists (N337, N354, N360, N407, N442) and agonists (N197, N397) that likely mark glycans that are structurally essential for the viral envelope, as well as known antagonists (N276 for VRC01) and agonists (N332 for PGT121s, PGT128s, PGT135s and 2G12). Given the broad array of n-glycans that fall into the agonist/anatomist categories for each bNAb, these data suggest that both proximal contact-dependent and independent glycans are likely involved in modulating bNAb binding profiles.

Example 4: A Probabilistic Machine Learning Regression Model Deconvolutes the Minimal Glycan Fingerprints of Glycan-bNAb Interactions To dissect the complexity of glycans involved in shaping bNAb binding profiles, an example of an unsupervised probabilistic machine learning regression algorithm that incorporates mutual dependence of multiple PNGSs, including both cooperative/competitive interactions, was developed. In this example, the model included: (i) a support vector regression model with incorporated kernels to uncover nonlinear relationships, and (ii) a Bayesian Markov chain Monte Carlo (MCMC) sampler which efficiently approximated the landscape of different combinatorial PNGSs contributing to bNAb recognition. Ultimately, the algorithm defined the likelihood of individual PNGS on bNAb recognition.

As expected, the model clearly highlighted similar critical glycan usage by related bNAbs (FIG. 8) consistent with the previously defined binding fingerprints (FIG. 2D), illustrating the overlapping epitope shared by these bNAbs. To further determine statistically significant glycan determinants, nominal P value of individuals was estimated by comparing to a corresponding null distribution generated from a permutation test. As expected, bNAbs within the family shared more similar glycan determinants than the others (FIG. 9), suggesting the use of similar glycans among bNAb family members, and further implying the evolution of the germline lineages during antibody affinity maturation process (Garces et al., 2014).

To define model performance, the collective impact of sequon presence and/or occupancy of 41 PNGSs that are known to directly modulate the 13 bNAb neutralization profiles, from the co-crystal and/or mutagenesis studies, was analyzed. While the model selected 27 of the 41 PNGSs (Table 1. p-value=9.97e–06, The Fisher's exact test), this unsupervised machine learning approach required no prior knowledge of the Env sequence or structure to identify the critical nature of these sites on bNAb binding profiles. In contrast, when sequon alone was utilized, in the absence of information on occupancy, fewer determinants (18 out of 41) with less statistical significance (Table 1, p-value=0.03) were selected, clearly illustrating the critical nature of occupancy data on predicting bNAb activity.

Figure 10:
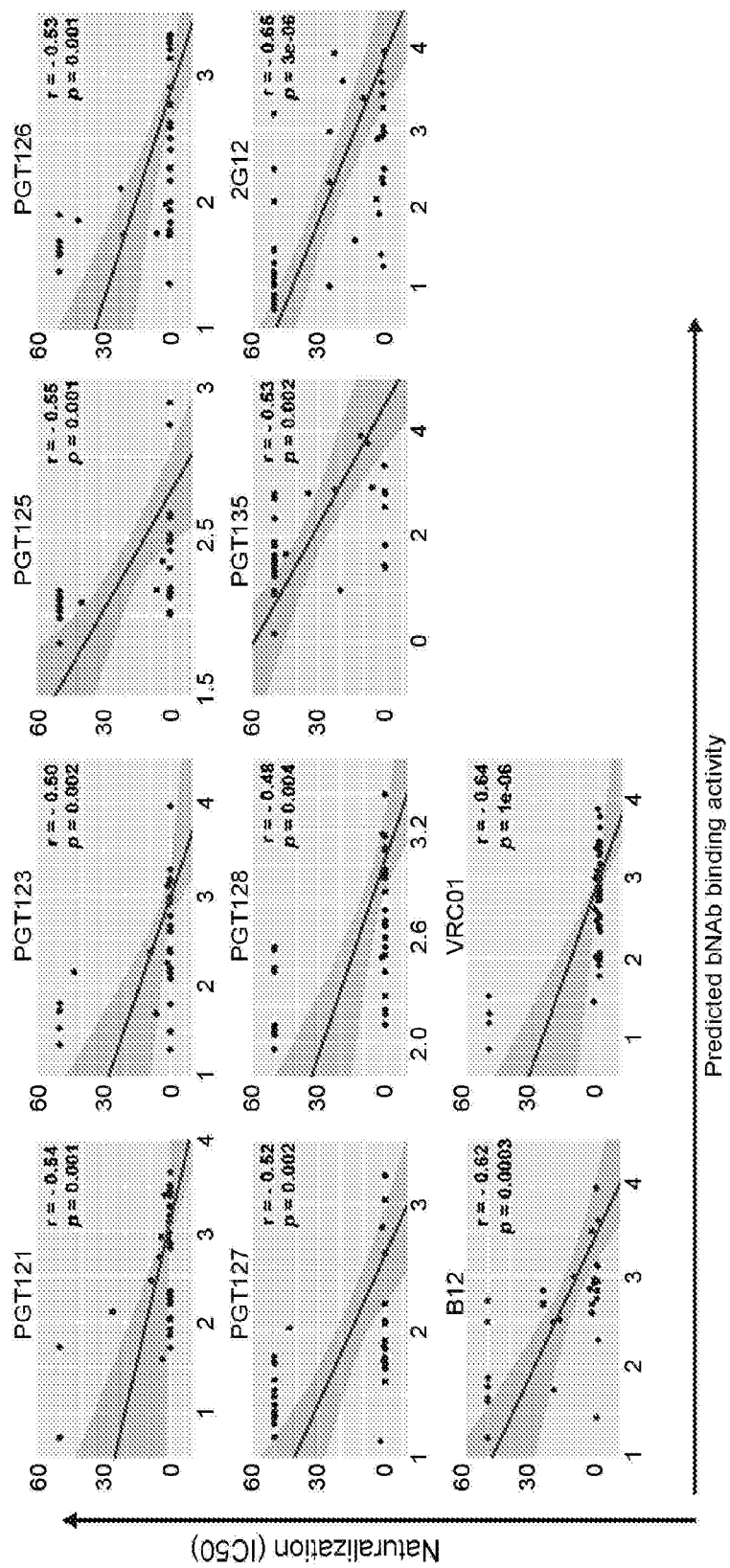

Similarly, the probabilistic regression model was utilized to predict PGT121 antigenicity, demonstrating a significant improvement in predicting PGT121 activity (FIG. 3Biii) compared to predictions using N332 alone (FIG. 3Bi or ii). Furthermore, the ability of this machine learning model to integrate and predict the neutralization activity of individual bNAbs, given a viral sequence, was assessed (FIG. 10), demonstrating significant correlations between the predicted antigenicity and their neutralization for all 10 tested bNAbs (FIG. 10). Together these results suggest that these binding fingerprints provide critical resolution on bNAb interactions with the whole envelope glycoproteome.

Figure 4A:
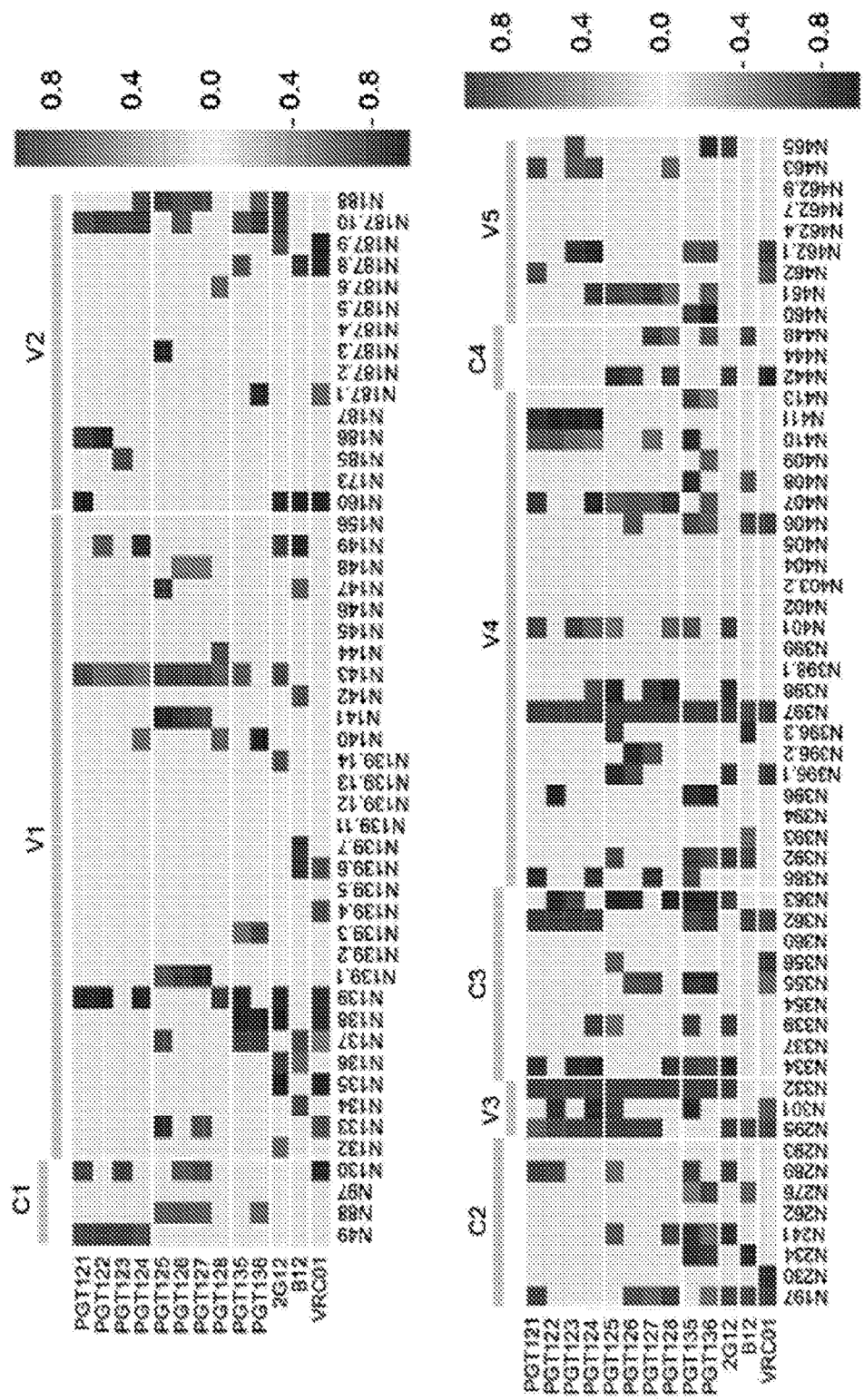
FIGS. 4A-4E depict graphs showing the identification of bNAb-specific glycan determinants and their potential functions modulating bNAb recognitions.
Figure 4B:
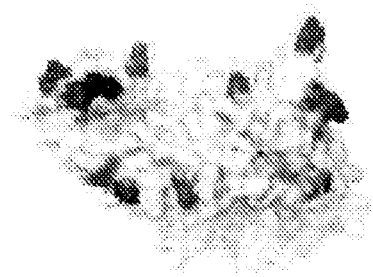
Figure 4B:
Figure 4B:
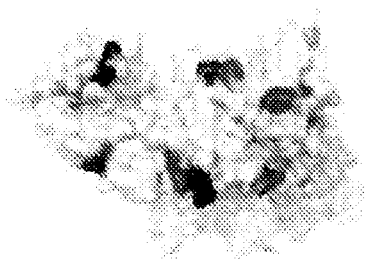
Figure 11:
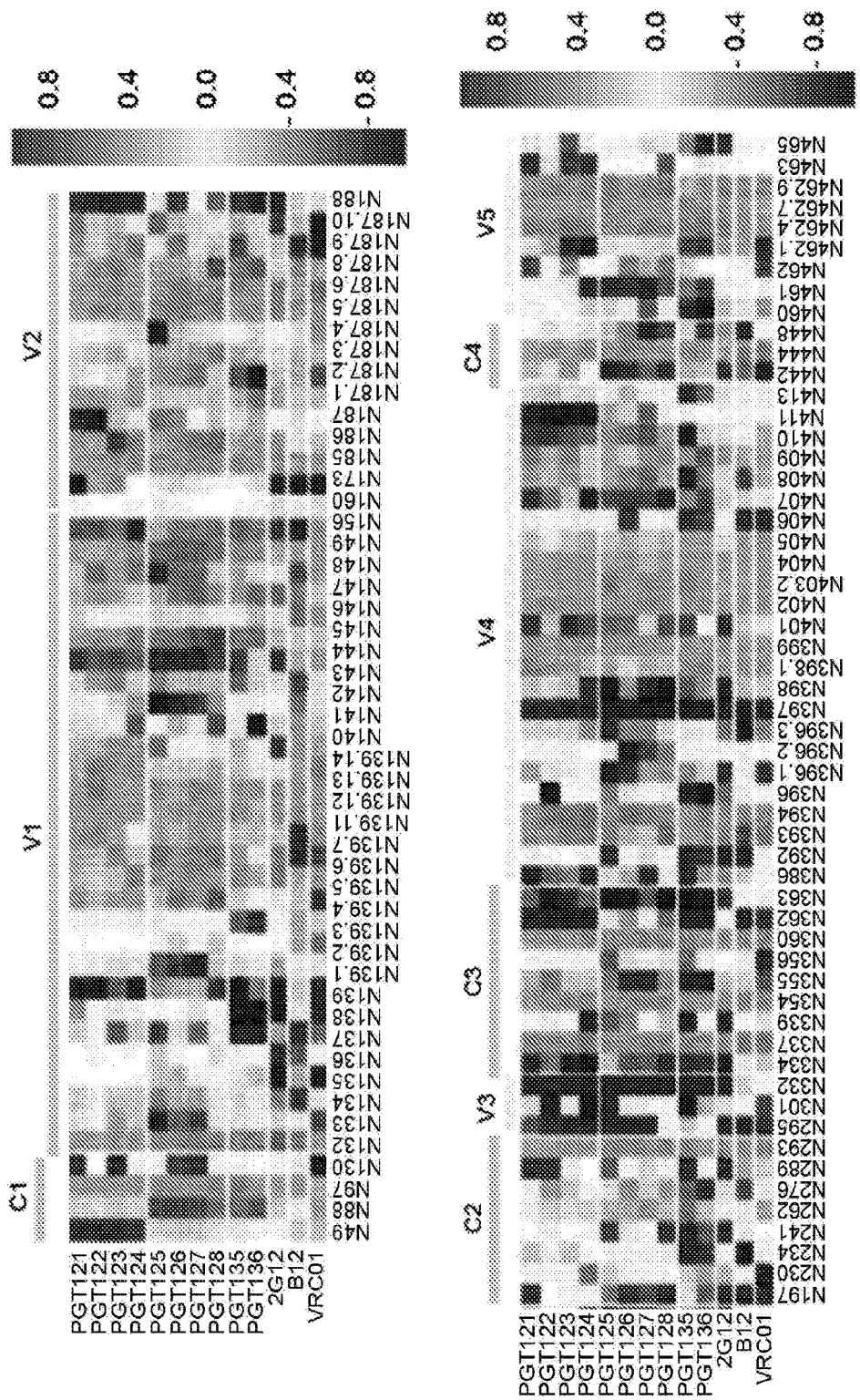
Figure 12:
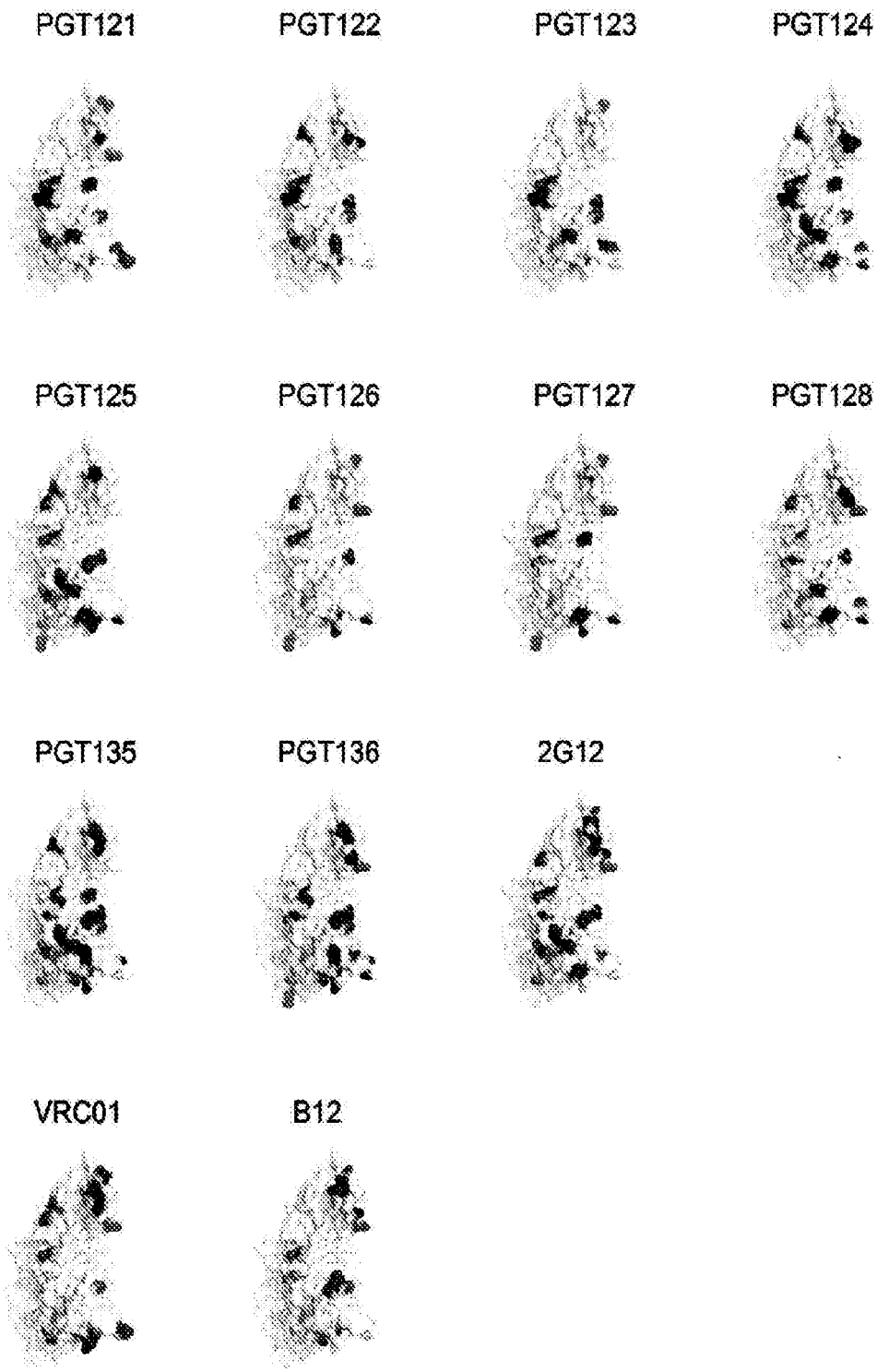
Figure 13:
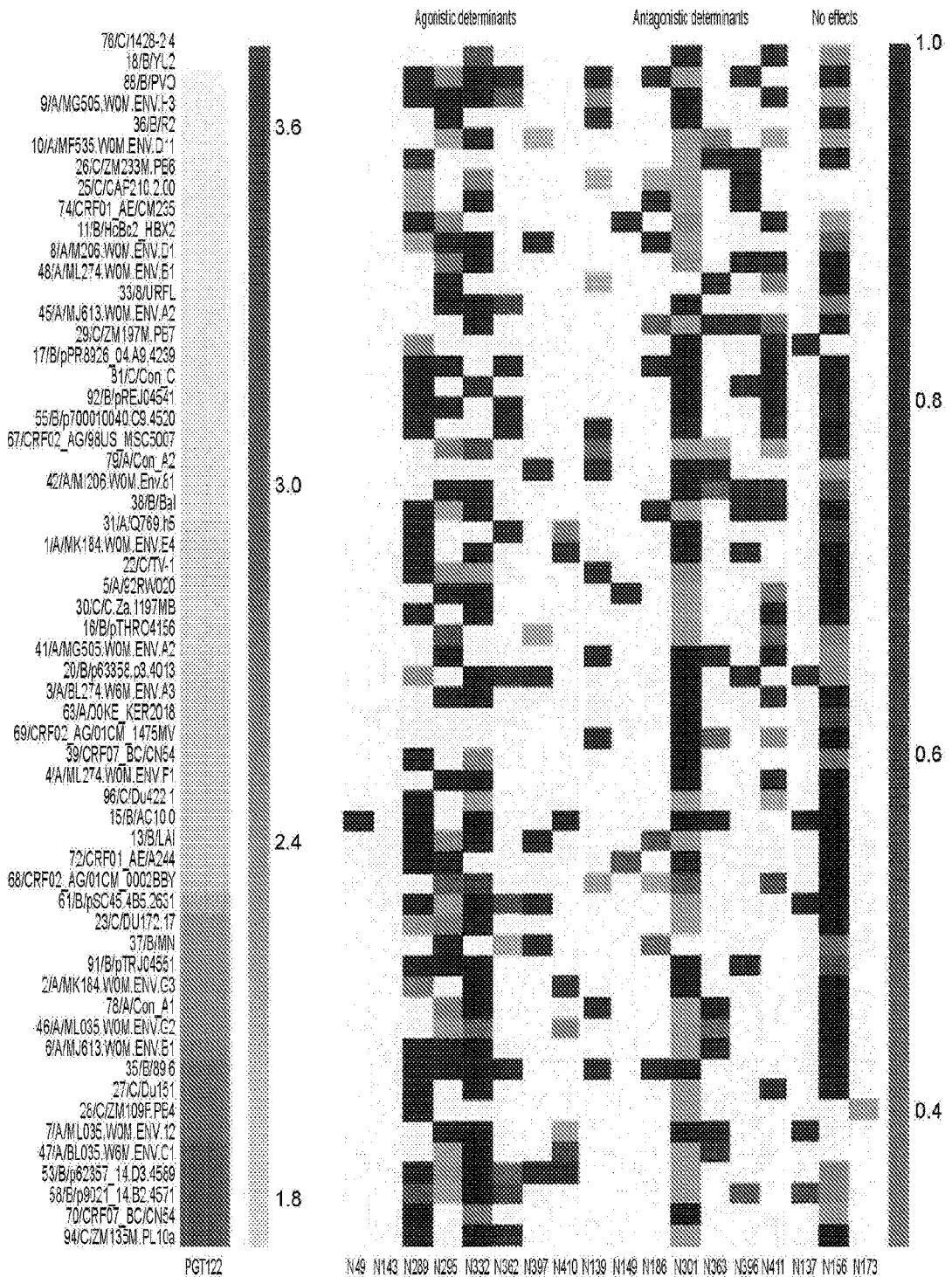
Figure 13:
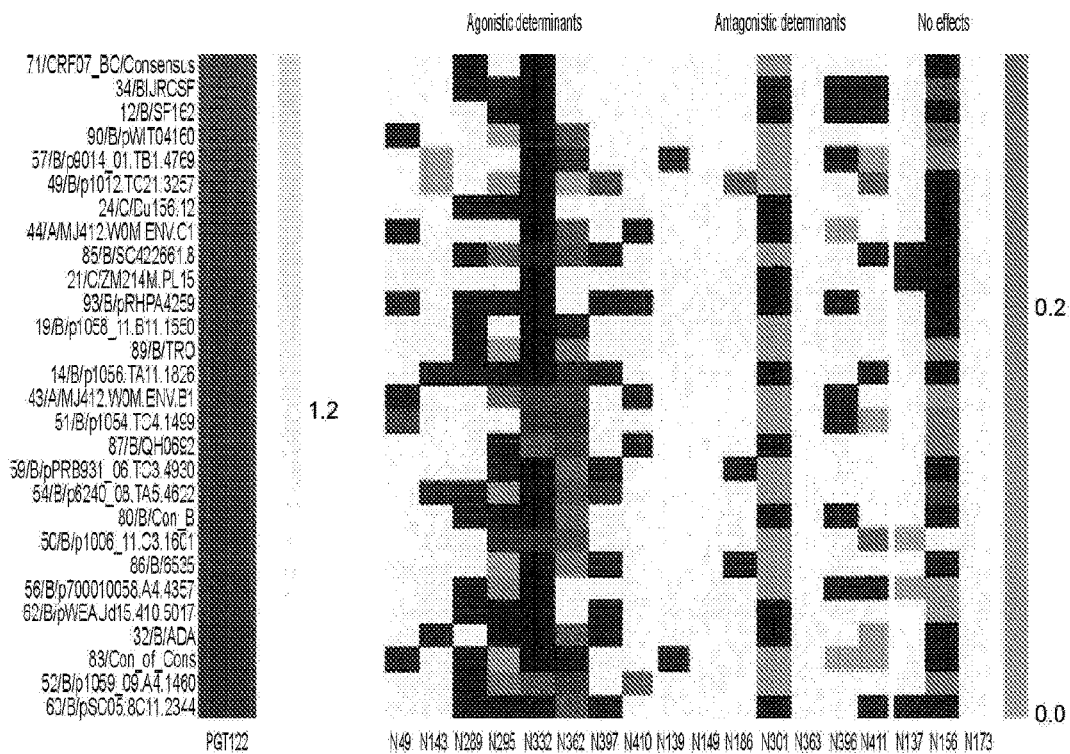
Figure 14:
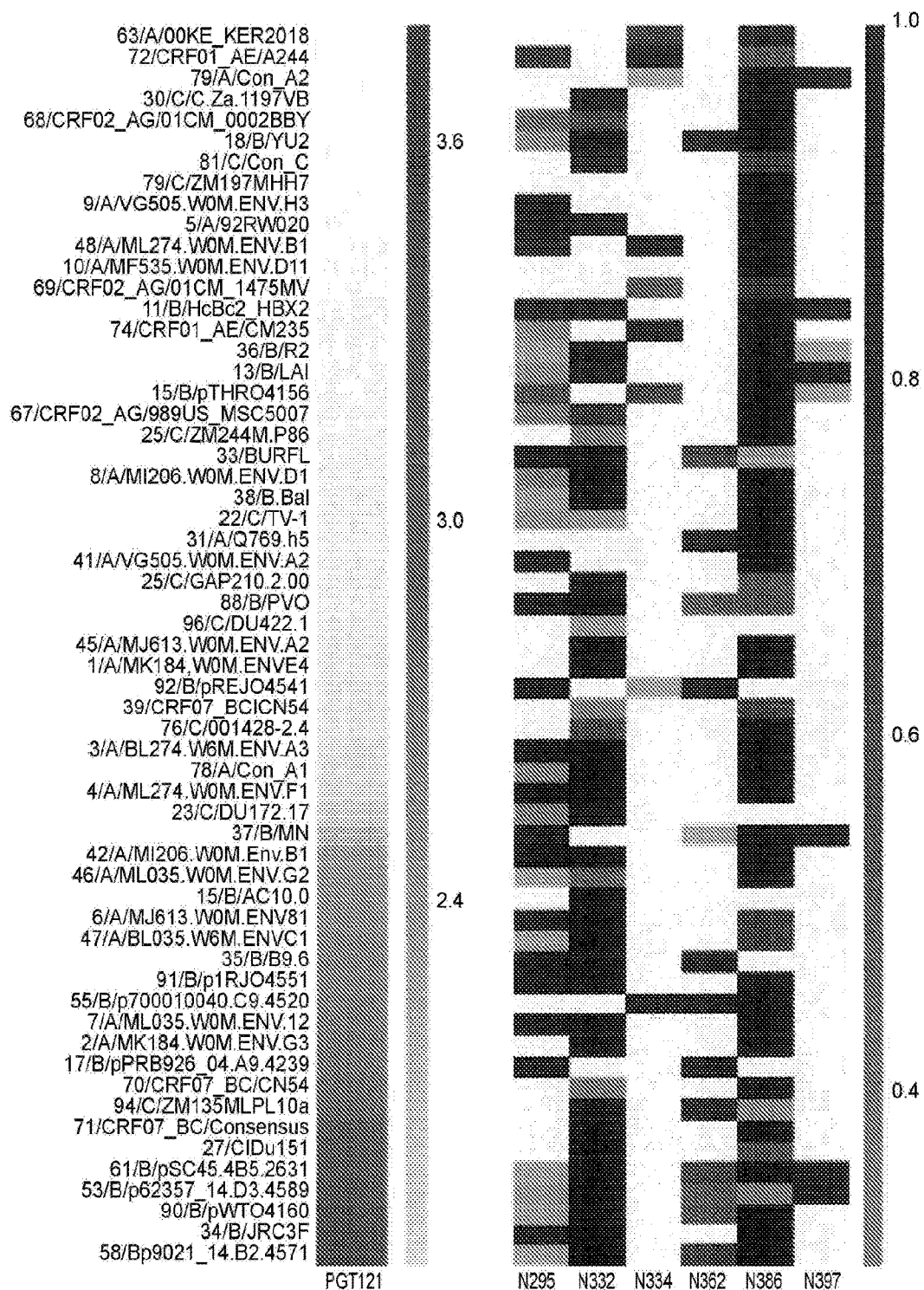
Figure 14:
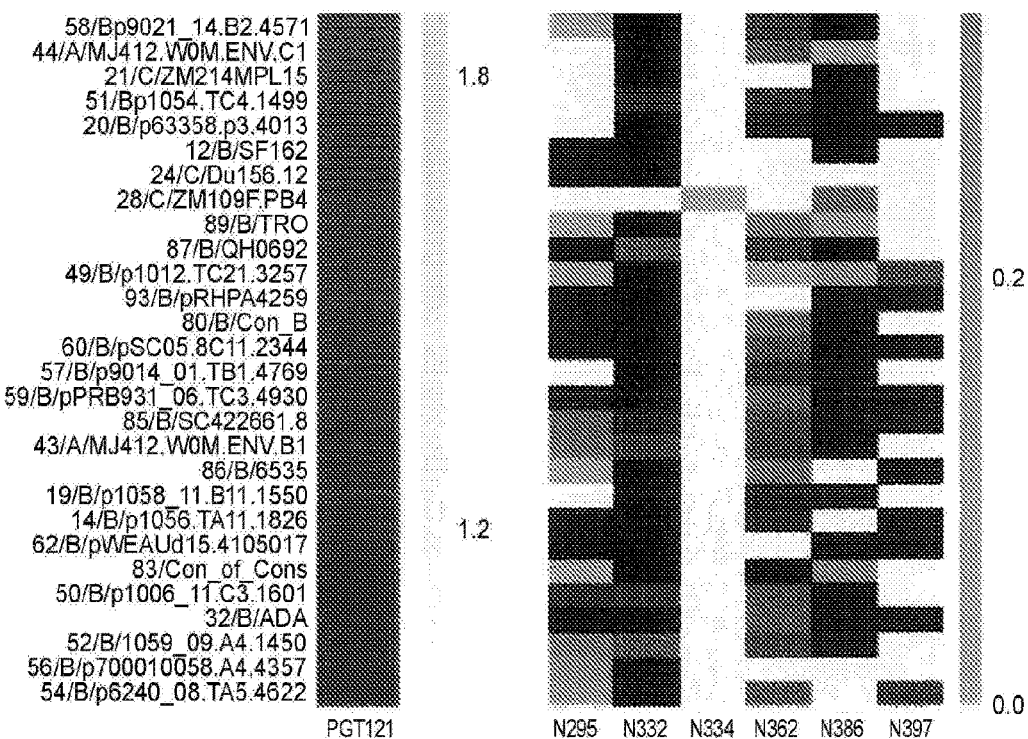

Because glycans could either improve and/or impair bNAb binding (FIG. 3C), the directionality of the glycan effect was introduced (+/−) as a positive/negative covariance, allowing for the deconvolution of the complex interactions between a specific bNAb and all glycans into a directional weight matrix (FIGS. 11, 4A). As expected, N332 occupancy was positively associated with all PGT family member and 2G12 binding profiles, but exhibited no effect on the CD4bs B12 and VRC01 binding profiles. Surprisingly, N397 was identified as an agonistic determinant for all tested bNAbs, located on the variable V4 loop region, but exhibited rare sequon presence (FIG. 1B) and intermediate glycan occupancy (FIG. 1C). Although N397 has not be previously analyzed in previous co-crystal structure reports, this glycan is found in clade B (FIG. 1A) and particularly in envelopes that exhibit better antibody detection (FIG. 2A). These data point to a critical role for the presence of a novel glycan, N397, which may stabilize other glycans or the envelope as a whole, permitting all bNAbs to bind and recognize their target. In addition, those identified glycan determinants specific to individual bNAbs mapped on gp120 monomer (FIG. 4B, 12) visually showed that some common glycans were shared among Abs in the family. Yet despite these common signatures, overall the glycan-binding fingerprints of individual bNAbs was still unique among each class of bNAbs highlighting the potentially utility of these agonist/antagonist binding differences to predict or shape future envelope immunogens.

Figure 4C:
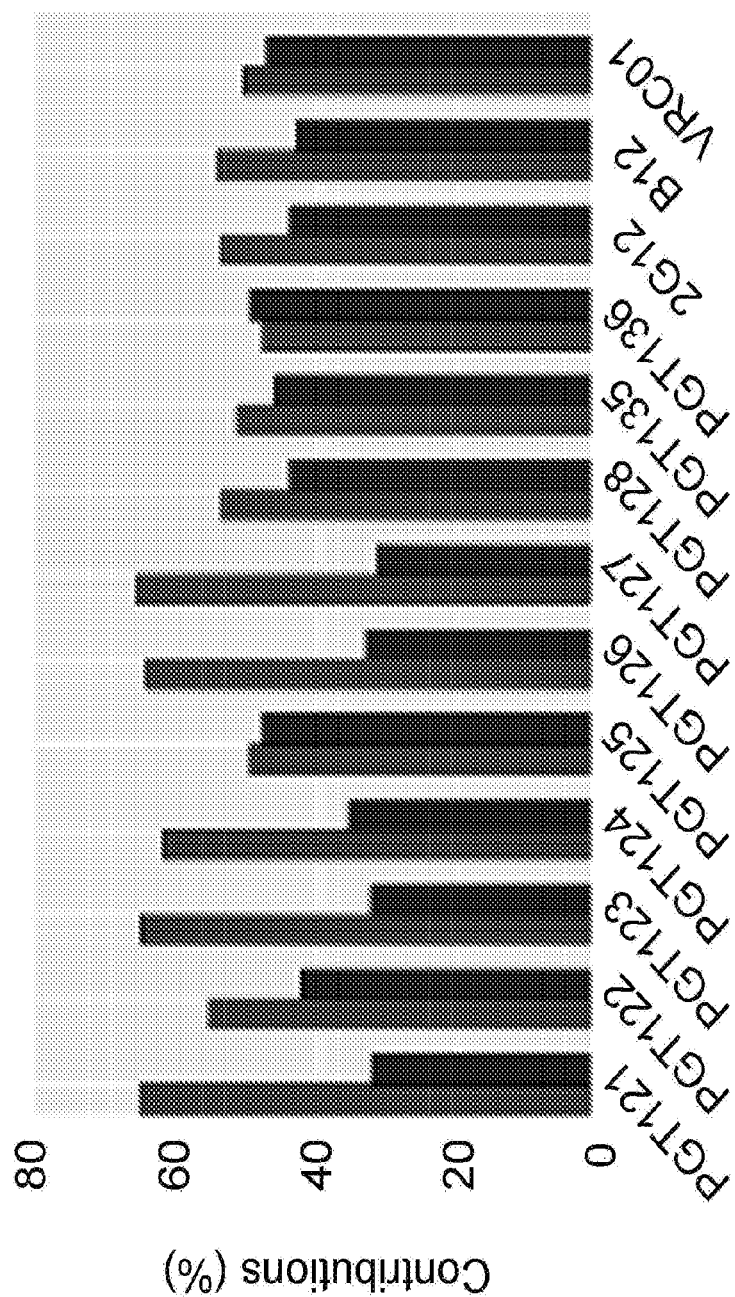

Interestingly, collected analysis of the absolute number of predicted antagonists and agonists for individual bNAbs demonstrated a peculiar different among bNAbs. A striking difference was observed among the PGT121-like bNAbs and the CD4bs bNAbs in the distributions of agonists and antagonists (FIG. 4C). For example, nearly 70% of the critical glycans identified by the model for PGT121 agonized binding, whereas only 30% negatively impacted bNAb binding. Conversely, for CD4bs antibodies such as VRCO1 nearly equivalent number of glycans contributed to improved and impaired bNAb binding. These differences may reflect differences in epitope location in such a way that the peripheral variable loop glycan-dependent bNAbs may be influenced to a lesser extent (Julien et al., 2013b) than the more complex, deeply recessed CD4bs antibodies (Chen et al., 2009).

Figure 4D:
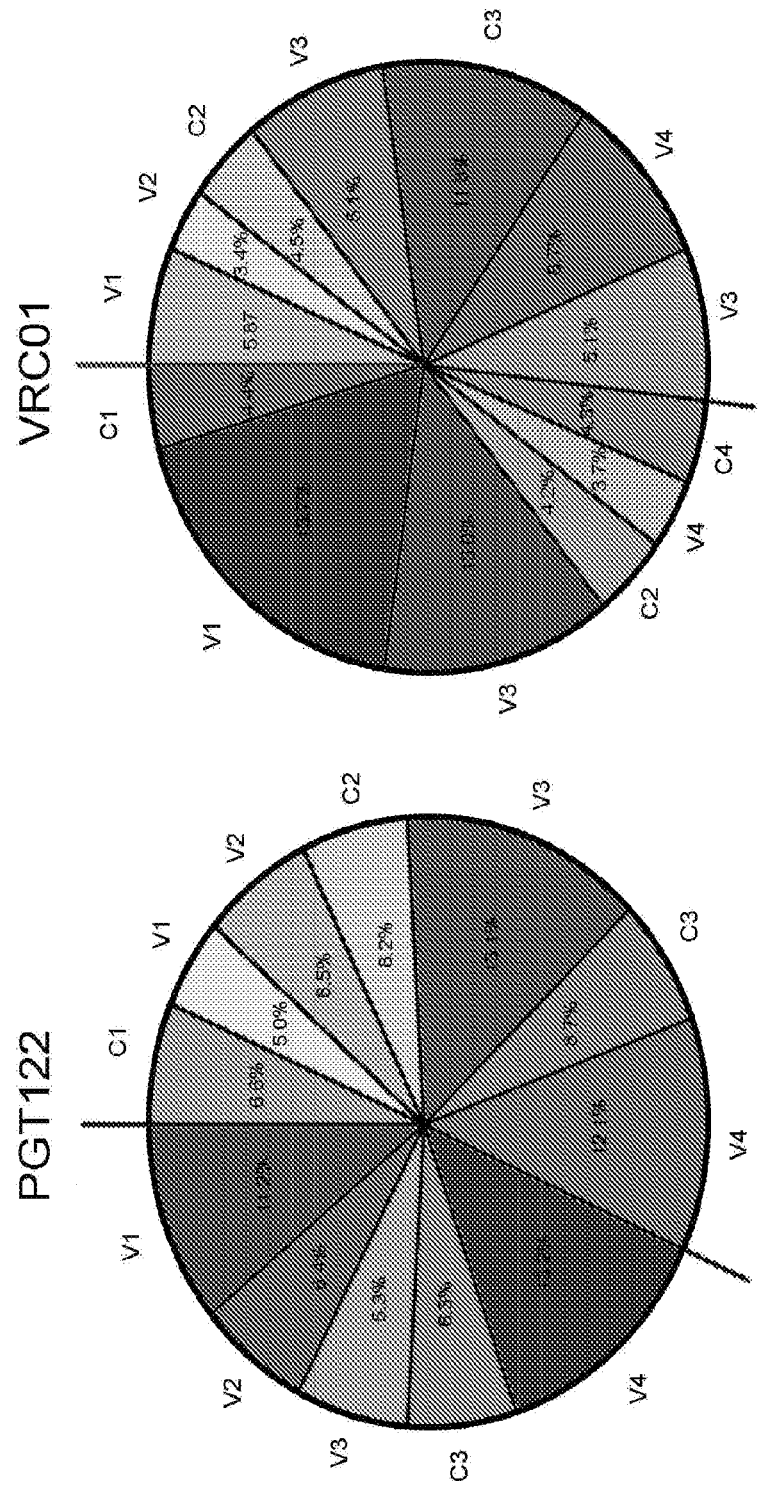

Further, the specific location of agonist/antagonist glycans was dissected across the variable and conserved regions of the viral envelope sequence (FIG. 4D). In VRC01, C3 and V4 showed dominant agonistic contributions to VRCO1 recognition, which accommodated the major sites of vulnerability of VRCO1 targeting (Zhou et al., 2010). Regardless of the fact that no glycans were identified to directly interact with VRCO1 from crystallography (Zhou et al., 2010), covariance data indicated that the presence of the glycans (N356, N362, N397, and N406) surrounding CD4bs epitope associating with high antigenicitic activities. In term of antagonistic contributions, V1 and V2 then showed the most impact on the recognition, which agreed with the hypothesis from the previous report (Lyumkis et al., 2013) that the glycans specific on V1/V2 loop conformationally located above CD4bs (Kwong et al., 1998; Wyatt et al., 1993) may interfere the antibody binding to CD4bs. Importantly, this analysis demonstrated that the recognitions of those CD4bs antibodies, which targeted the peptide backbone of the epitope, were still potentially enhanced or abrogated by the surrounding glycans, as shown similarly in the previous report (McGuire et al., 2013).

Figure 4E:
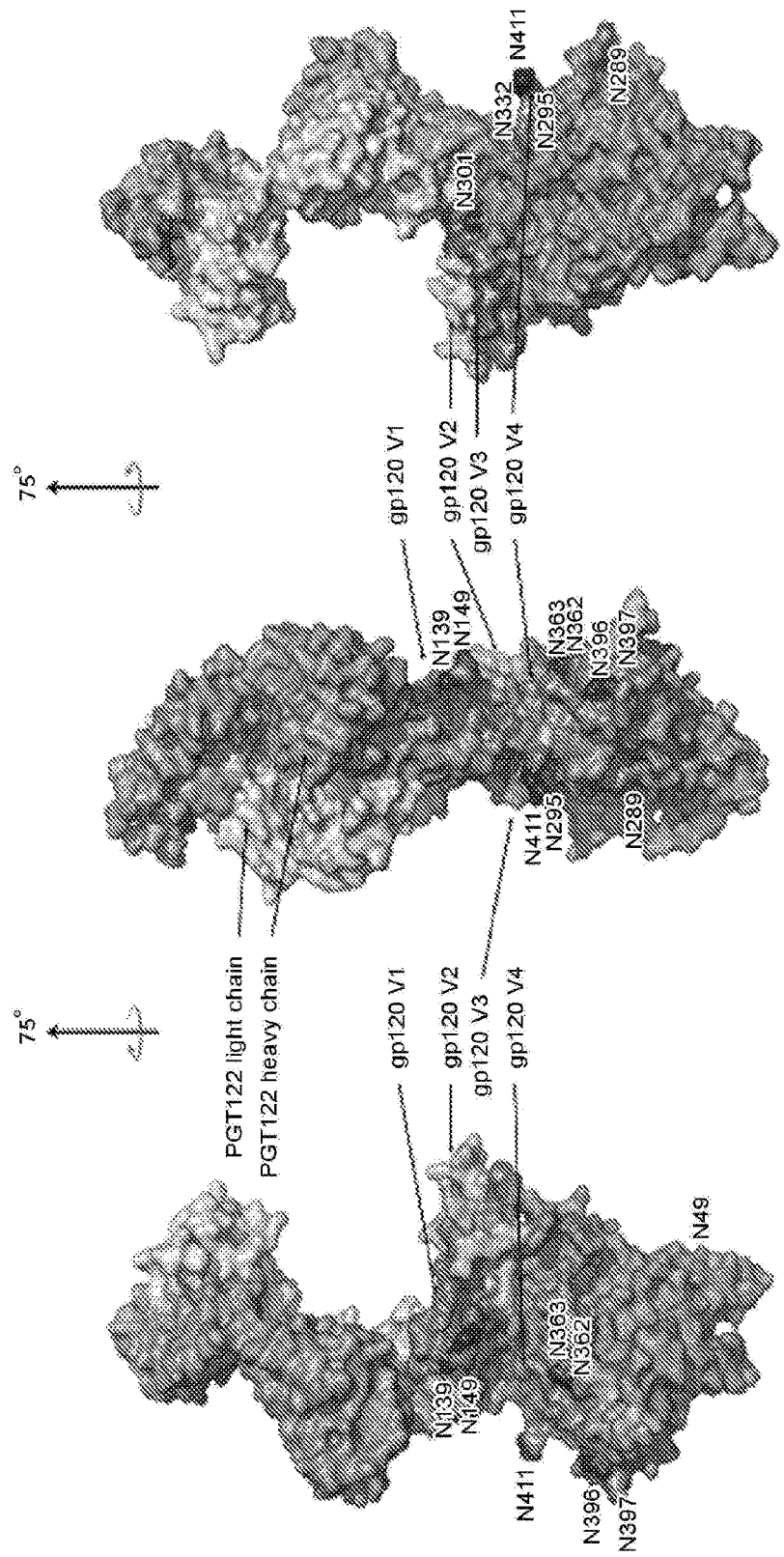

For PGT122, the glycans facilitating PGT122 recognition mainly appeared in V3 and V4 regions (FIG. 4D) where the N332 and N295 glycans appear to participate directly in the bNAb binding surface, and the N362 and N397 glycans in V4 appear on the edge of the binding pocket, potentially involved in stabilizing the interaction around the pocket (FIG. 4E). Conversely, PGT122 antagonists were largely located in the V1 and V4 loops, including N139 and N149 on the V1 loop, N396 and N411 in the V4 loop and N301 on the V3 loop. Glycan mapping on the co-crystal structure highlighted the location of the glycans located right above the PGT122 epitope (FIG. 4E), providing a plausible mechanism by which these antagonistic glycans may interfere with PGT122 accessing to its epitope in the pocket.

It is likely that the importance of these inhibitory glycans on PGT122 binding may have been overlooked as these glycans were enzymatically trimmed for co-crystal stabilization. Interestingly, this analysis also pointed to 2 distal PNGS agonists, the N49 and N289 glycans, suggesting that the glycans appearing on N49 or N289 may either reduce conformational flexibility of carbohydrate chains above the epitope or conformationally change protein backbone to make the epitope more exposed. Thus, it is likely that an array of both proximal and distal glycan collectively contribute to shaping bNAb binding profiles in a coordinated manner.

Example 5: Glycan-Fingerprint Based Immunogen Design to Switch bNAb Binding Antigenicity Profiles Given the unique complex networks of antagonistic/agonistic glycans (FIG. 4A) that drive the observed unique bNAb fingerprints (FIG. 2A), observed for each of the tested bNAbs (FIG. 4A) it was hypothesized that these signatures could be integrated to design custom antigenically enhanced gp120 immunogens for the selective binding and induction of bNAbs targeting specific epitopes. A de novo immunogen design program, trained on the gp120 occupancy profiles, bNAb binding footprints, envelop sequences, and structural information, was utilized to iteratively evolve a poorly antigenic gp120 envelope, in silico, using specific bNAb binding profiles as the evolutionary force. Immunogen design focused on PGT121 and PGT128 bNAbs, due to their related but distinct antigenic fingerprint profiles (FIG. 2A) focused on the clade A MF535.W0M.ENV.D11 gp120 sequence that demonstrated negligible binding to either bNAb (FIG. 5A).

After 200,000 rounds of evolution, a set of combinatorial glycan site mutations were identified in the original gp120 sequence predicted to enhance PGT121 and/or PGT128 binding. Agonistic glycan determinants were added and all the required antagonistic glycan determinants were eliminated. The engineered immunogen proteins were produced and correct folding was assessed as equivalent binding using VRC01 (no differential binding expected) and D7324 (epitope tag in the X-terminal end of the protein) antibodies. Indeed PGT121 and/or PGT128 binding was improved, as anticipated based on program predictions (FIG. 5B). More importantly, the data showed that the optimized immunogen preferred to bind one bNAb but not the other, such that PGT121-optimized immunogen exhibited a better binding activity to PGT121 instead of PGT128, whereas the PGT128-optimized immunogen showed a divergent manner (FIG. 5B). The +PGT121+PGT128 immunogen then displayed an equal activity to both bNAbs (FIG. 5B). Together demonstrated the potential of this glycan-optimization engineering approach to develop immunogens with improved antigenicity to select bNAbs.

Figure 5A:
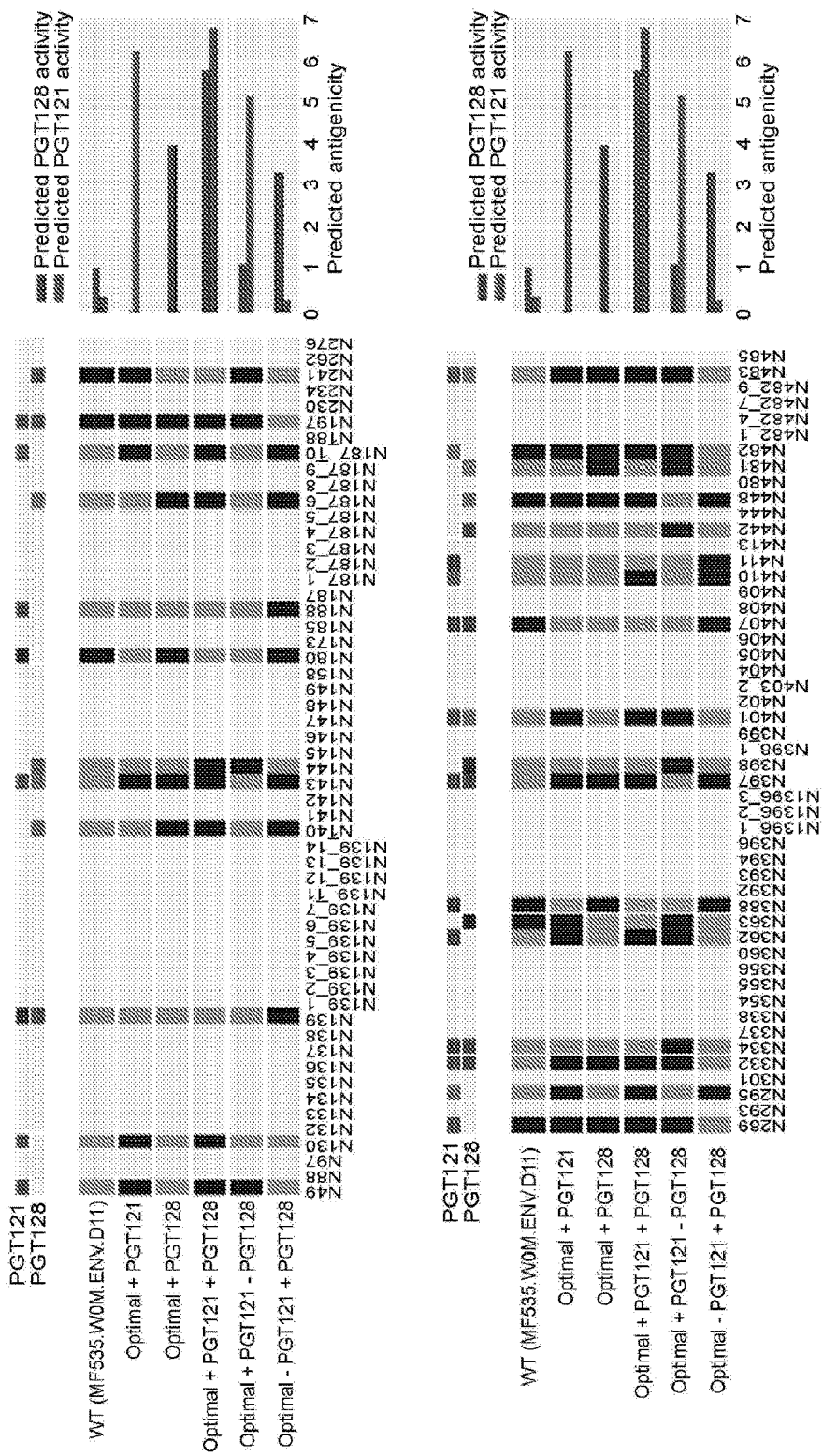
FIGS. 5A-5E depict a proof-of-concept for De novo immunogen design.
Figures 5B, 5C:
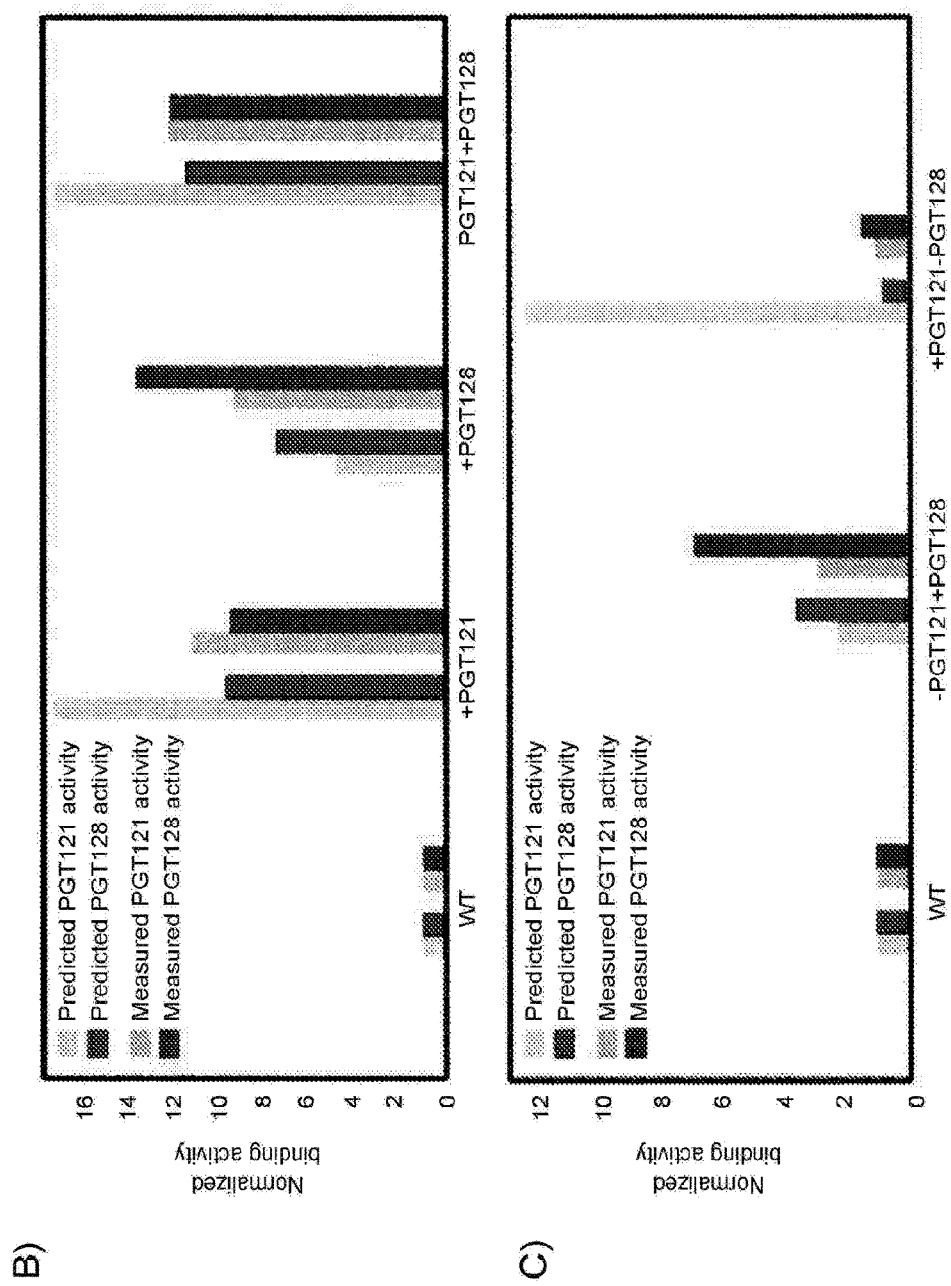

To next determine whether selective antigenicity could not only improve select bNAb binding, but also selectively block other bNAbs, to generate antigenically customized immunogens, two additional immunogens were designed to prevent PGT121 and/or PGT128 binding (FIG. 5A, +PGT121−PGT128 and −PGT121+PGT128). Thus an immunogen containing PGT121 agonist glycans and PGT128 antagonistic glycans, and the other containing PGT128 agonist glycans and PGT121 antagonistic glycans were synthesized. PGT121 blockade was successfully achieved on the −PGT121+PGT128 immunogen, and PGT128 binding was observed at predicted levels on the −PGT121+PGT128 immunogen (FIG. 5C). Additionally, PGT128 blockade was observed on the +PGT121-PGT128 immunogen, as predicted (FIG. 5C), however, PGT121 binding was not enhanced, likely related to creating a steric hindrance from those added glycans, such as N332 and N334, at the PGT121 binding epitope. Thus, next generation immunogen engineering and synthesis could incorporate additional information such as spatial distance between the target PNGS and the neighbors calculated from gp120 structure to improve PGT121 binding on the +PGT121−PGT128 immunogen.

Figures 5D, 5E:
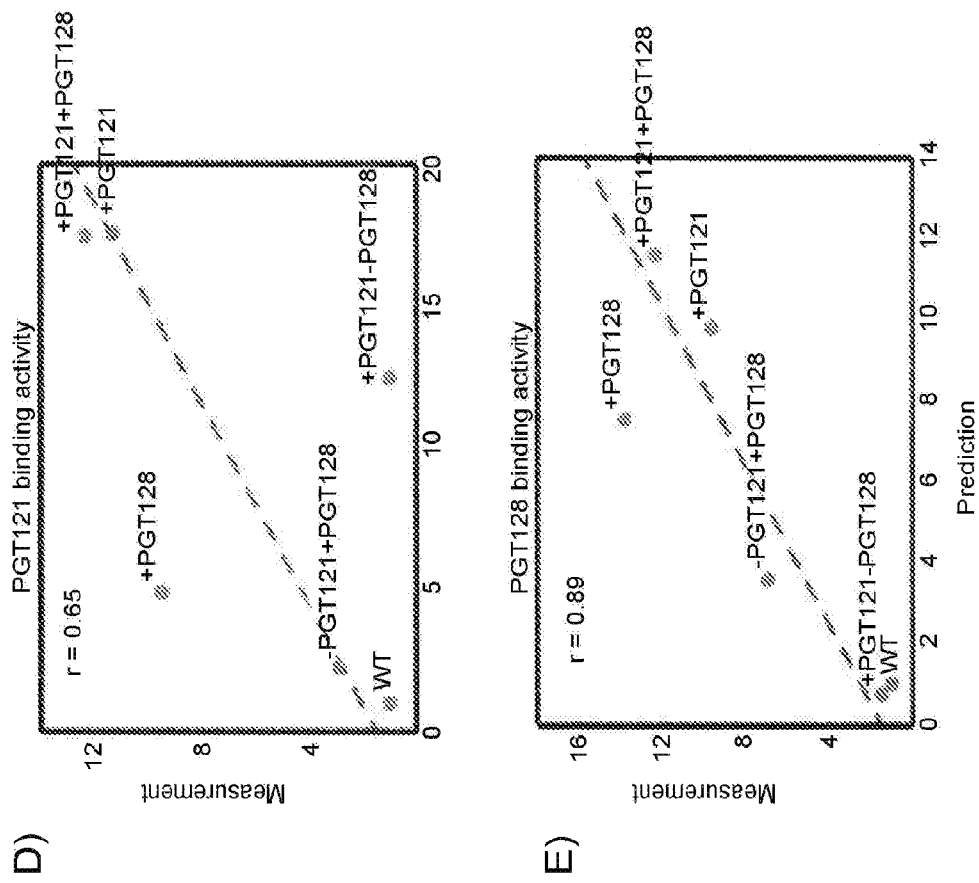

Yet overall the PGT128 binding activities of the five designed immunogens displayed a very consistent Ab response profile as predicted by the model prediction (r=0.89) (FIG. 5E), whereas PGT121 were also selectively modulated (r=0.65), albeit to a lesser degree than PGT128 optimized immunogens. Interestingly, +PGT121+PGT128 consistently exhibited the best binding against both PGT121 and PGT128 among all immunogens, confirming that common glycans contribute to PGT121 and PGT128 binding because of a certain level of overlap between two epitopes (Julien et al., 2013a). Moreover, both +PGT121−PGT128 and −PGT121+PGT128 showed relatively lower binding against both Abs than the other engineered immunogens. The bNAb-glycan interaction signatures showed that PGT121 and PGT128 shared some of antagonistic glycan determinants (N139, N334 and N407) (FIGS. 4A and 5A), demonstrating that those added antagonistic glycans blocking the target Ab binding may also negatively impact to the other Ab but with different degrees of the influence. However, despite this common glycan usage, select mutations could be engineered in the immunogens to selectively push PGT128 recognition, highlighting the possibility of utilizing this glycan-engineering approach to not only improve overall binding to specific bNAb specificities, but also to selectively antagonize other specificities.

Example 6: HIV Gp120 Variant Proteins and Broadly Neutralizing Antibodies

Gp120 protein monomers produced in 293 cells were purchased by Immune technologies, and may be obtained from a variety of commercial means. PGT121 and VRCO1 antibodies were obtained by NH-I AIDS reagents program and may be obtained from a variety of commercial means. 2G12 and B12 antibodies were purchased by Polymun Scientific and may be obtained from a variety of commercial means. PGT122, 123, 124, 125, 126, 127, 128, 135 and 136 were generously provided by Dr Dennis Burton, Scripps and may be obtained from a variety of commercial means.

Example 7: ELISA-Based Antigenicity Assay

In some examples, ELISA assays may be performed by capturing gp120 monomers on D7324-coated (anti-C-terminal gp120 sheep antibody, Aalto Bioreagents) plates. Briefly, Nunc Maxisorp 384-well plates were coated overnight at 4 C with 10 g/ml of D7324 in 0.1M NaHCO3 (pH 8.6). Plates were washed 4 times with PBST (PBS±0.01% tween) and blocked with PBSA (PBS containing 5% BSA) for 1 hour at room temperature. After 4 washes with PBST gp120 proteins were added at 80 ng/ml final concentration in PBSA and incubated for 2 hours at room temperature. After washing 6 times with PBST, bNAbs were added at 10 g/ml in assay diluent (PBS containing 5% BSA and 20% sheep serum) and incubated for 2 hours at room temperature. After 6 washes in PBST, biotin-conjugated mouse anti-human IgG (BD Biosciences) was added to each well at 1:1000 dilution in PBSA and plates were incubated for 1 hour at room temperature. After 6 washes in PBST high-sensitivity streptavidin-HRP (Pierce) was added to each well at 1:100 dilution in PBSA and incubated for 1 hour at room temperature. Plates were washed 6 times in PBST and developed by adding UltraTMB substrate (Pierce) to each well. Development was stopped by adding 2M sulfuric acid to each well and plates were read at OD450 with Tecan 1000 pro reader. Background OD values (wells without gp120) were subtracted from test wells containing gp120 proteins. Two biological replicates and three technical replicates for each bNAb were performed to provide a statistical estimation and to evaluate assay reproducibility. The collected ELISA data from biological replicates were normalized by median centering to avoid systematic variance, aiding in cross-experiments comparison. In addition, the reproducibility between replicate data sets was evaluated by examining the coefficients of variation (CV), i.e. standard deviation divided by mean.

Example 8: Identification of Consensus Glycosylation Sites from HIV Gp120 Sequences The 98 of HIV gp120 sequences were collected and used to run multiple sequence alignment by Clustal Omega (EMBL-EBI). The output of alignment was manually adjusted to get the optimal alignment for glycosylation sites among the sequences, particularly in the region of variable loops. Then, the consensus sequon of glycosylation (N-X-S/T) was scanned through aligned sequences to identify all potential glycosylation sites. The position number of glycosylation site for each aligned sequence was mapped to the position of the gp120 consensus sequence—HXB2. The nomenclature of the glycosylation positions, in the case that the glycosylation sites are absence in HXB2, was determined by the position of the previous aligned residue mapped to HBX2, and the rank of the current residue following the aligned residue. For instance, N137.5 indicates the glycosylation site found at the fifth residue after the glycosylation site N137 in HXB2.

Example 9: Determination of Glycan Occupancy at N-Linked Glycosylation Sites by Mass Spectrometry From mass spectrometry output, the amount (spectral counting) of each peptide with different chemical modification forms were relatively quantified, and the site-specific glycan occupancy was then calculated as following.

$$a = \{a_1, a_2, \ldots, a_i\}$$

$$E(g_{a_j}) = \Sigma F_{p_i} W_{p_i}$$

where a indicated all glycosylation sequons from a gp120 sequence composed of number of i sequons, E was considered as the expected frequency of each glycosylation sequon $a_i$ as the function of the weighted average, where $F_{pi}$ presented as the frequency of the glycosylation-modified peptide containing the sequon, and $W_{pi}$ as the weight where the amount of that peptide over all detected peptides covered the sequon $a_i$.

Example 10: Pairwise Covariance Analysis Between Glycan Occupancy and Antigenicity To directly link site-specific glycosylation occupancy with antibody binding affinity, the first model is to build a pairwise Pearson correlation matrix between site occupancy and nAb antigenicity, where the model was considered that antibody binding affinity was linearly dependent on each single glycosylation site at time. The value of correlation coefficient showed the strength of relationship between the glycosylation site with the antibody, and its sign of the value inferred either agonistic or antagonistic correlation between site-specific glycosylation occupancy and antibody binding on gp120 epitope.

Example 11: Probabilistic Model with Machine Learning Algorithm to Identify the Glycan Determinants Broadly neutralizing antibodies binding on HIV envelop usually involved in multiple conformation-nearby glycosylation sites as well as potential distant sites. Considering single independent site is limited to identify multiple mutually dependent glycosylation sites essential for antibody recognitions. In order to identify and discover this hidden complex relationship, a machine learning algorithm was developed, which integrated two parts: (1) Support vector regression (SVR) that implemented support vector machines (SVMs), a supervised learning model, to recognize glycosylation site occupancy and to predict (regress) antibody binding affinities learned from the training model. (2) Bayesian Markov chain Monte Carlo (MCMC) with Metropolis-Hastings algorithm, a biased random walk, to approximate the high-dimensional probability distribution and to identify the optimal combinatory glycan determinants showing the best model prediction consistent to the experimental results.

The Model.

105 of potential N-linked glycosylation sites (PNGSs) were identified from previous multiple alignment of 98 gp120 cross-clade sequences. It was hypothesized that each PNGS could be classified as either determinant or non-determinant for broadly neutralizing antibody recognition. The definition of determinant here included both promotion and inhibition of antibody binding affinity. The model for identification of glycan determinants was represented by a joint probability distribution P(X) from a multi-dimensional space.

Joint probability = $P(X)$, $X = \{x_1, x_2, \ldots x_{105}\}$ $x_i = \begin{cases} 1 & \text{determinant} \\ 0 & \text{otherwise} \end{cases}$ where the PNGS x, indicated a dimension and contained two states [0, 1]. As results, the whole probability distribution containing $2^{105}$ states was extremely difficult to direct sampling. Thus, the integrated algorithm provided a statistical estimation to the glycan determinant distribution P(X) given a set of experimental observations. According to Bayes' theorem, the conditional probability of the glycan determinants given an observed data set as followed, $$p(X_{opt} \mid \text{data}) = \frac{p(\text{data} \mid X_{opt}) p(X_{opt})}{p(\text{data})}$$

where $X_{opt}$ denotes the vector of the glycan determinants in the model and $p(X_{opt}|\text{data})$ represents the posterior of $X_{opt}$. $p(\text{data}|X_{opt})$ and $p(X_{opt})$ are likelihood and prior of $X_{opt}$, respectively. Since the ratio of posterior is only required during following MCMC sampling, we can simplify the equation into, $$p(X_{opt}|\text{data}) \propto p(\text{data}|X_{opt}) p(X_{opt})$$

The equation is then to transform as followed. Therefore, the value of the log posterior is sum of the log likelihood and log prior as following, $$-\ln(\text{posterior}(X_{opt})) = -\ln(\text{likelihood}(X_{opt})) - \ln(\text{prior}(X_{opt}))$$

Then $-\ln(\text{likelihood}(X_{opt}))$ was calculated by the sum of mean squared errors (MSE) between the prediction from SVR and the observed data for a given set of glycan determinans. SVR was basically trained by a selected glycosylation site occupancy ($X_{opt}$), and 10-fold cross-validation was implemented which randomly divided the data into the training and test sets and estimated the fitness by calculating MSE. Next, $-\ln(\text{prior}(X_{opt}))$ was calculated by the sum of squared deviation between the selected and empirical glycan determinants on the assumption that the distribution of the site identified between two states [0,1] followed a Gaussian distribution.

$$-\ln(\text{prior}(X_{opt})) = \sum_j \frac{1}{2\sigma_j^2}(x_j - \langle x_j \rangle)^2$$

where $\sigma_j^2$ and $\langle x_j \rangle$ are variance and mean of glycan occupancy at the site $x_j$. To sample the desired probability distribution P(X), a Metropolis-Hastings MCMC walk was implemented, a biased random walk, where the algorithm iteratively computed the posterior at current and next position, in which the posterior was theoretical proportion to P(X), the decision of jumping to next position was then followed, $$X_{s+1} = \begin{cases} X' & \text{if } \text{Unif}(0, 1) \leq \alpha(X_s, X') \\ X_s & \text{otherwise} \end{cases}$$

$$\alpha(X_s, X') = \min\left(1, \frac{\text{posterior}(X')}{\text{posterior}(X_s)}\right)$$

where $X_s$ indicates the current position and X' the candidate for next position; $X_{s+1}$ the next position. The distribution a of the next position was dependent only on the current position value as the definition of Markov chain. The algorithm, therefore, generated a sequence of sample values in which the distribution of values closely approximates the original probability distribution P(X).

Figure 7:
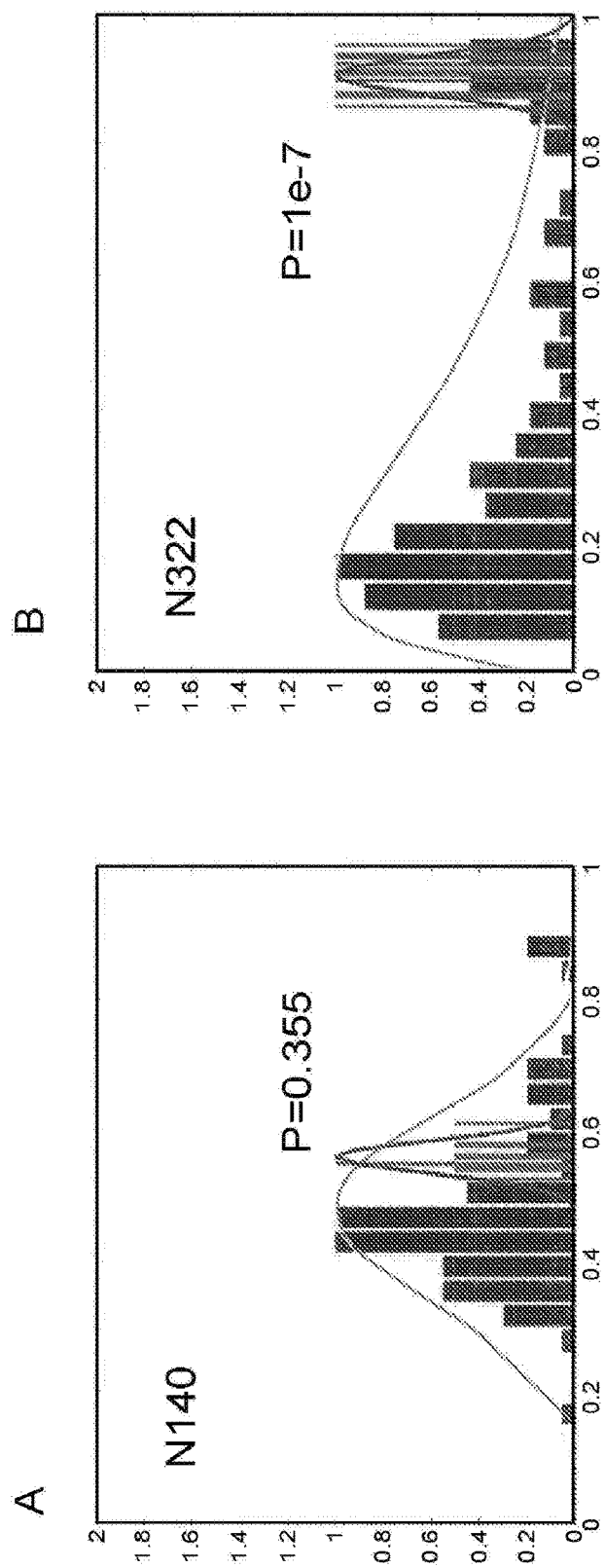
Figure 8A:
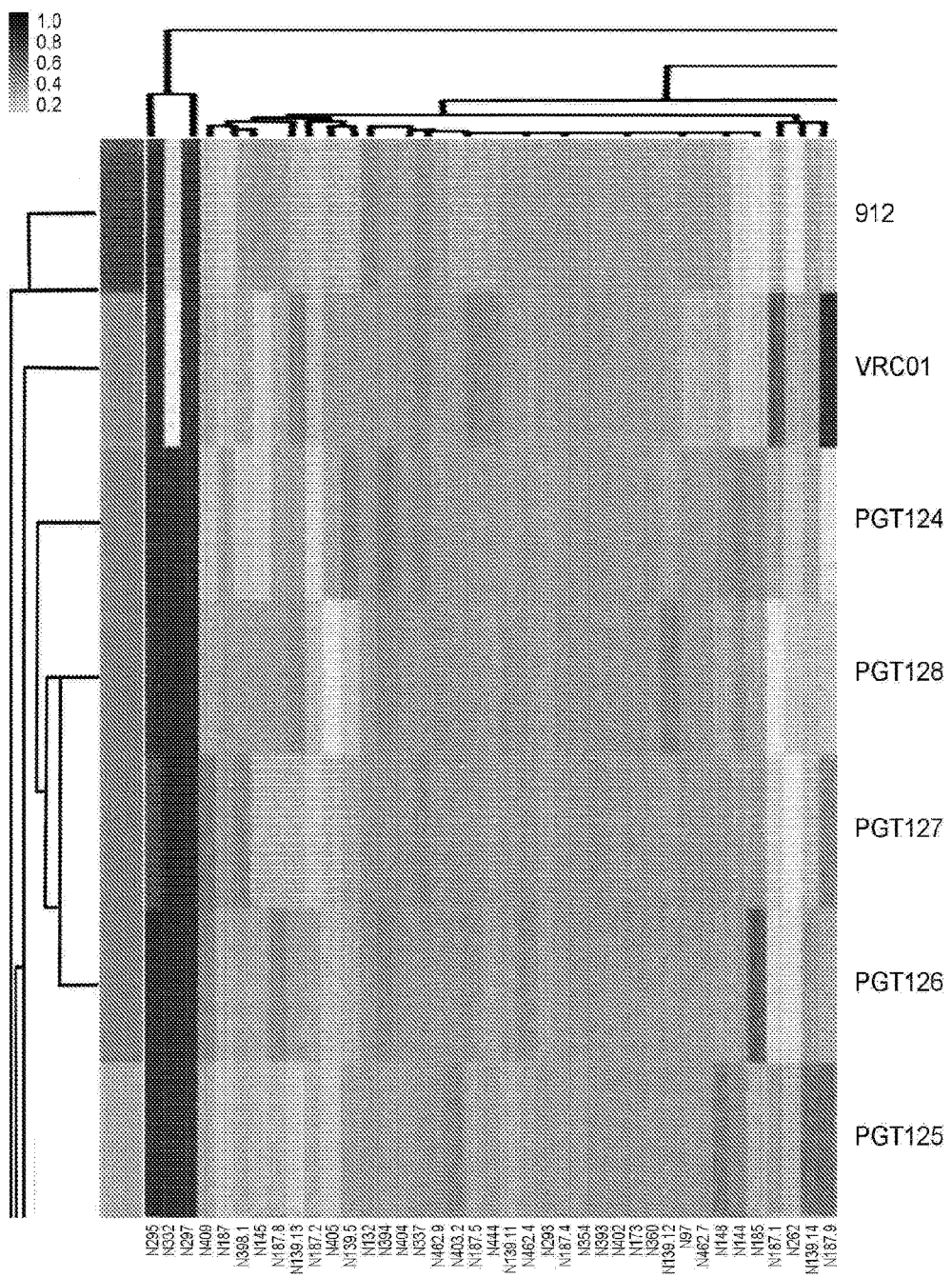
Figure 8A:
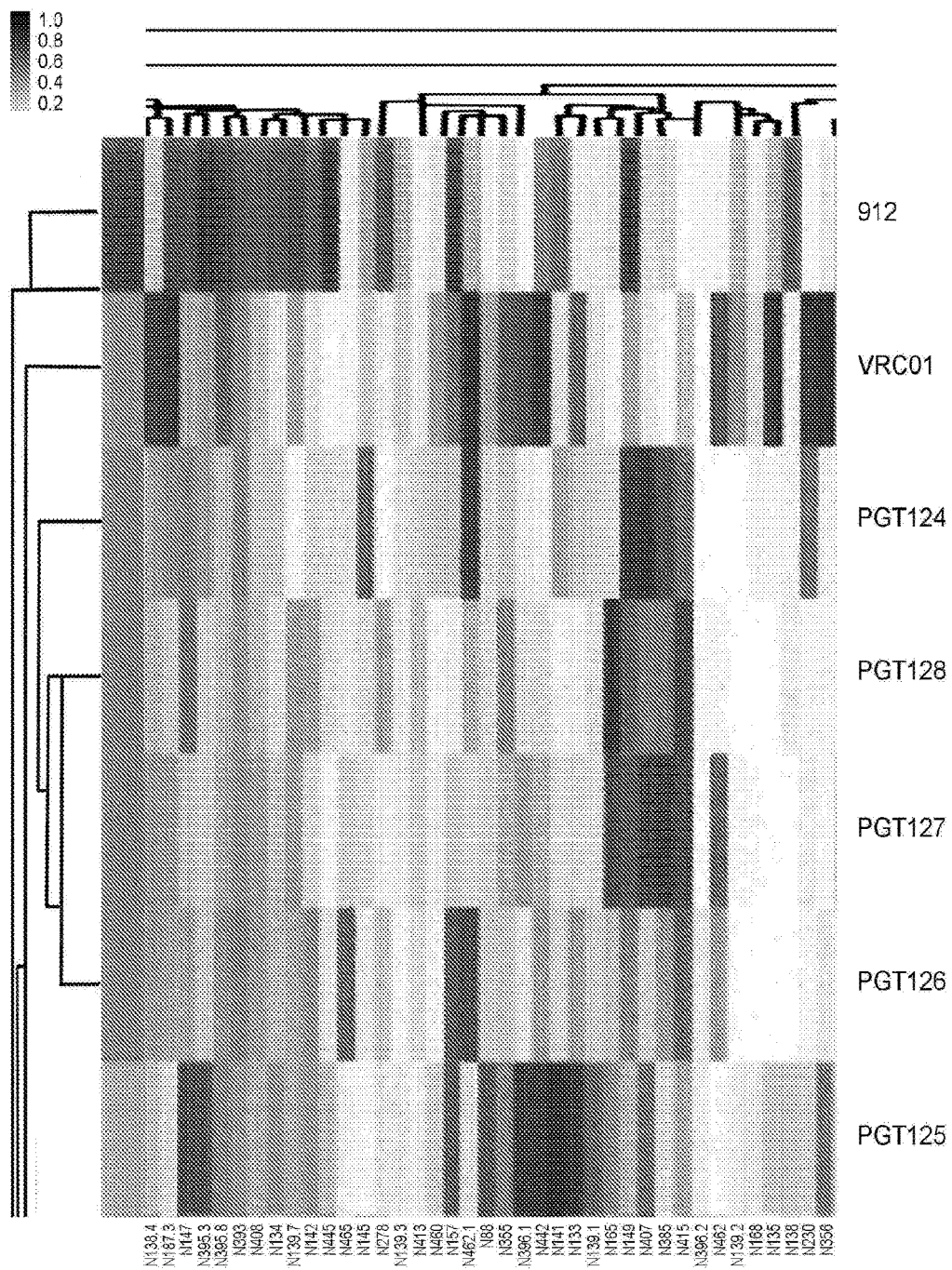
Figure 8A:
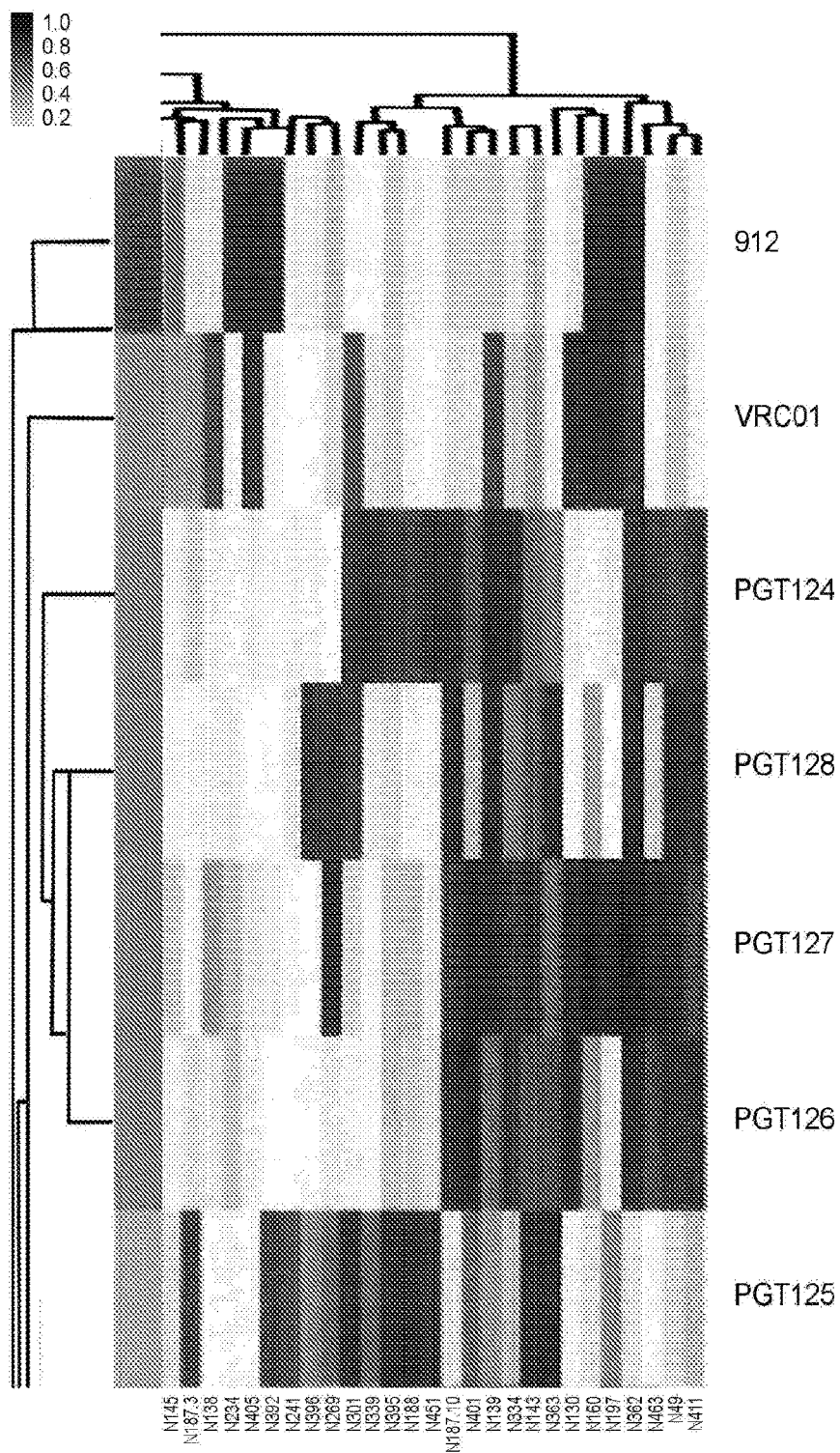
Figure 8B:
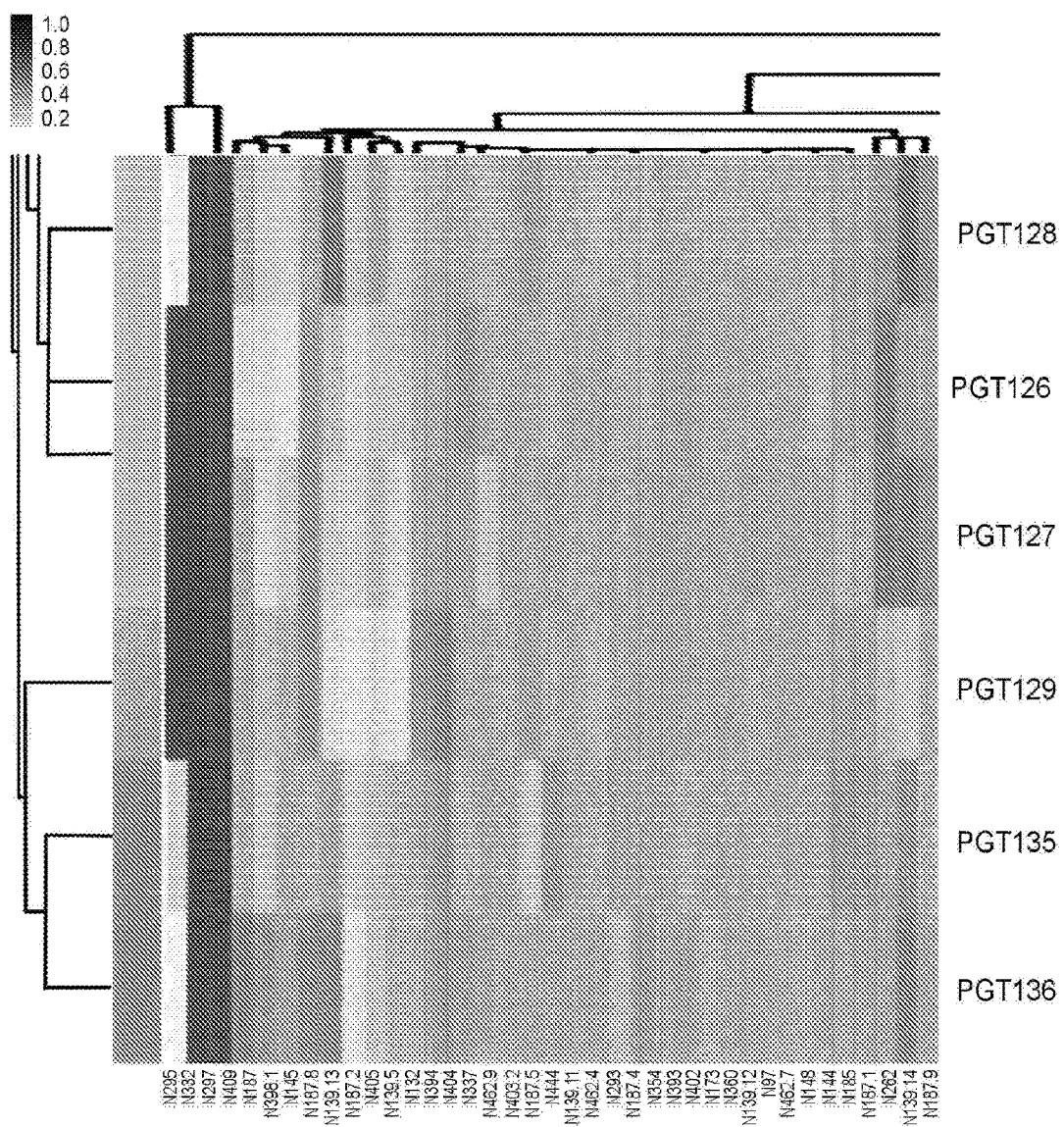
Figure 8B:
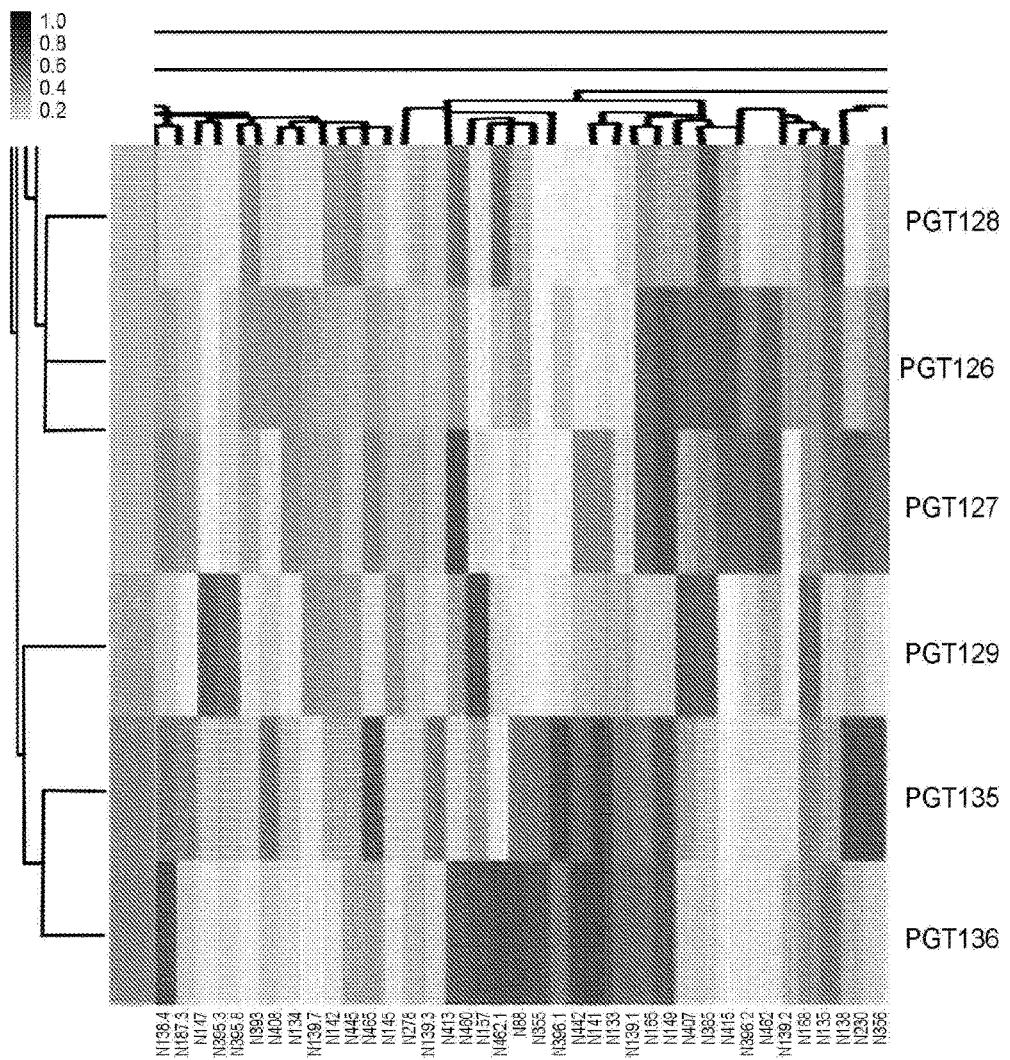
Figure 8B:
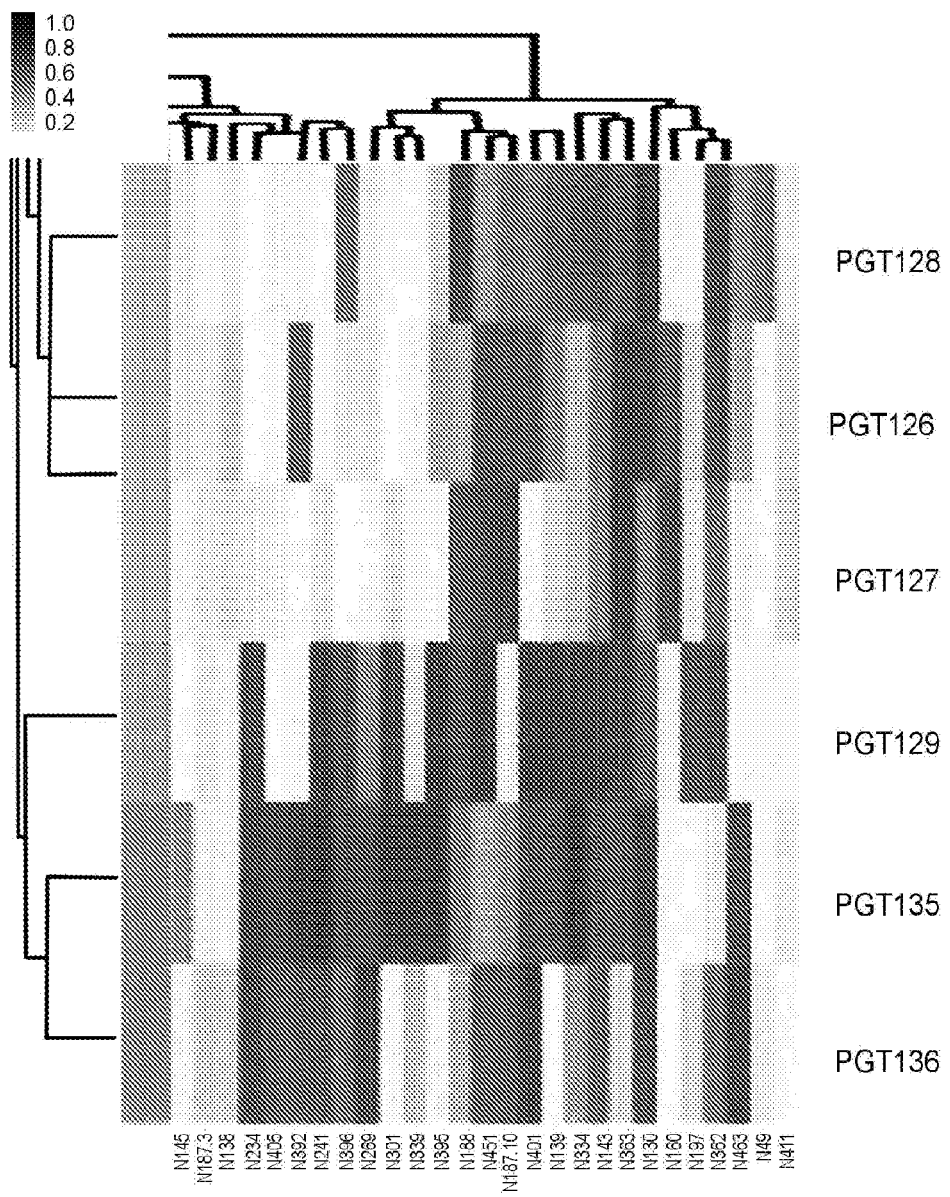
Figure 9A:
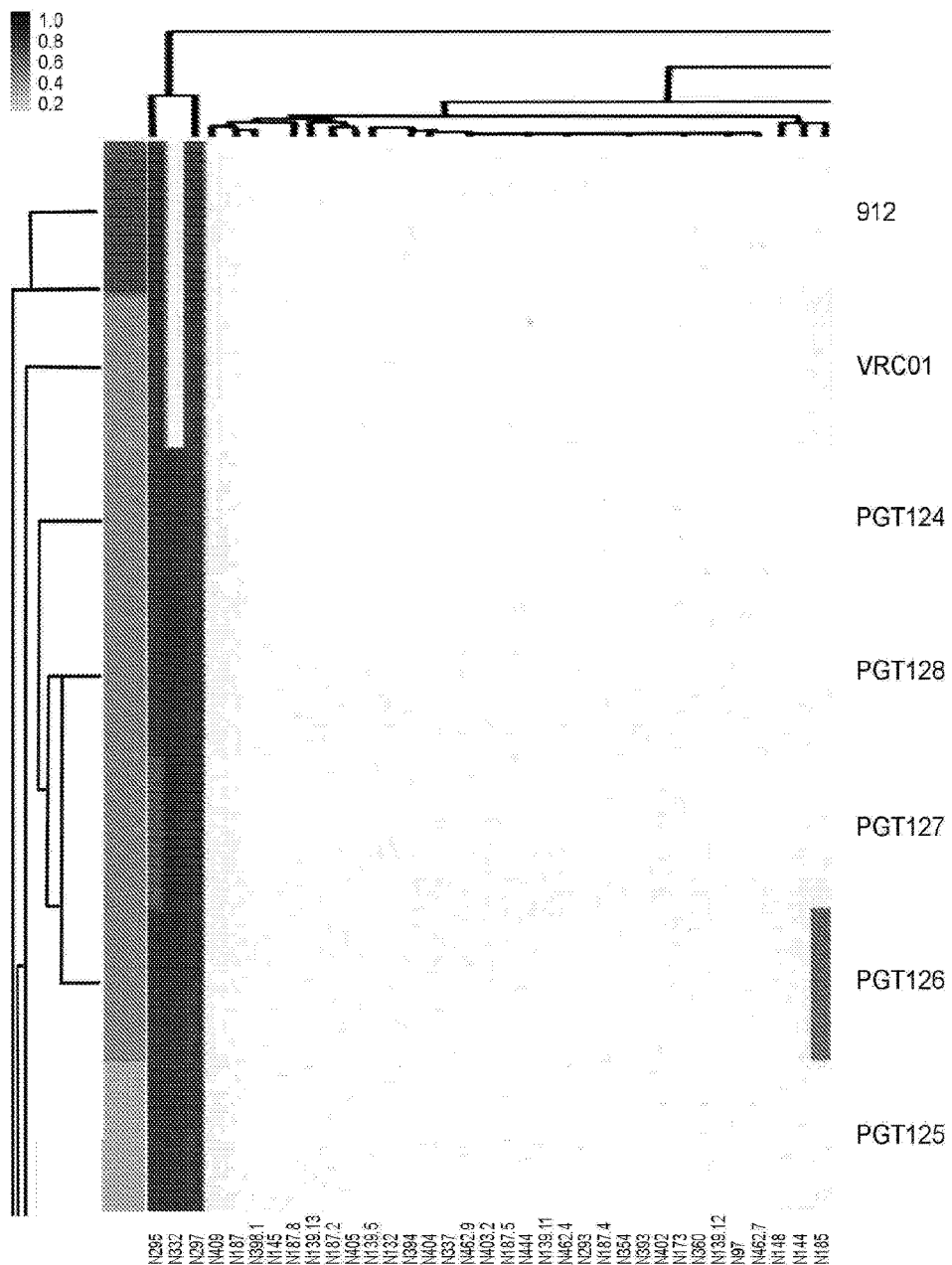
Figure 9A:
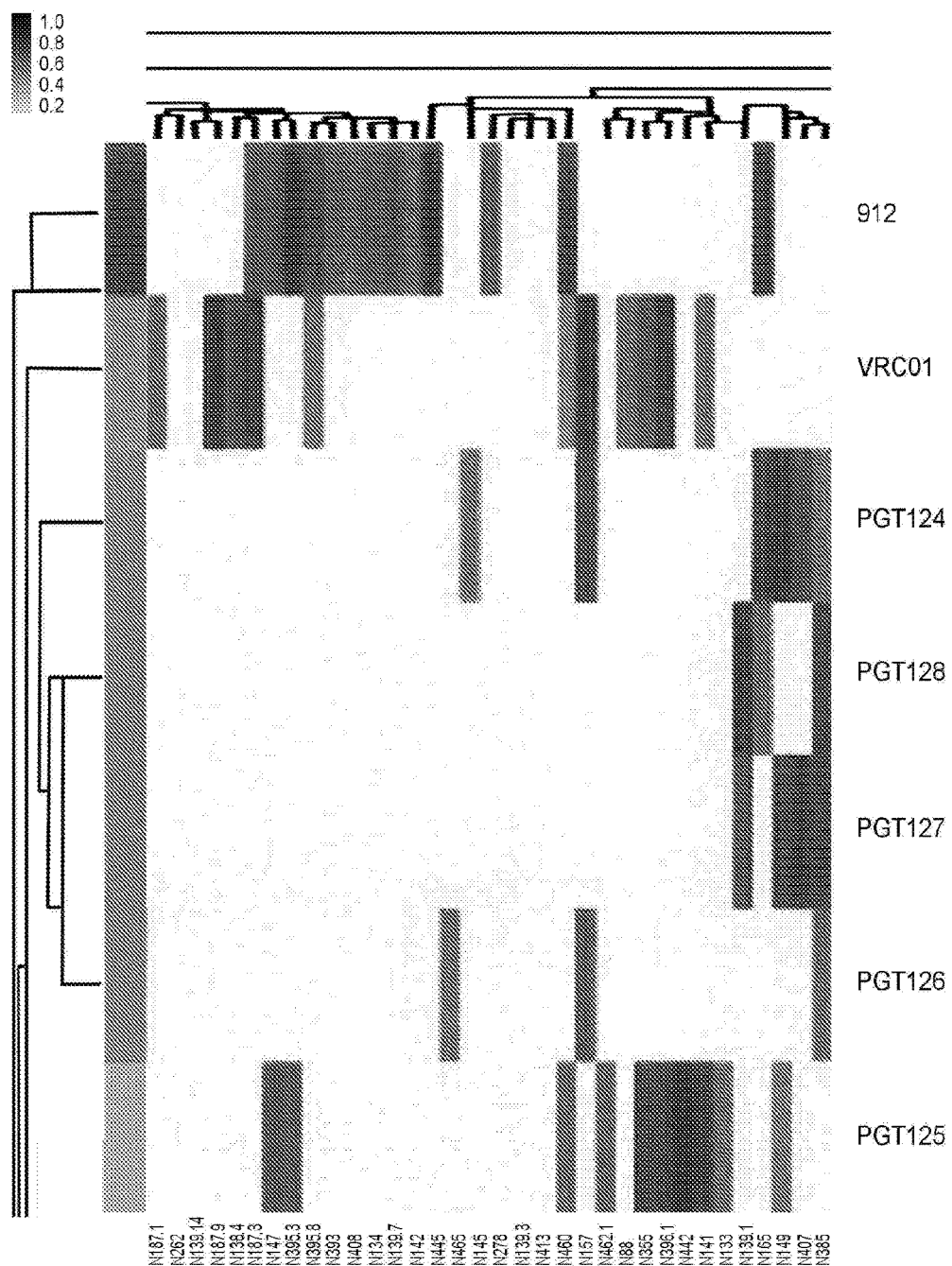
Figure 9A:
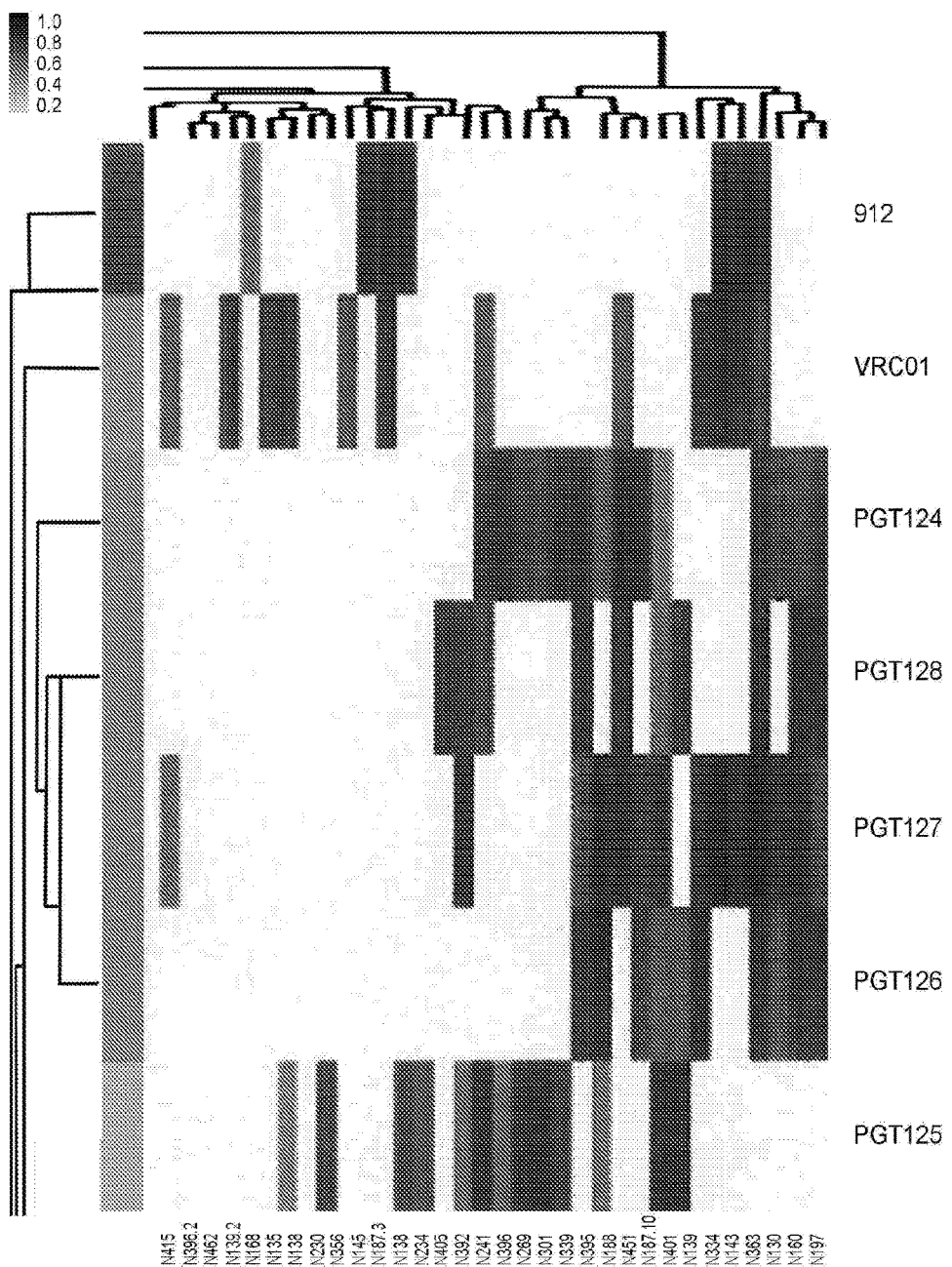
Figure 9B:
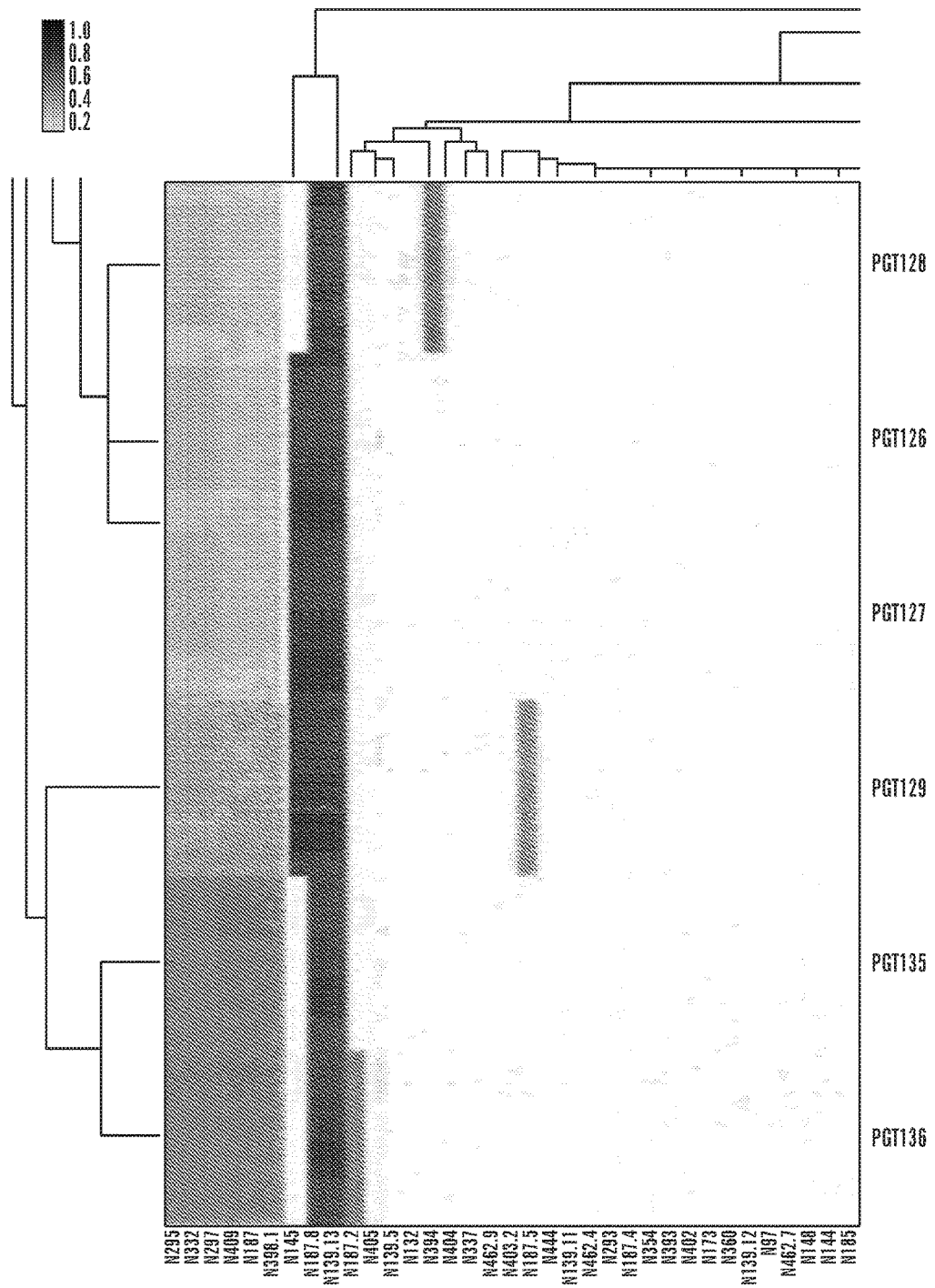
Figure 9B:
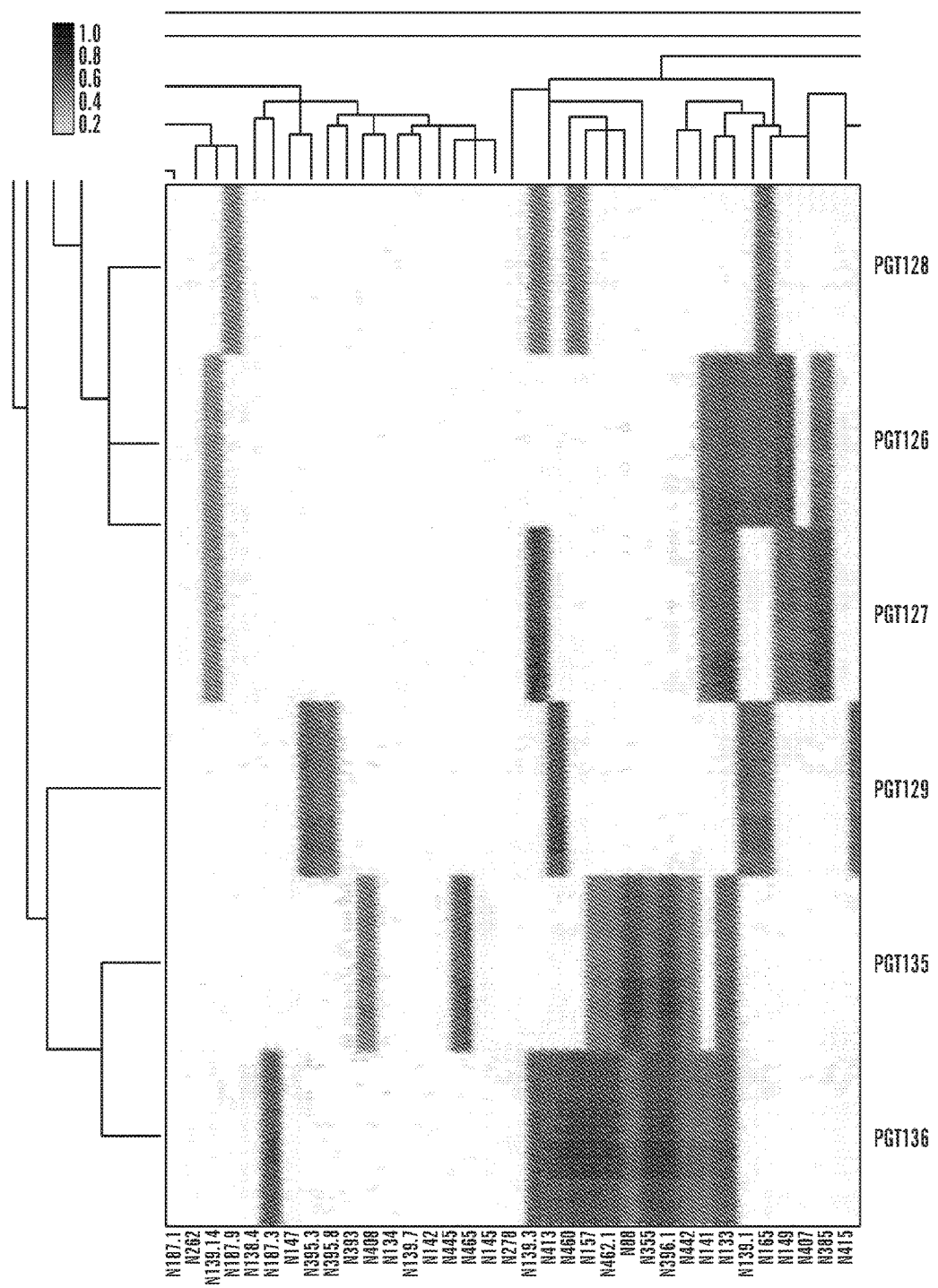
Figure 9B:
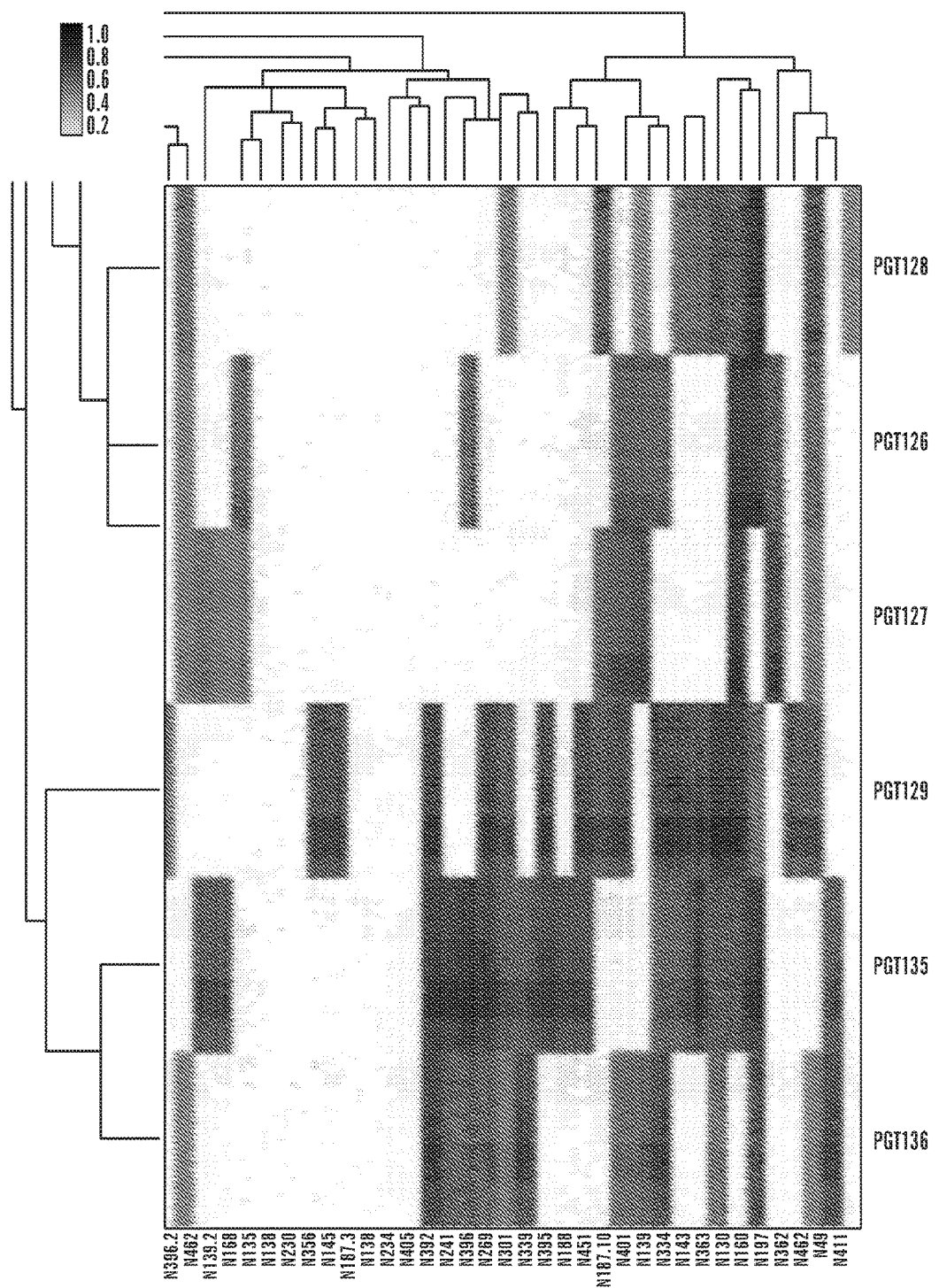

In the process, starting from a randomly selected vector of the glycan determinants, 100,000 iterations of MCMC walk were performed for each bNAb in order to converge a desired distribution, and the first 1,000 iterations as a burn-in period, which may conduct a very different distribution, were discarded. The output of the model provided marginal probabilities for each PNG. To estimate statistical significance among the PNGS, the background model was performed, in which the original glycosylation occupancy matrix were permuted by shuffling the gp120 panels to preserve the complex heterogeneity of each glycan occupancy but to capture random effects. The background model for each antibody was performed 100 permutations to estimate null distribution for individual PNGS. Only the sites whose nominal p-value shows significance (p<0.05) (FIG. 7), were identified as the glycan determinants. A customized Matlab script was used for Metropolis-Hastings MCMC algorithm and implemented Matlab LIBSVM package (Chang and Lin, 2011) for SVR.

To determine how the glycan determinants modulate antibody recognition, the direction weight (DW) was introduced and calculated as followed $$DW = p(x_i) \times d$$

$$d = \begin{cases} 1 & \text{if corr}(Ab_y, G_{x_i}) > 0 \\ -1 & \text{otherwise} \end{cases}$$

where $p(x_i)$ denoted as the probability of a PNG being a determinant which was obtained from the probabilistic model and d represented a direction [1, −1] determined by the correlation coefficient between individual glycan occupancy pattern versus the antibody fingerprint.

Example 12: De Novo Computational Design for the Optimal Immunogens

As the new developed probabilistic model with machine learning algorithm, the glycan determinants specific to bNAb have been identified. To extend this concept to downstream rational immunogen design which aims to potentially elicit a specific neutralizing antibody, the same training set was used (glycan occupancy and antibody fingerprints) and model algorithm as previously disclosed, but the global optimal solutions were searched by different criteria. Given a set of identified glycan determinants denoted as X, the model in this section attempted to classify the sites into either agonistic or antagonistic sites, $$X = \{x_1, x_2, \ldots x_m\}$$
$$x_i = \begin{cases} 1 & \text{agonistic site} \\ 0 & \text{antagonistic site} \end{cases}$$

where each glycan determinant xi contained two states [1, 0]. So, the model was to approximate this joint probability distribution P(X) by implementing the same Bayesian MCMC sampling as previous. However, −ln(likelihood($X_{opt}$)) was alternatively the predicted antigenicity from the trained SVR model given the combinatorial agonistic and antagonistic sites $X_{opt}$.

In the process of sampling in the multi-dimensional probability distribution P(X), the model performed 200,000 iterations and located the global solution such as the greatest or the worst antigenicity. Every iteration simulated the process of mutagenesis, in which the state of a selected site $x_i$ was altered between 1 and 0 as mimicking knock-out or insertion of the glycosylation sequon. The driving force of such computational evolution mainly depended on the predicted antigenicity. The final output of the model calculated the marginal probabilities of two states at every glycan determinants. High probability with state 1 suggested that the glycan determinant most likely activated antibody binding and should be included in the optimal immunogen design. Oppositely, high probability with state 0 represented antagonism to antibody recognition and the site expected to be excluded. In the end, the model was able to identify the profiles of the glycan determinants presented in the optimal immunogens with the highest or lowest antigenicity.

Example 13: Designing and Synthesizing Immunogens, Antibodies, and Vaccines

In some examples, a process is disclosed for designing synthetic immunogens or antibodies for particular antigens. For instance, in some examples, a process for synthesizing immunogens for a vaccine for HIV-1, hepatitis C, Ebola virus, influenza, and other viruses is disclosed. In other examples, the process may be utilized to make antibodies for treatment to patients.

First, to implement the following methods and systems, mutants of a specific antigen must be provided 1500. For instance, mutants or variants of the gp120 glycoprotein were provided. The trimeric envelope of HIV-1 is composed of gp120 and gp41 subunits. Accordingly, variants of the gp41 glycoprotein may be provided. In other examples, other mutants or variants of the glycoproteins may be utilized. For instance, for Ebola, mutants of the EBOV glycoprotein which is the only virally expression protein on the viron surface of the Ebola virus. For hepatitis, variants of the E1 and E2 glycoproteins may be provided 1500, and similar for additional viruses. These antigens may be purchased or synthesized.

Next, antibodies that are known to bind to the particular antigen variants or mutants selected must be provided 1510. For instance, in the example of the gp120 mutants from HIV-1, antibodies known to bind to various mutants of the HIV-1 were provided 1510. For example, several different broadly neutralizing antibodies are disclosed herein that are known to bind to the various mutants of gp120. These antibodies may be purchased or synthesized.

In other examples, antibodies may be provided that binds to the Hepatitis glycoproteins. For instance, H-111, an antibody to HCV envelope 1 protein (E1) that maps to the YEVRNVSGVYH sequence and is located near the N terminus of E1 and is able to immunoprecipitate E1E2 heterodimers. Binding of H-111 to HCV E1 genotypes 1a, 1b, 2b, and 3a indicates that the H-111 epitope is highly conserved. Accordingly, the antibody H-111 may be provided 1510.

Next, the binding affinity for the mutants for the selected antibody must be determined 1520. For instance, an ELISA affinity may be utilized as disclosed herein. Additionally a micro-array based system combined with a label-free optical scanner based on polarization-modulated oblique-incidence reflectivity difference (OI-RD) may be utilized. In other examples binding affinity may be determined by combining the kinetic exclusion assay and Biacore's calibration free concentration analysis.

Next, glycosylation sites must be identified 1530 that are common between the mutants of the antigen, or the glycoprotein and the occupancy rates must be determined 1540. Various methods may be utilized to determine site-specific glycosylation including employing a combination of specific enzymatic proteolysis (usually with trypsin), fractionation of glycopeptides (most often by liquid chromatography or affinity chromatography) and glycopeptide analysis by MS.

Other examples may use nonspecific proteases or other techniques. In this approach pronase is used, which is a mixture of exo- and endo-proteinases capable of cleaving essentially any peptide bond. The glycoprotein is digested save for small peptide 'footprints' around glycosylation sites that are protected from digestion by steric hindrance due to the glycan moiety. The products of the digestion are glycopeptides with short peptides, small (unglycosylated) dipeptides, and amino acids. Purification with solid phase extraction and subsequent MS analysis yields mass spectra that contain only glycopeptides. This method can provide site heterogeneity or determine the occupancy rates 1540.

Next, this data may be processed by a control system comprising one or more processors of a computer or other computing processors to identify glycosylation sites that are determinant 1550 of binding affinity to the antibody. For instance, a processor or processors and memory may be included on a computing device, and a model for processing the data may be stored in the memory. The glycan occupancy rates may be sent or input into the computer's input port or wirelessly from the mass spectrometer or may be entered by translation from another computing device. For instance, in some examples, a computing device may input an mzML file from a mass spectrometer, translate the file, and process the data to determine the occupancy rates 1540 for the glycosylation sites that are determinant 1550. Then, the computing device can process that data to output the design, (e.g., a schematic, map, 3D model) of the designed immunogen.

In some examples, various machine learning algorithms or other statistical analysis may be performed as disclosed herein to identify the glycosylation sites that are determinant 1550, and additionally to determine their marginal probability of being determinant. These models may be saved on a memory or on a database connected to a server.

Various machine learning algorithms or other statistical models may be utilized. For instance, one example utilized probabilistics and a machine learning regression algorithm. For instance, supervised or unsupervised learning may be utilized. For instance, a Logistic Regression algorithm or a back propagation Neural Network may be utilized. In some examples, a probabilistic model may be designed to incorporate the heterogeneity in the glycosylation and ELISA-based fingerprinting data. Conversely, the regression model may be implemented with kernels to account for mutual dependencies of multiple glycans, such as cooperatively supporting a conserved structure or the steric hindrance from spatial-localized glycans, contributing to bNAb fingerprints. Additionally, a Bayesian MCMC with Metropolis-Hastings algorithm may be introduced to reduce computing time and mathematically to assure the identification of all objective solutions during immunogen design.

In some examples, the computing device will output determinants that are above a threshold of marginal probability. The threshold may be adjusted based on the number of determinants to design an optimal immunogen (or thereby antibody). For instance, the threshold may be increased if more than a threshold number of determinants are returned. In some examples, the device will output and display a list of glycosylation sites that should be modified, including removed or added. In some examples, a chemical structure schematic map of an immungen will be output and/or displayed.

Next, an immunogen may be synthesized with altered affinity for the antibody by modifying the identified determinant glycosylation sites 1560 according to the output of the computing device. The immunogen may be synthesized through any suitable methods, including a complementary deoxyribonucleic acid (cDNA) to synthesis a protein carrier, or gene sequence encoding the carrier protein of interest can be expressed in a heterologous species, for example bacteria, and the resultant purified glycoprotein used as an immunogen. Alternatively, small synthetic peptides can be synthesized that contain amino acid sequences derived from the cDNA acid or gene. Such antipeptide antibodies crossreact with the corresponding intact native protein with surprisingly high frequency. In this way the carrier protein can be generated, and then the polysaccharides can be reacted with the protein to produce the glycoprotein. For instance, Synthetically defined glycoprotein vaccines: current status and future directions, by Adamo et al published May 7, 2013 discloses various methods for synthesizing glycoprotein vaccines and its content is herein incorporated in its entirety, including section 3 titled Glycoconjugate vaccine design, and section 4 titled Novel technologies for vaccine design.

Example 14: Computer & Hardware Implementation of System for Designing and Outputting Optimized Immunogen It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

REFERENCES

Calarese, D. A., Scanlan, C. N., Zwick, M. B., Deechongkit, S., Mimura, Y., Kunert, R., Zhu, P., Wormald, M. R., Stanfield, R. L., Roux, K. H., et al. (2003). Antibody domain exchange is an immunological solution to carbohydrate cluster recognition. Science 300, 2065-2071.

Chang, C.-C., and Lin, C.-J. (2011). LIBSVM: A library for support vector machines. ACM Trans Intell Syst Technol 2, 1-27.

Chen, L., Kwon, Y. D., Zhou, T., Wu, X., O'Dell, S., Cavacini, L., Hessell, A. J., Pancera, M., Tang, M., Xu, L., et al. (2009). Structural basis of immune evasion at the site of CD4 attachment on HIV-1 gp120. Science 326, 1123-1127.

Doria-Rose, N. A., Klein, R. M., Manion, M. M., O'Dell, S., Phogat, A., Chakrabarti, B., Hallahan, C. W., Migueles, S. A., Wrammert, J., Ahmed, R., et al. (2009). Frequency and phenotype of human immunodeficiency virus envelope-specific B cells from patients with broadly cross-neutralizing antibodies. Journal of virology 83, 188-199.

Dosenovic, P., von Boehmer, L., Escolano, A., Jardine, J., Freund, N. T., Gitlin, A. D., McGuire, A. T., Kulp, D. W., Oliveira, T., Scharf, L., et al. (2015). Immunization for HIV-1 Broadly Neutralizing Antibodies in Human Ig Knockin Mice. Cell 161, 1505-1515.

Falkowska, E., Le, K. M., Ramos, A., Doores, K. J., Lee, J. H., Blattner, C., Ramirez, A., Derking, R., van Gils, M. J., Liang, C. H., et al. (2014). Broadly neutralizing HIV antibodies define a glycan-dependent epitope on the prefusion conformation of gp41 on cleaved envelope trimers. Immunity 40, 657-668.

Francois, K. O., and Balzarini, J. (2011). The highly conserved glycan at asparagine 260 of HIV-1 gp120 is indispensable for viral entry. The Journal of biological chemistry 286, 42900-42910.

Garces, F., Sok, D., Kong, L., McBride, R., Kim, Hi., Saye-Francisco, K. F., Julien, J. P., Hua, Y., Cupo, A., Moore, J. P., et al. (2014). Structural evolution of glycan recognition by a family of potent HIV antibodies. Cell 159, 69-79.

Go, E. P., Hewawasam, G., Liao, H. X., Chen, H., Ping, L. H., Anderson, J. A., Hua, D. C., Haynes, B. F., and Desaire, H. (2011). Characterization of glycosylation profiles of HIV-1 transmitted/founder envelopes by mass spectrometry. Journal of virology 85, 8270-8284.

Ingale, J., Tran, K., Kong, L., Dey, B., McKee, K., Schief, W., Kwong, P. D., Mascola, J. R., and Wyatt, R. T. (2014). Hyperglycosylated stable core immunogens designed to present the CD4 binding site are preferentially recognized by broadly neutralizing antibodies. Journal of virology 88, 14002-14016.

Jardine, J., Julien, J. P., Menis, S., Ota, T., Kalyuzhniy, O., McGuire, A., Sok, D., Huang, P. S., MacPherson, S., Jones, M., et al. (2013). Rational HIV immunogen design to target specific germline B cell receptors. Science 340, 711-716.

Jardine, J. G., Ota, T., Sok, D., Pauthner, M., Kulp, D. W., Kalyuzhniy, O., Skog, P. D., Thinnes, T. C., Bhullar, D., Briney, B., et al. (2015). HIV-1 VACCINES. Priming a broadly neutralizing antibody response to HIV-1 using a germline-targeting immunogen. Science 349, 156-161.

Julien, J. P., Cupo, A., Sok, D., Stanfield, R. L., Lyumkis, D., Deller, M. C., Klasse, P. J., Burton, D. R., Sanders, R. W., Moore, J. P., et al. (2013a). Crystal structure of a soluble cleaved HIV-1 envelope trimer. Science 342, 1477-1483.

Julien, J. P., Sok, D., Khayat, R., Lee, J. H., Doores, K. J., Walker, L. M., Ramos, A., Diwanji, D. C., Pejchal, R., Cupo, A., et al. (2013b). Broadly neutralizing antibody PGT121 allosterically modulates CD4 binding via recognition of the HIV-1 gp120 V3 base and multiple surrounding glycans. PLoS pathogens 9, e1003342.

Kolchinsky, P., Kiprilov, E., and Sodroski, J. (2001). Increased neutralization sensitivity of CD4-independent human immunodeficiency virus variants. Journal of virology 75, 2041-2050.

Kong, L., Lee, J. H., Doores, K. J., Murin, C. D., Julien, J. P., McBride, R., Liu, Y., Marozsan, A., Cupo, A., Klasse, P. J., et al. (2013). Supersite of immune vulnerability on the glycosylated face of HIV-1 envelope glycoprotein gp120. Nature structural & molecular biology 20, 796-803.

Kwong, P. D., Wyatt, R., Robinson, J., Sweet, R. W., Sodroski, J., and Hendrickson, W. A. (1998). Structure of an HIV gp120 envelope glycoprotein in complex with the CD4 receptor and a neutralizing human antibody. Nature 393, 648-659.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. Cell 129, 123-134.

Leonard, C. K., Spellman, M. W., Riddle, L., Harris, R. J., Thomas, J. N., and Gregory, T. J. (1990). Assignment of intrachain disulfide bonds and characterization of potential glycosylation sites of the type 1 recombinant human immunodeficiency virus envelope glycoprotein (gp120) expressed in Chinese hamster ovary cells. The Journal of biological chemistry 265, 10373-10382.

Lyumkis, D., Julien, J. P., de Val, N., Cupo, A., Potter, C. S., Klasse, P. J., Burton, D. R., Sanders, R. W., Moore, J. P., Carragher, B., et al. (2013). Cryo-EM structure of a fully glycosylated soluble cleaved HIV-1 envelope trimer. Science 342, 1484-1490.

McCoy, L. E., Falkowska, E., Doores, K. J., Le, K., Sok, D., van Gils, M. J., Euler, Z., Burger, J. A., Seaman, M. S., Sanders, R. W., et al. (2015). Incomplete Neutralization and Deviation from Sigmoidal Neutralization Curves for HIV Broadly Neutralizing Monoclonal Antibodies. PLoS pathogens 11, e1005110.

McGuire, A. T., Dreyer, A. M., Carbonetti, S., Lippy, A., Glenn, J., Scheid, J. F., Mouquet, H., and Stamatatos, L. (2014). HIV antibodies. Antigen modification regulates competition of broad and narrow neutralizing HIV antibodies. Science 346, 1380-1383.

McGuire, A. T., Hoot, S., Dreyer, A. M., Lippy, A., Stuart, A., Cohen, K. W., Jardine, J., Menis, S., Scheid, J. F., West, A. P., et al. (2013). Engineering HIV envelope protein to activate germline B cell receptors of broadly neutralizing anti-CD4 binding site antibodies. The Journal of experimental medicine 210, 655-663.

McLellan, J. S., Pancera, M., Carrico, C., Gorman, J., Julien, J. P., Khayat, R., Louder, R., Pejchal, R., Sastry, M., Dai, K., et al. (2011). Structure of HIV-1 gp120 V1/V2 domain with broadly neutralizing antibody PG9. Nature 480, 336-343.

Morales, J. F., Morin, T. J., Yu, B., Tatsuno, G. P., O'Rourke, S. M., Theolis, R., Jr., Mesa, K. A., and Berman, P. W. (2014). HIV-1 envelope proteins and V1/V2 domain scaffolds with mannose-5 to improve the magnitude and quality of protective antibody responses to HIV-1. The Journal of biological chemistry 289, 20526-20542.

Pancera, M., Shahzad-Ul-Hussan, S., Doria-Rose, N. A., McLellan, J. S., Bailer, R. T., Dai, K., Loesgen, S., Louder, M. K., Staupe, R. P., Yang, Y., et al. (2013). Structural basis for diverse N-glycan recognition by HIV-1-neutralizing V1-V2-directed antibody PG16. Nature structural & molecular biology 20, 804-813.

Pantophlet, R., Wilson, I. A., and Burton, D. R. (2003). Hyperglycosylated mutants of human immunodeficiency virus (HIV) type 1 monomeric gp120 as novel antigens for HIV vaccine design. Journal of virology 77, 5889-5901.

Pantophlet, R., Wilson, I. A., and Burton, D. R. (2004). Improved design of an antigen with enhanced specificity for the broadly HIV-neutralizing antibody b12. Protein engineering, design & selection PEDS 17, 749-758.

Pejchal, R., Doores, K. J., Walker, L. M., Khayat, R., Huang, P. S., Wang, S. K., Stanfield, R. L., Julien, J. P., Ramos, A., Crispin, M., et al. (2011). A potent and broad neutralizing antibody recognizes and penetrates the HIV glycan shield. Science 334, 1097-1103.

Reeves, P. J., Callewaert, N., Contreras, R., and Khorana, H. G. (2002). Structure and function in rhodopsin: high-level expression of rhodopsin with restricted and homogeneous N-glycosylation by a tetracycline-inducible N-acetylglucosaminyltransferase I-negative HEK293 S stable mammalian cell line. Proceedings of the National Academy of Sciences of the United States of America 99, 13419-13424.

Sather, D. N., Armann, J., Ching, L K., Mavrantoni, A., Sellhom, G., Caldwell, Z., Yu, X., Wood, B., Self, S., Kalams, S., et al. (2009). Factors associated with the development of cross-reactive neutralizing antibodies during human immunodeficiency virus type 1 infection. Journal of virology 83, 757-769.

Scheid, J. F., Mouquet, H., Feldhahn, N., Seaman, M. S., Velinzon, K., Pietzsch, J., Ott, R. G., Anthony, R. M., Zebroski, H., Hurley, A., et al. (2009). Broad diversity of neutralizing antibodies isolated from memory B cells in HIV-infected individuals. Nature 458, 636-640.

Sok, D., Doores, K. J., Briney, B., Le, K. M., Saye-Francisco, K. L., Ramos, A., Kulp, D. W., Julien, J. P., Menis, S., Wickramasinghe, L., et al. (2014). Promiscuous glycan site recognition by antibodies to the high-mannose patch of gp120 broadens neutralization of HIV. Science translational medicine 6, 236ra263.

Stamatatos, L., Morris, L., Burton, D. R., and Mascola, J. R. (2009). Neutralizing antibodies generated during natural HIV-1 infection: good ss for an HIV-1 vaccine? Nature medicine 15, 866-870.

Walker, L. M., Huber, M., Doores, K. J., Falkowska, E., Pejchal, R., Julien, J. P., Wang, S. K., Ramos, A., Chan-Hui, P. Y., Moyle, M., et al. (2011). Broad neutralization coverage of HIV by multiple highly potent antibodies. Nature 477, 466-470.

Wood, N. T., Fadda, E., Davis, R., Grant, O. C., Martin, J. C., Woods, R. J., and Travers, S. A. (2013). The influence of N-linked glycans on the molecular dynamics of the HIV-1 gp120 V3 loop. PloS one 8, e80301.

Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science 329, 856-861.

Wyatt, R., Sullivan, N., Thali, M., Repke, H., Ho, D., Robinson, J., Posner, M., and Sodroski, J. (1993). Functional and immunologic characterization of human immunodeficiency virus type 1 envelope glycoproteins containing deletions of the major variable regions. Journal of virology 67, 4557-4565.

Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-817.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of synthesizing an immunogen, the method comprising:

providing a plurality of variants of a glycoprotein antigen;

providing an antibody;

determining a binding profile of each of the plurality of variants for the antibody;

identifying a plurality of consensus glycosylation sites for each of the plurality of variants;

determining a glycan occupancy rate for each of the plurality of consensus glycosylation sites;

identifying a subset of the plurality of glycosylation sites that are glycan determinants based on the determined glycan occupancy rates and binding profiles using a probabilistic model with a machine learning algorithm; and synthesizing an immunogen based on the glycoprotein antigen with an altered affinity for the antibody by modifying at least one of the subset of the plurality of glycosylation sites that are glycan determinants.

2. The method of claim 1, wherein the glycan determinants have glycan occupancy rates that exhibit a variability between the variants below a threshold.

3. The method of claim 1, wherein the glycan determinants are highly conserved between variants.

4. The method of claim 1, wherein the machine learning algorithm is a regression algorithm.

5. The method of claim 1, wherein the machine learning algorithm comprises a support vector regression.

6. The method of claim 1, wherein the glycan determinants are identified using a Bayesian Markov chain Monte Carlo algorithm.

7. The method of claim 1, wherein the glycoprotein antigen comprises an HIV envelop glycoprotein.

8. The method of claim 1, wherein the machine learning algorithm is trained using the determined glycan occupancy rates and binding affinities.

9. The method of claim 1, wherein the step of modifying at least one of the subset of the plurality of glycosylation sites comprises removing at least one of the glycosylation sequons containing at least one of the subset of the plurality of glycosylation sites.

10. The method of claim 1, wherein the step of modifying at least one of the subset of the plurality of glycosylation sites comprises adding at least one of the glycosylation sequons containing at least one of the subset of the plurality of glycosylation sites.

11. The method of claim 1, wherein the steric effect of the glycans are identified by determining the proximity of each glycan to one another.

12. A method of immunizing a patient in need thereof, comprising administering an immunogenically effective amount of the synthesized immunogen of claim 1 to prime an immune response of the patient.

13. The method of claim 12, wherein immunizing the patient results in treatment of a disease state.

14. The method of claim 12, wherein the disease state being treated comprises viral infections, bacterial infections, parasitic infections and cancer.

15. The method of claim 12, wherein the disease state being treated is HIV.

16. A system for output of a model for synthesizing an immunogen according to claim 1, the system comprising: a display; a memory containing machine readable medium comprising machine executable code having stored thereon instructions; a processor coupled to the memory, the processor configured to execute the machine executable code to cause the processor to: process occupancy data, output from a mass spectrometer, to determine a glycan occupancy rate for each of the plurality of glycosylation sites on mutants of a glycoprotein; identify, by the control system, a subset of the plurality of glycosylation sites that are glycan determinants based on the determined glycan occupancy rates and measured binding affinities for the mutants of the glycoprotein to at least one antibody; and output, to the display, a representation of an immunogen with an altered affinity for the antibody that comprises at least one of the subset of the plurality of glycosylation sites that are glycan determinants.

17. The system of claim 16, wherein the memory includes data encoding a machine learning model, and the control system is configured to identify the subset of the plurality of glycosylation sites that are glycan determinants by processing the occupancy data using the machine learning model.

18. The system of claim 16, wherein the memory is a database and the control system is a server.

* * * * *